(12) United States Patent
Einat et al.

(10) Patent No.: US 7,524,935 B2
(45) Date of Patent: Apr. 28, 2009

(54) SEQUENCES CHARACTERISTIC OF HYPOXIA-REGULATED GENE TRANSCRIPTION

(75) Inventors: Paz Einat, Nes Ziona (IL); Rami Skaliter, Nes Ziona (IL); Elena Feinstein, Rehovot (IL); Aviv Regev, Cambridge, MA (US); Hagar Kalinski, Rishon-le-Zion (IL)

(73) Assignee: Quark Pharmaceuticals, Inc., Fremont, CA (US)

( * ) Notice: Subject to any disclaimer, the term of this patent is extended or adjusted under 35 U.S.C. 154(b) by 0 days.

(21) Appl. No.: 11/440,016

(22) Filed: May 25, 2006

(65) Prior Publication Data

US 2006/0241290 A1    Oct. 26, 2006

Related U.S. Application Data

(63) Continuation of application No. 09/802,472, filed on Mar. 9, 2001, now Pat. No. 7,074,895, which is a continuation-in-part of application No. 09/384,096, filed on Aug. 27, 1999, now abandoned, which is a continuation-in-part of application No. 09/138,109, filed on Aug. 21, 1998, now abandoned.

(60) Provisional application No. 60/132,684, filed on May 5, 1999, provisional application No. 60/098,158, filed on Aug. 27, 1998, provisional application No. 60/056,453, filed on Aug. 21, 1997.

(51) Int. Cl.
*C07K 16/00* (2006.01)

(52) U.S. Cl. .................................................. 530/387.1

(58) Field of Classification Search ........................ None
See application file for complete search history.

(56) References Cited

U.S. PATENT DOCUMENTS

2007/0105122 A1* 5/2007 Ota et al. ....................... 435/6

FOREIGN PATENT DOCUMENTS

WO    WO 96/39426 A1    12/1996
WO    WO 98/39448 A2    9/1998

OTHER PUBLICATIONS

Carninci P et al (Methods Enzymol. 1999;303:19-44).*
Campbell (Monoclonal Anitbody Technology; 1984; Elsevier Science Publishing Co. Inc.; pp. 1-33).*
Adams et al, "Complementary DNA sequencing: expressed sequence tags and human genome project", *Science* 252(5013):1651-1656 (1991).
An et al, "Stabilization of wild-type p53 by Hypoxia-Inducible Factor-1α", *Nature* 392:405-408 (1998).
Bae et al, "Identification of Genes Differentially Expressed by Hypoxia in Hepatocellular Carcinoma Cells", *Biochem Biophys Res Comm* 243(1):158-162.

Barone et al, "CHOP (GADD153) and its oncogenic variant, TLS-CHOP, have opposing effects on the induction of G1/S arrest", *Genes Dev* 8(4):453-464 (1994).
Baudet et al, "1,25-Dihydroxyvitamin D3 induces programmed cell death in a rat glioma cell line", *J Neurosci Res* 46(5):540-550 (1996).
Blagosklonny et al, "p53 inhibits Hypoxia-Inducible Factor-Stimulated Transcription", *J Biol Chem* 273:11995-11998 (1998).
Blancher et al, "The molecular basis of the hypoxia response pathway: Tumour hypoxia as a therapy target", *Cancer Metastasis Rev* 17(2):187-194 (1998).
Bunn et al, "Oxygen sensing and molecular adaptation in hypoxia", *Physiol Rev* 76:839-885 (1996).
Carmeliet et al, "Role of HIF-1 alpha in hypoxia-mediated apoptosis, cell proliferation and tumor angiogenesis", *Nature* 394(6692):485-490 (Jul. 30, 1998).
Chen et al, "Down-regulation of gadd153 by c-myc in rat fibroblasts and its effect on cell growth and radiation-induced apoptosis", *Oncogene* 13(8):1659-1665 (1996).
Clark et al, "Apoptosis-suppressor gene bcl-2 expression after traumatic brain injury in rats", *J. Neurosci* 17:9172-9182 (1997).
Dor et al, "Ischemia-driven angiogenesis", *Trends Cardiovasc Med* 7:289-294 (1997).
Fleming et al, "The effects of nutrient deprivation and differentiation on the expression of growth arrest genes (gas and gadd) in F9 embryonal carcinoma cells", 330:573-579 (1998).
Forance et al, "Mammalian genes coordinately regulated by growth arrest signals and DNA-damaging agents", *Mol Cell Biol* 9:4196-4203 (1989).
Graeber et al, "Hypoxia-mediated selection of cells with diminished apoptotic potential in solid tumours", *Nature* 379(6560):88-91 (1996).
Gygi et al, "Correlation between protein and mRNA abundance in yeast", *Mol Cell Biol* 19(3):1720-1730 (1999).
Hampton et al, "Dual regulation of caspase activity by hydrogen peroxide: implications for apoptosis", *FEBS Lett* 414:552-556 (1997).
Hanahan et al, "Patterns and Emerging Mechanisms of Angiogenic Switch During Tumorigenesis", *Cell* 86:353-364 (1996).
Haynes et al, "Proteome analysis: biological assay or data archive?", *Electrophoresis* 19(11):1862-1871 (1998).

(Continued)

*Primary Examiner*—Christopher H Yaen
(74) *Attorney, Agent, or Firm*—Browdy and Neimark, P.L.L.C.

(57) ABSTRACT

There are provided polynucleotides that are modulated by hypoxic conditions. The disclosure includes such genes and proteins as well as analogs, salts and functional derivatives of such proteins, and DNA encoding such analogs, and methods of use. Methods for treating the effects of stroke, hypoxia and/or ischemia by regulating such genes or proteins are also disclosed. The presence of hypoxia or a hypoxia-associated pathology may be diagnosed by screening for the presence of at least one polynucleotide having the nucleic acid sequence according to the present invention. Methods of regulating hypoxia associated pathologies are also provided.

10 Claims, 5 Drawing Sheets

OTHER PUBLICATIONS

Hockenbery et al, "Bcl-2 functions in an antioxidant pathway to prevent apoptosis", *Cell* 75:241-251 (1993).

Hollander et al, "Analysis of the mammalian gadd45 gene and its response to DNA damage", *J Biol Chem* 268(32):24385-24393 (1993).

Kondo et al, "Modulation of apoptosis by endogenous Bcl-xL expression in MKN-45 human gastric cancer cells", *Oncogene* 17:2585-2591 (1998).

Nicholson et al, "Caspases: killer proteases", *Trends Biochem Sci* 22:299-306 (1997).

Reed JC, "Bcl-2 and the regulation of programmed cell death", *J Cell Biol* 124:1-6 (1994).

Schena et al, "Parallel Human Genome Analysis: Microarray-Based Expression Monitoring of 1000 Genes", *Proc Natl Acad Sci USA* 93(20):10614-10619 (1996).

Schmidt-Kastner et al, "Pixel-based image analysis of HSP70, GADD45 and MAP2 mRNA expression after focal cerebral ischemia: hemodynamic and histological correlates", *Brain Res Mol Brain Res* 63:79-97 (1998).

Shibata et al, "Caspases determine the vulnerability of oligodendrocytes in the ischemic brain", *J Clin. Invest* 106:643-653 (2000).

Takekawa et al, "A family of stress-inducible GADD45-like proteins mediate activation of the stress-responsive MTK1/MEKK4 MAPKKK", *Cell* 95:521-530 (1998).

Velasco-Miguel et al, "PA26, a novel target of p53 tumor suppressor and member of the GADD family of DNA damage and growth arrest inducible genes", *Oncogene* 18(1):127-137 (1999).

Wang et al, "Monitoring gene expression profile changes in ovarian carcinomas using cDNA microarray", *Gene* 229(1-2):101-108 (1999).

Wenger et al, "Oxygen(es) and the hypoxia-inducible factor-1", *Biol Chem* 378(7):609-616 (1997).

Zhan et al, "Abrogation of p53 function affects gadd gene response to DNA base-damaging agents and starvation", *DNA Cell Biol* 15:805-815 (1996).

\* cited by examiner

FIGURE 1

A
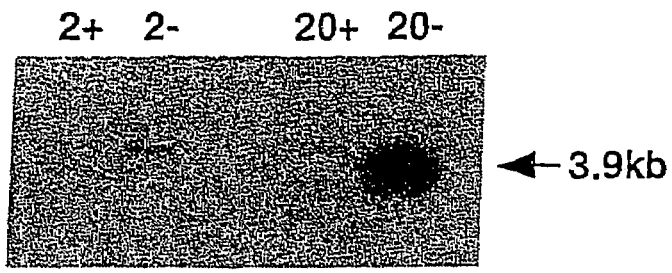
B
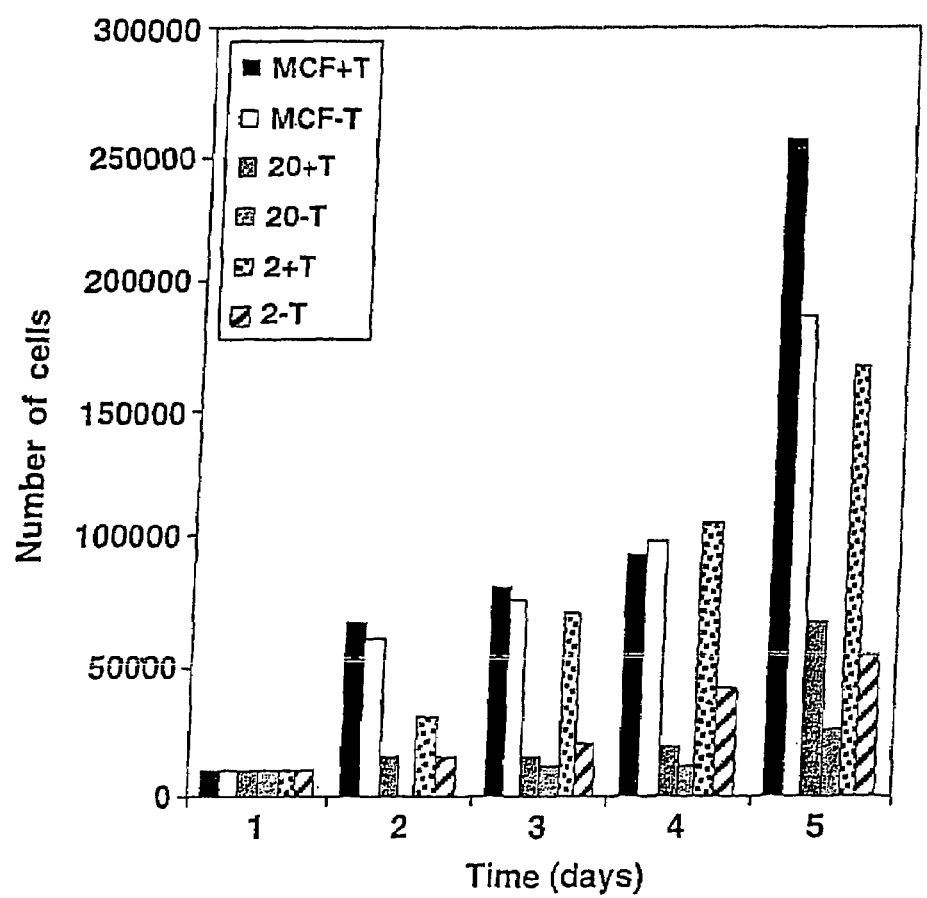
FIGURE 2

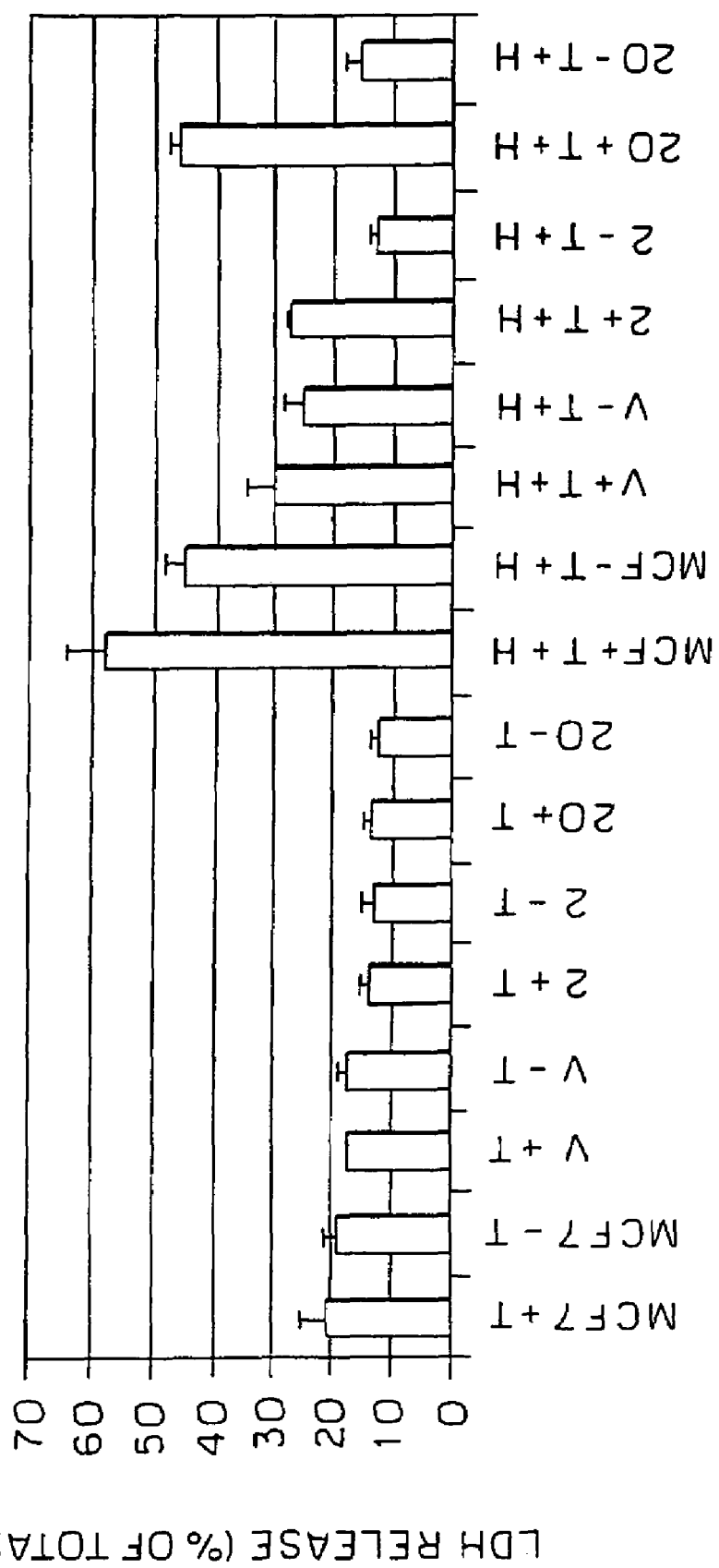

SEQUENCES CHARACTERISTIC OF HYPOXIA-REGULATED GENE TRANSCRIPTION

BACKGROUND OF THE INVENTION

1. Technical Field

The present invention relates to the identification of genes that are differentially expressed in hypoxia and use of the genes and gene products for diagnosis and therapeutic intervention. The invention further relates to identification of polynucleotide sequences, and their gene products, that are differentially expressed in hypoxia and the use of the sequences for diagnosis and probes.

2. Background Art

The level of tissue oxygenation plays an important role in normal development as well as in pathologic processes such as ischemia. Tissue oxygenation plays a significant regulatory/inducer role in both apoptosis and in angiogenesis (Bouck et al, 1996; Bunn et al, 1996; Dor et al, 1997; Carmeliet et al, 1998). Apoptosis (see Duke et al, 1996 for review) and growth arrest occur when cell growth and viability are reduced due to oxygen deprivation (hypoxia). Angiogenesis (i.e. blood vessel growth, vascularization) is stimulated when hypo-oxygenated cells secrete factors which stimulate proliferation and migration of endothelial cells in an attempt to restore oxygen homeostasis (for review see Hanahan et al, 1996).

Hypoxia plays a critical role in the selection of mutations that contribute to more severe tumorogenic phenotypes (Graeber et al, 1996). Identifying activated or inactivated genes and gene products in hypoxia and ischemia is needed.

Ischemic disease pathologies involve a decrease in the blood supply to a bodily organ, tissue or body part generally caused by constriction or obstruction of the blood vessels, as for example retinopathy, myocardial infarction and stroke. Therefore, apoptosis and/or angiogenesis as induced by the ischemic condition are also involved in these disease states. Neoangiogenesis is seen in some forms of retinopathy and in tumor growth. These processes are complex cascades of events controlled by many different genes reacting to the various stresses such as hypoxia.

Stroke is the third leading cause of death and disability in developed countries, affecting more than half a million Americans each year. Stroke is an acute neurologic injury occurring as a result of an insult to the brain, thus interrupting its blood supply. Stroke induces neuronal cell death, which leads to the clinical outcomes of patients' death or disability ranging from total paralysis to milder dysfunction. Cerebral ischemia is the most common type of stroke, which may lead to irreversible neuronal damage at the core of the ischemic focus, whereas neuronal dysfunction in the penumbra may be reversible. Cells in the penumbra have an estimated time window for survival of up to 6 hours. The ability to intervene as soon as the patient is identified is essential for recovery. It is well established that ischemic tissue damage is multifactorial and involves at least excitotoxicity, reactive oxygen species, and inflammation—all leading to neuronal cell death.

Treatment strategies for stroke are aimed to induce rapid reperfusion and rescue of neurons in the penumbral area. Neuroprotective drugs are constantly being developed in an effort to rescue neurons in the penumbra from dying. However, potential cerebroprotective agents need to counteract all the above-mentioned destructive mechanisms. Therefore, current therapy in stroke focuses primarily on prevention, minimizing subsequent worsening of the infarction, and decreasing edema.

The ability to monitor hypoxia-triggered activation of genes can provide a tool to identify not immediately evident ischemia in a patient. Identification of hypoxia-regulated genes permits the utilization of gene therapy or direct use of gene products, or alternatively inactivation of target genes for therapeutic intervention in treating the diseases and pathologies associated with hypoxia, ischemia and tumor growth.

Induction of p53 in response to hypoxia and DNA damage and its ability to inhibit cell growth in response to common cellular stresses, is a major function associated with its role as a tumor suppressor gene (Lane, 1992). Proteins encoded by p53 target genes have been shown to regulate various processes controlling growth and viability of tumor cells, such as cell cycle progression and programmed cell death. Like p53, the growth arrest and DNA damage (GADD) genes are induced in cells exposed to genotoxic stress. GADD genes were originally identified by subtraction hybridization from a cDNA library constructed from UV-irradiated Chinese hamster ovary cells (Forance et al, 1989). The GADD genes code for a diverse range of proteins with a variety of functions, including the suppression of DNA synthesis (Smith et al, 1994), the inhibition of differentiation (Batchvarova et al, 1995) and the induction of apoptosis (Takekawa et al, 1998). The response to genotoxic stress of some GADD genes is rapid but transient whereas others respond more slowly (Fleming et al, 1998). Other stimuli, such as DNA damage or contact inhibition, also increase gene expression. The regulation of these genes by stress is complex and appears to be mediated by multiple pathways. For example, ionizing radiation induces the transcription of GADD45, which inhibits proliferation and stimulates DNA excision repair, through a p53-dependent mechanism (Hollander et al, 1993). In contrast, UV irradiation increases GADD45 expression in the absence of p53 binding directly to the GADD45 promoter (Zhan et al, 1996). GADD45 mRNA levels are also increased during hypoxia, focal cerebral ischemia, and after exposure of cells to agents which elevate the levels of the glucose-regulated proteins (Price et al, 1992, Schmidt-Kastner et al, 1998). In addition to its ability to inhibit proliferation and stimulate DNA repair, GADD45 can also induce apoptosis when overexpressed in cells in vitro (Takekawa et al, 1998).

Recently, a novel p53 target gene and member of the GADD family, PA26 was identified (Velasco-Miguel et al, 1999). PA26 encodes at least three transcript isoforms, of which two are differentially induced by genotoxic stress in a p53-dependent manner. The function of PA26 is unclear.

SUMMARY OF THE INVENTION

The present invention provides purified, isolated and cloned polynucleotides (nucleic acid sequences) associated with hypoxia-regulated activity and having sequences designated as any one of SEQ ID NOs:1-12, or having complementary or allelic variation sequences thereto. The expression of these polynucleotides is modulated when cells are subjected to neurotoxic stress. The present invention includes the polynucleotides of SEQ ID NOs:1-12, as well as the naturally-occurring full-length RNAs and corresponding full-length cDNAs which include any one of these sequences.

The invention is further directed to naturally-occurring polynucleotides having at least 70% identity with any of the polynucleotides which include any one of SEQ ID NOs:1-12, or which are capable of hybridizing under moderately stringent conditions to any of such polynucleotides, and whose expression in naturally-occurring neural cells is modulated when the cells are subjected to hypoxic stress.

The present invention is also directed to fragments having at least 20 nucleotides of any of the polynucleotides of the present invention and to polynucleotide sequences complementary to any of such polynucleotides or fragments.

In a preferred embodiment, the isolated polynucleotide is a strand of a full-length cDNA.

The present invention is further directed to isolated proteins encoded by any such full-length cDNA, as well as variants which have an amino acid sequence having at least 70% identity to such an isolated protein and retain the biological activity thereof, or biologically active fragments of such protein or variant, as well as to salts or functional derivatives of any such protein, variant or biologically active fragment.

The present invention is also directed to antibodies specific to any of the proteins, variants or fragments of the present invention and to any molecule which includes the antigen-binding portion of any such antibody.

The present invention also comprehends antisense DNA of a length sufficient to prevent transcription and/or translation of a gene identified in accordance with the present invention, as well as ribozymes which specifically bind and cleave mRNA sequences identified in accordance with the present invention.

The invention also comprehends methods for screening drugs which up-regulate or down-regulate a gene which is transcribed to an RNA containing a sequence of any of any of the polynucleotides of the present invention.

The present invention is additionally directed to pharmaceutical compositions which include the nucleic acids, proteins or polypeptides in accordance with the present invention, along with pharmaceutically acceptable carriers or excipients.

In addition, the present invention is directed to knockout or transgenic non-human animals, in which a gene identified by the present invention has been introduced or knocked out.

The present invention further provides a method of regulating angiogenesis or apoptosis in a patient in need of such treatment by administering to such patient a therapeutically effective amount of an antagonist of at least one protein as encoded by the nucleic acid sequences in accordance with the present invention.

Also provided is a diagnostic method for identifying genes modulated by hypoxic conditions by detecting the presence of a polynucleotide having a nucleic acid sequence according to the present invention.

Also provided is a method of regulating hypoxia-associated pathologies by administering an effective amount of at least one antisense oligonucleotide against one of the nucleic acid sequences (SEQ ID NOs:1-12) or their proteins. There is provided a method of regulating hypoxia associated pathology by administering an effective amount of a protein encoded by the polynucleotides (SEQ ID NOs:1-12) as active ingredients in the pharmaceutically acceptable carrier.

Further, there are provided hypoxia response regulating genes.

Among the genes in accordance with the present invention is the novel gene 95, which shares homology with the PA26 gene. The mRNA levels of gene 95 are increased during hypoxia, regardless of the p53 status of the cells. In contrast, DNA damaging agents induce 95 expression in a p53-dependent manner. 95 is involved in regulation of cell survival under ischemia and hydrogen peroxide; however, it induces DNA damaged apoptosis. Conditioned medium from 95 overexpressing clones also possesses pro-apoptotic activity.

BRIEF DESCRIPTION OF THE DRAWINGS

FIG. 1 shows sequence comparison of protein 95 (SEQ ID NO:4) and PA26 (SEQ ID NO:21).

FIG. 2 is a graph showing how 95 overexpression affects the growth rate of proliferating breast tumor cells as compared to control clones in the presence or absence of tetracycline.

FIG. 5 is a graph showing the effects of 95 overexpression on protection of MCF7 cells against $H_2O_2$ (1 mM)-induced cell death. T is tetracycline and H is $H_2O_2$.

DETAILED DESCRIPTION OF PREFERRED EMBODIMENTS

I. Definitions

Figure 3:
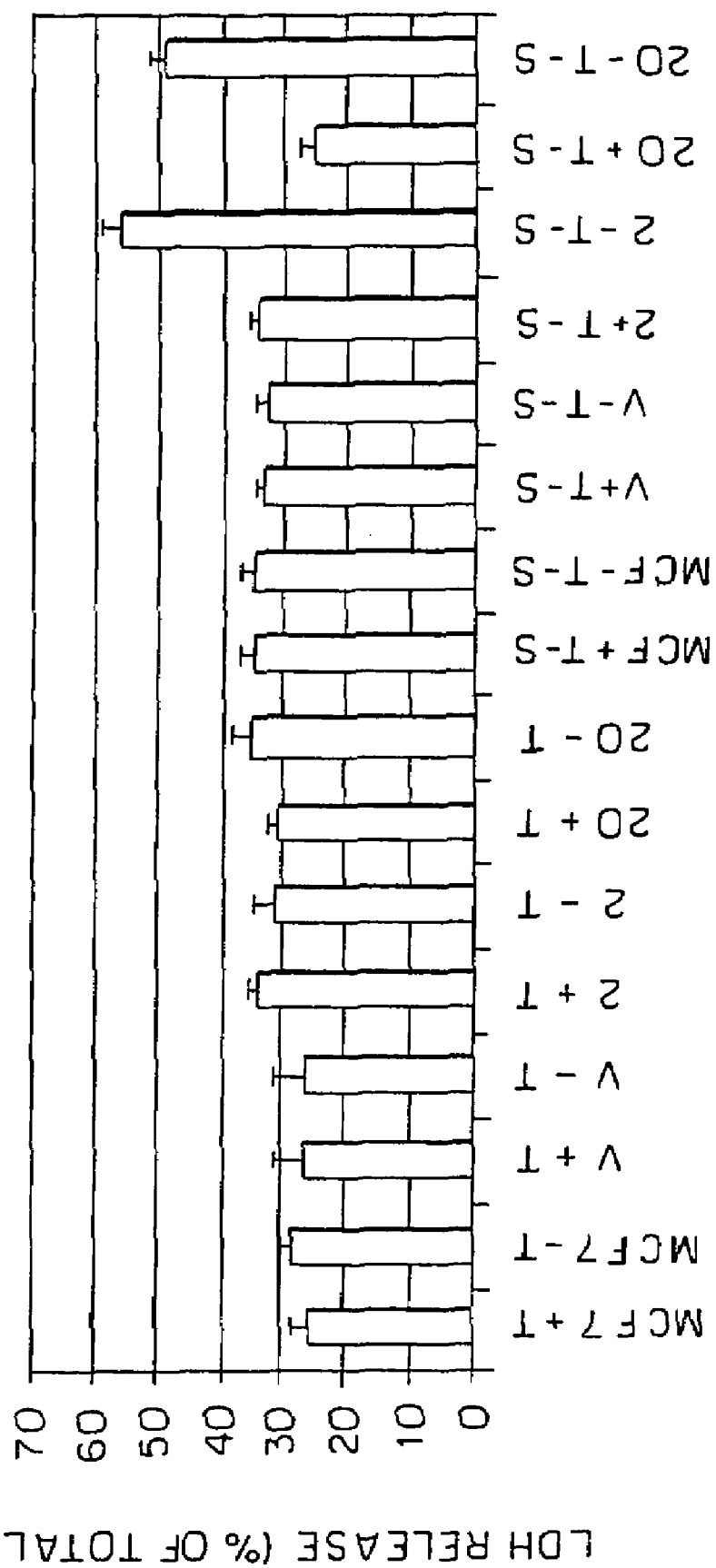
FIG. 3 is a graph showing the effects of overexpression of 95 on MCF7 induced serum deprivation (0.1%) cell death. T is tetracycyle and s is serum.

The following definitions apply to the terms used in the present specification and claims:

The term "gene" refers to the genomic nucleotide sequence which is transcribed to a full-length RNA. Such RNA molecules may be converted into corresponding cDNA molecules by techniques well known to the art of recombinant DNA technology. The term "gene" classically refers to the genomic sequence, which, upon processing, can produce different RNAs, e.g., by splicing events. However, for ease of reading, any full-length counterpart RNA sequence will also be referred to by shorthand herein as a "gene".

The term "Expressed Sequence Tag" or "EST" refers to a partial DNA or cDNA sequence of about 150 to 500, more preferably about 300, sequential nucleotides of a longer sequence obtained from a genomic or cDNA library prepared from a selected cell, cell type, tissue type, organ or organism which longer sequence corresponds to an mRNA (or other full-length RNA) transcribed by a gene found in that library. In this case, the gene is found in rat neuronal cells. One or more libraries made from a single tissue type typically provide at least about 3,000 different (i.e., unique) ESTs and potentially the full complement of all possible ESTs representing all cDNAs, e.g., 50,000-100,000 in an animal such as a human. Further background and information on the construction of ESTs is described in Adams et al (1991) and International Application Number PCT/US92/05222 (Jan. 7, 1993).

The term "apoptosis" is particularly defined as the single deletion of scattered cells by fragmentation into membrane-bound particles which are phagocytosed by other cells, believed to be due to programmed cell death. However, as used herein, it should be understood that this term should be construed more broadly as encompassing neuronal cell death, whether or not that cell death is strictly by means the apoptotic process described above.

Two proteins are "cognate" if they are produced in different species, but are sufficiently similar in structure and biological activity to be considered the equivalent proteins for those species. Two proteins may also be considered cognate if they have at least 50% amino acid sequence identity (when globally aligned with a pam250 scoring matrix with a gap penalty of the form q+r(k−1) where k is the length of the gap, q=−12 and r=−4; percent identity=number of identities as percentage of length of shorter sequence) and at least one biological activity in common. Similarly, two genes are cognate if they are expressed in different species and encode cognate proteins.

II. Novel Polynucleotide Sequences

The present invention identifies polynucleotides (nucleic acid sequences) with sequences as set forth herein in SEQ ID NOs:1-12, that have been significantly up-regulated when subjected to hypoxia. SEQ ID NOs:1-4 and 8-12 have not previously been identified. SEQ ID NO 5 was found to match sequences in data banks but has not been reported to be associated with hypoxia regulation.

To the extent that the positively identified sequence is a novel sequence, the present invention comprehends that novel sequence, as well as any naturally-occurring polynucleotide that includes that sequence as a part thereof. The sequence per se has utility based on the fact that it has been identified on the basis of differential expression in cells subjected to hypoxic stress. It can be used in diagnostic processes and kits for determining whether any given cells have been subjected to hypoxic stress. Even when such sequences are rat sequences, i.e., SEQ ID NOs:5 and 7, there is real-world utility for the purpose of medical research for determining in a rat model which cells have been subjected to hypoxic stress and which cells may have been protected from hypoxic stress when subjected to a treatment protocol in a rat model. By using the novel sequence as a probe, or a portion thereof as an oligonucleotide probe, one can identify the places in the organism (whether the organism is a rat when the sequence is a rat sequence or a human when the sequence is a human sequence) where the cDNA including the sequence is expressed and whether or not, or in what degree, it is expressed when subjected to various treatment protocols.

Human genes may be discovered by determining the human gene which corresponds to the rat gene discovered in accordance with the present invention. Such human genes are also useful for determining whether human cells have been subjected to hypoxic stress, for example in diagnosing whether or not a patient has suffered a stroke. As will be discussed in greater detail below, it is a procedurally routine matter to determine a cognate human gene based on the sequence of a rat gene. Thus, regardless of whether or not one knows the actual sequence of the corresponding human gene, the rat gene has utility as a probe for seeking and identifying the corresponding human gene which, when identified, will have its own utility.

The positively identified polynucleotide sequences are ESTs. The location of an EST in a full-length cDNA is determined by analyzing the EST for the presence of coding sequence. A conventional computer program is used to predict the extent and orientation of the coding region of a sequence (using all six reading frames). Based on this information, it is possible to infer the presence of start or stop codons within a sequence and whether the sequence is completely coding or completely non-coding or a combination of the two. If start or stop codons are present, then the EST can cover both part of the 5′-untranslated or 3′-untranslated part of the mRNA (respectively) as well as part of the coding sequence. If no coding sequence is present, it is likely that the EST is derived from the 3′ untranslated sequence due to its longer length and the fact that most cDNA library construction methods are biased toward the 3′ end of the mRNA. It should be understood that both coding and non-coding regions may provide ESTs equally useful in the described invention.

As will be discussed below, even ESTs are directly useful as they have a length that allows for PCR (polymerase chain reaction), for use as a hybridization probe and have a unique designation for the gene with which it hybridizes (generally under conditions sufficiently stringent to require at least 95% base pairing). For a detailed description and review of ESTs and their functional utility see, WO 93/00353 PCT Application which is incorporated herein in its entirety by reference, as well as the references by Zweiger et al, 1997; Okubo et al, 1997 and Braren et al, 1997.

The WO 93/00353 PCT application further describes how the EST sequences can be used to identify the transcribed genes.

Methods for obtaining complete gene sequences from ESTs are well-known to those of skill in the art. See, generally, Sambrook et al, (1989) and Ausubel et al (1994-2000). Briefly, one suitable method involves purifying the DNA from the clone that was sequenced to give the EST and labeling the isolated insert DNA. Suitable labeling systems are well known to those of skill in the art. See, e.g., Davis et al (1986). The labeled EST insert is then used as a probe to screen a lambda phage cDNA library or a plasmid cDNA library, identifying colonies containing clones related to the probe cDNA that can be purified by known methods. The ends of the newly purified clones are then sequenced to identify full-length sequences and complete sequencing of full-length clones is performed by enzymatic digestion or primer walking. A similar screening and clone selection approach can be applied to clones from a genomic DNA library. The entire naturally-occurring cDNA or gene sequence, including any allelic variations thereof, all will have the same utility as discussed above for the identified polynucleotide.

The complete gene sequence of naturally-occurring variants of the gene in question, such as, for example, allelic variations, may be determined by hybridization of a cDNA library using a probe which is based on the identified polynucleotide, under highly stringent conditions or under moderately stringent conditions. Stringency conditions are a function of the temperature used in the hybridization experiment and washes, the molarity of the monovalent cations in the hybridization solution and in the wash solution(s) and the percentage of formamide in the hybridization solution. In general, sensitivity by hybridization with a probe is affected by the amount and specific activity of the probe, the amount of the target nucleic acid, the detectability of the label, the rate of hybridization, and the duration of the hybridization. The hybridization rate is maximized at a Ti (incubation temperature) of 20-25° C. below Tm for DNA:DNA hybrids and 10-15° C. below Tm for DNA:RNA hybrids. It is also maximized by an ionic strength of about 1.5M Na$^+$. The rate is directly proportional to duplex length and inversely proportional to the degree of mismatching.

Specificity in hybridization, however, is a function of the difference in stability between the desired hybrid and "background" hybrids. Hybrid stability is a function of duplex length, base composition, ionic strength, mismatching, and destabilizing agents (if any).

The Tm of a perfect hybrid may be estimated for DNA:DNA hybrids using the equation of Meinkoth et al (1984), as $$Tm = 81.5°\,C. + 16.6\,(\log M) + 0.41\,(\%\,GC) - 0.61\,(\%\,form) - 500/L$$

and for DNA:RNA hybrids, as $$Tm = 79.8°\,C. + 18.5\,(\log M) + 0.58\,(\%\,GC) - 11.8\,(\%\,GC)^2 - 0.56(\%\,form) - 820/L$$

where

M, molarity of monovalent cations, 0.01-0.4 M NaCl,
% GC, percentage of G and C nucleotides in DNA, 30%-75%,
% form, percentage formamide in hybridization solution, and
L, length hybrid in base pairs.

Tm is reduced by 0.5-1.5° C. (an average of 1° C. can be used for ease of calculation) for each 1% mismatching.

The Tm may also be determined experimentally. As increasing length of the hybrid (L) in the above equations increases the Tm and enhances stability, the full-length rat gene sequence can be used as the probe.

Filter hybridization is typically carried out at 68° C., and at high ionic strength (e.g., 5-6×SSC), which is non-stringent, and followed by one or more washes of increasing stringency, the last one being of the ultimately desired stringency. The equations for Tm can be used to estimate the appropriate Ti for the final wash, or the Tm of the perfect duplex can be determined experimentally and Ti then adjusted accordingly.

Hybridization conditions should be chosen so as to permit allelic variations, but avoid hybridizing to other genes. In general, stringent conditions are considered to be a Ti of 5° C. below the Tm of a perfect duplex, and a 1% divergence corresponds to a 0.5-1.5° C. reduction in Tm. Typically, rat clones were 95-100% identical to database rat sequences, and the observed sequence divergence may be artifactual (sequencing error) or real (allelic variation). Hence, use of a Ti of 5-15° C. below, more preferably 5-10° C. below, the Tm of the double stranded form of the probe is recommended for probing a rat cDNA library with rat EST probes. However, when probing for a human gene cognate, more moderate stringency hybridization conditions should be used.

As used herein, highly stringent conditions are those which are tolerant of up to about 15% sequence divergence, while moderately stringent conditions are those which are tolerant of up to about 30-35% sequence divergence. Without limitation, examples of highly stringent (5-15° C. below the calculated Tm of the hybrid) and moderately stringent (15-20° C. below the calculated Tm of the hybrid) conditions use a wash solution of 0.1×SSC (standard saline citrate) and 0.5% SDS at the appropriate Ti below the calculated Tm of the hybrid. The ultimate stringency of the conditions is primarily due to the washing conditions, particularly if the hybridization conditions used are those which allow less stable hybrids to form along with stable hybrids. The wash conditions at higher stringency then remove the less stable hybrids. A common hybridization condition that can be used with the highly stringent to moderately stringent wash conditions described above is hybridization in a solution of 6×SSC (or 6×SSPE), 5× Denhardt's reagent, 0.5% SDS, 100 µg/ml denatured, fragmented salmon sperm DNA at an appropriate incubation temperature Ti.

Once any such naturally-occurring DNA is identified, it can be tested by means of routine experimentation to determine whether it is differentially expressed in the cells in which it naturally occurs when subjected to hypoxic stress.

The present invention is intended to comprehend any such naturally-occurring DNA which binds to an EST of the present invention or any oligonucleotide fragment thereof, preferably having at least 20, more preferably at least 50, contiguous nucleic acids, under highly stringent conditions or under moderately stringent conditions, which identified DNA molecules are determined to be differentially expressed in the cells in which they naturally occur when such cells are subjected to hypoxic stress. Any such identified DNA molecules would have the same utility as discussed above for the identified polynucleotide.

If the full-length sequence identified is a rat gene sequence or a sequence of any mammalian gene other than human, the cognate human gene sequence can be readily obtained, as would be readily appreciated by those of skill in the art. Comparison of known cognate protein and gene sequences between rat and human shows a high level of sequence identity, mostly on the order of 70% or higher. The cognate human gene sequence is quite readily identified and determined as long as there is a high level of sequence identity to the rat gene sequence.

While a rat EST sequence would be used to probe a rat cDNA library for a full-length cDNA sequence, and could even be used to probe human cDNA libraries, it would be expected that there would be some sequence divergence, especially at the EST sequence level, between cognate rat and human DNAs, which sequence divergence may be possibly as much as 25-50%. Preferably, the rat sequence used as a probe is from the coding region of the rat cDNA, as 5'- or 3'-uncoded region often lack significant homology among different mammalian species.

If a partial human cDNA is obtained, it may be used to isolate a larger human cDNA, and the process repeated as needed until the complete human cDNA is obtained.

For cross-species hybridization, such as to obtain the cognate human gene sequence from the rat gene sequence, the Ti should be reduced further, by about 0.5-1.5° C., e.g., 1° C., for each expected 1% divergence in sequence. The degree of divergence may be estimated from the known divergence of the most closely related pairs of known genes from the two species.

If the desired degree of mismatching results in a wash temperature less than 45° C., it is desirable to increase the salt concentration so a higher temperature can be used. Doubling the SSC concentration results in about a 17° C. increase in Tm, so washes at 45° C. in 0.1×SSC and 62° C. in 0.2×SSC are equivalent (1×SSC=0.15 M NaCl, 0.015M trisodium citrate, pH 7.0).

The person skilled in the art can readily determine suitable combinations of temperature and salt concentration to achieve these degrees of stringency.

Examples of successful cross-species-hybridization experiments include Braun et al (1989) (mouse v. human), Imamura et al (1991) (human v. rat), Oro et al (1988) (human v. *Drosophila*), Higuti et al (1991) (rat v. human), Jeung et al (1992) (rat, bovine v. human), Iwata et al (1992) (human v. mouse), Libert et al (1992) (dog v. human), Wang et al (1993) (human v. mouse), Jakubiczka et al (1993) (human v. bovine), Nahmias et al (1991) (human v. mouse), Potier et al (1992) (rat v. human), Chan et al (1989) (human v. mouse), Hsieh et al (1989) (human, mouse v. bovine), Sumimoto et al (1989) (human v. mouse), Boutin et al (1989) (rat v. human), He et al (1990) (human, rat v. dog, guinea pig, frog, mouse), Galizzi et al (1990) (mouse v. human). See also Gould et al (1989).

In general, for cross-species hybridization, Ti=25-35° C. below Tm. Wash temperatures and ionic strengths may be adjusted empirically until background is low enough.

Any non-rat mammalian sequences obtained from such hybridization experiments, which sequences test positive for the ability to be differentially expressed when the cells in which they naturally occur are subjected to hypoxic stress, are also encompassed by the present invention as are any non-human mammalian sequences obtained from such hybridization experiments using the human gene as a probe to find cognate non-human mammalian genes.

Fragments of any such naturally-occurring sequences also have utility and are intended to be encompassed by the present invention. Fragments of preferably at least 20, more preferably at least 50, nucleotides in length can be used as probes for the diagnostic assays described above.

Polynucleotide sequences that are complementary to any of the sequences or fragments encompassed by the present invention discussed above are also considered to be part of the present invention. Whenever any of the sequences discussed above are produced in a cell, the complementary sequence is concomitantly produced and, thus, the complementary sequence can also be used as a probe for the same diagnostic purposes.

Modifications or analogs of polynucleotides can be introduced to improve the therapeutic properties of the polynucleotides. Improved properties include increased nuclease resistance and/or increased ability to permeate cell membranes.

Nuclease resistance, where needed, is provided by any method known in the art that does not interfere with biological activity of the antisense oligodeoxy-nucleotides, cDNA and/or ribozymes as needed for the method of use and delivery (Iyer et al, 1990; Eckstein, 1985; Spitzer et al, 1988; Woolf et al, 1990; Shaw et al, 1991). Modifications that can be made to oligonucleotides in order to enhance nuclease resistance include modifying the phosphorous or oxygen heteroatom in the phosphate backbone. These include preparing methyl phosphonates, phosphorothioates, phosphorodithioates and morpholino oligomers. In one embodiment it is provided by having phosphorothioate bonds linking between the four to six 3'-terminus nucleotide bases. Alternatively, phosphorothioate bonds link all the nucleotide bases. Other modifications known in the art can be used where the biological activity is retained, but the stability to nucleases is substantially increased.

The present invention also includes all analogs of, or modifications to, a polynucleotide of the invention that does not substantially affect the function of the polynucleotide. The nucleotides can be selected from naturally occurring or synthetic modified bases. Naturally occurring bases include adenine, guanine, cytosine, thymine and uracil. Modified bases of the oligonucleotides include xanthine, hypoxanthine, 2-aminoadenine, 6-methyl, 2-propyl and other alkyl adenines, 5-halo uracil, 5-halo cytosine, 6-aza cytosine and 6-aza thymine, pseudo uracil, 4-thiuracil, 8-halo adenine, 8-aminoadenine, 8-thiol adenine, 8-thiolalkyl adenines, 8-hydroxyl adenine and other 8-substituted adenines, 8-halo guanines, 8-amino guanine, 8-thiol guanine, 8-thioalkyl guanines, 8-hydroxyl guanine and other substituted guanines, other aza and deaza adenines, other aza and deaza guanines, 5-trifluoromethyl uracil and 5-trifluoro cytosine.

In addition, analogs of nucleotides can be prepared wherein the structure of the nucleotide is fundamentally altered and that are better suited as therapeutic or experimental reagents. An example of a nucleotide analog is a peptide nucleic acid (PNA) wherein the deoxyribose (or ribose) phosphate backbone in DNA (or RNAO is replaced with a polyamide backbone which is similar to that found in peptides. PNA analogs have been shown to be resistant to degradation by enzymes and to have extended lives in vivo and in vitro. Further, PNAs have been shown to bind stronger to a complementary DNA sequence than a DNA molecule. This observation is attributed to the lack of charge repulsion between the PNA strand and the DNA strand. Other modifications that can be made to oligonucleotides include polymer backbones, cyclic backbones, or acyclic backbones.

III. Novel Proteins Encoded by Genes of Section II

Once the sequence of any full-length cDNA is obtained, the protein encompassed thereby is readily determinable by analysis of the sequence to find the start and stop codons and then decoding the amino acid sequence encoded by the cDNA. Thus, the present invention also encompasses any protein encoded by a full-length cDNA encompassed by the present invention as discussed above. Such proteins can be used for the same diagnostic utility, as discussed above for the polynucleotides, as they will be differentially expressed to the same degree that the corresponding cDNA is differentially expressed. They can be used to make a diagnostic tool which can be used to determine their presence in a cell. Thus, for example, they can be used to raise antibodies that could be used in such a diagnostic assay for the presence of such a protein. Such an assay would be useful to determine whether any given cell had been subjected to neurotoxic stress. Such proteins can also be used for any of the utilities discussed hereinbelow in the section related to methods of use.

Analogs of a protein or polypeptide encoded by the DNA sequences discovered in the assays described herein is also comprehended by the present invention. Preferably, the analog is a variant of the native sequence which has an amino acid sequence having at least 70% identity to the native amino acid sequence and retains the biological activity thereof. More preferably, such a sequence has at least 85% identity, at least 90% identity, or most preferably at least 95% identity to the native sequence.

The term "sequence identity" as used herein means that the sequences are compared as follows. The sequences are aligned using Version 9 of the Genetic Computing Group's GAP (global alignment program), using the default (BLOSUM62) matrix (values $-4$ to $+11$) with a gap open penalty of $-12$ (for the first null of a gap) and a gap extension penalty of $-4$ (per each additional consecutive null in the gap). After alignment, percentage identity is calculated by expressing the number of matches as a percentage of the number of amino acids in the claimed sequence.

Analogs in accordance with the present invention may also be determined in accordance with the following procedure. Polypeptides encoded by any nucleic acid, such as DNA or RNA, which hybridize to the complement of the native DNA or RNA under highly stringent or moderately stringent conditions, as long as that polypeptide maintains the biological activity of the native sequence are also considered to be within the scope of the present invention. Preferably, such nucleic acids hybridizing to the complement of the polynucleotides of the present invention under the specified conditions are naturally occurring nucleic acids, which may or may not be produced in cells of the same species as the original polynucleotides. As with any other analog, such polypeptide must retain the biological activity of the original polypeptide.

The term "active fragments" is intended to cover any fragment of the proteins identified by means of the present invention that retain the biological activity of the full protein. For example, fragments can be readily generated from the full protein where successive residues can be removed from either or both the N-terminus or C-terminus of the protein, or from biologically active peptides obtained therefrom by enzymatic or chemical cleavage of the polypeptide. Thus, multiple substitutions are not involved in screening for active fragments. If the removal of one or more amino acids from one end or the other does not affect the biological activity after testing in the standard tests, discussed herein, such truncated polypeptides are considered to be within the scope of the present invention. Further truncations can then be carried out until it is found where the removal of another residue destroys the biological activity.

"Functional derivatives" as used herein covers chemical derivatives which may be prepared from the functional groups which occur as side chains on the residues or the N- or C-terminal groups, by means known in the art, and are included in the invention as long as they remain pharmaceutically acceptable, i.e., they do not destroy the biological activity of the corresponding protein as described herein and do not confer toxic properties on compositions containing it. Derivatives may have chemical moieties, such as carbohydrate or phosphate residues, provided such a fraction has the same biological activity and remains pharmaceutically acceptable.

Suitable derivatives may include aliphatic esters of the carboxyl of the carboxyl groups, amides of the carboxyl groups by reaction with ammonia or with primary or secondary amines, N-acyl derivatives or free amino groups of the amino acid residues formed with acyl moieties (e.g., alkanoyl or carbocyclic aroyl groups) or O-acyl derivatives of free hydroxyl group (e.g., that of seryl or threonyl residues) formed with acyl moieties. Such derivatives may also include for example, polyethylene glycol side-chains which may mask antigenic sites and extend the residence of the complex or the portions thereof in body fluids.

Non-limiting examples of such derivatives are described below.

Cysteinyl residues most commonly are reacted with alpha-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, alpha-bromo-beta-(5-imidazoyl)propionic acid, chloroacetyl phosphate, B alkylmaleimides, 3-nitro-2-pyridyl disulfide, methyl-2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylprocarbonate at pH 5.5-7.0 because this agent is relatively specific for the histidyl side chain. Parabromophenacyl bromide also is useful; the reaction is preferably performed in 0.1 M sodium cacodylate at pH 6.0.

Lysinyl and amino terminal residues are reacted with succinic or other carboxylic acid anhydrides. Derivatization with these agents has the effect of reversing the charge of the lysinyl residues. Other suitable reagents for derivatizing alpha-amino-containing residues include imidoesters such as methyl picolinimidate; pyridoxal phosphate; pyridoxal; chloroborohydride; trinitrobenzenesulfonic acid; O-methylisourea; 2,4-pentanedione; and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high $pK_a$ of the guanidine functional group. Furthermore, these reagents may react with the groups of lysine as well as the arginine epsilon-amino group.

The specific modification of tyrosyl residues per se has been studied extensively, with particular interest in introducing spectral labels into tyrosyl residues by reaction with aromatic diazonium compounds or tetranitromethane. Most commonly, N-acetylimidazole and tetranitromethane are used to form O-acetyl tyrosyl species and 3-nitro derivatives, respectively.

Carboxyl side groups (aspartyl or glutamyl) are selectively modified by reaction with carbodiimides (R'—N—C—N—R') such as 1-cyclohexyl-3-[2-morpholinyl-(4-ethyl)]carbodiimide or 1-ethyl-3-(4-azonia-4,4-dimethlypentyl) carbodiimide. Furthermore, aspartyl and glutamyl residues are converted to asparaginyl and glutaminyl residues by reaction with ammonium ions.

Glutaminyl and asparaginyl residues are frequently deamidated to the corresponding glutamyl and aspartyl residues. Alternatively, these residues are deamidated under mildly acidic conditions. Either form of these residues falls within the scope of this invention.

The term "derivatives" is intended to include only those derivatives that do not change one amino acid to another of the twenty commonly-occurring natural amino acids.

The term "salts" herein refers to both salts of carboxyl groups and to acid addition salts of amino groups of the complex of the invention or analogs thereof. Salts of a carboxyl group may be formed by means known in the art and include inorganic salts, for example, sodium, calcium, ammonium, ferric or zinc salts, and the like, and salts with organic bases as those formed, for example, with amines, such as triethanolamine, arginine or lysine, piperidine, procaine and the like. Acid addition salts include, for example, salts with mineral acids, such as, for example, hydrochloric acid or sulfuric acid, and salts with organic acids, such as, for example, acetic acid or oxalic acid. Of course, any such salts must have substantially similar biological activity to the complex of the invention or its analogs.

IV. Known Polynucleotides and Protein Sequences

To the extent that any of the polynucleotide sequences of the present invention are determined to appear in the sequence databanks and may be part of identified known genes with known function and encode known proteins, it is not necessary to go through the hybridization steps in order to find the full-length cDNA for such ESTs. Furthermore, in most cases, it will not be necessary to find the cognate human gene experimentally. If the rat EST is part of a known rat gene, it is likely that the cognate human gene is also known. If not, it may be determined by the techniques discussed hereinabove with respect to novel rat gene sequences.

As the protein encoded by the known gene is also known, it is not necessary to use the techniques discussed hereinabove for determining the sequence encoded by a polynucleotide sequence. However, to the extent that the protein is not known, the techniques discussed hereinabove with respect to novel polynucleotide sequences may also be used.

Any known allelic variants of the known gene would also be expected to have the properties discovered by the gene discovery techniques discussed herein and, therefore, are also considered to be part of the present invention. The existence of other naturally-occurring variants having the property of having its sequence modulated when subjected to neurotoxic stress may also be determined using hybridization experiments under highly stringent conditions or moderately stringent conditions, all as discussed in detail hereinabove with respect to the novel polynucleotide sequences.

Analogs, active fragments, functional derivatives and salts of the known proteins which retain the property of that protein for the purposes of the present invention (although not necessarily for the properties previously known for that protein) are comprehended by the present invention, if novel, and their use is considered to be part of the present invention.

V. Utility of Good Genes and Bad Genes

The genes found to be differentially expressed when the cell producing them are subjected to hypoxic stress, may be genes which contribute to the adverse effects of hypoxia, such as apoptosis, and, in some circumstances, angiogenesis, or genes which contribute to the alleviation of the detrimental effects of hypoxia. The former genes, which contribute to the adverse effects of hypoxia will be referred to as "bad genes" herein. It would be desirable to down-regulate or otherwise decrease the titre of the expression product of such bad genes at the site of the hypoxic event, such as stroke. The utility of such bad genes and methods of use thereof will be discussed below.

Those genes which contribute to the alleviation of the detrimental effects of hypoxia, including avoidance of apoptosis and causing angiogenesis, will be referred to herein as "good genes". It would be desirable to up-regulate or otherwise increase the titres of the expression product of such good genes at the site of the hypoxic event. The utility of such good genes and methods of use thereof will be discussed below.

While it is not possible to directly determine from the differential expression studies in which tehse genes were found whether the DNA fragmenets found are part of a good or bad gene, it is reasonably certain that the fragments so identified are one or the other as their expression has been significantly modulated based on the hypoxic stress conditions to which the cells have been subjected. However, by means of further experimentation, which experimentation would not be considered to be undue experimentation, one can determine whether the fragments are part of good genes or bad genes. One way to test it is to create a mutation on the ATG codon of the fragment or create a frame shift mutation and then check whether its effect is the same. If the effect is different, it is a peptide which causes the effect. If the effect is the same, it is not a peptide but the RNA itself which causes the activity. Another possibility is to create a synthetic peptide and introduce it into cells to check whether it shows the relevant phenotype.

Another way to test whether the fragments are part of good genes or bad genes is to knock out the gene of interest, either in an animal with a knockout gene or by knocking out the gene in the cell line being tested. In a cell line, the cells can then be tested with hypoxic stress to determine whether the absence of that gene has a protective effect or enhances cell death. In a knockout mouse, similar tests can be conducted to see whether the absence of that gene has a protective or detrimental effect on the mouse when subjected to hypoxic stress.

A gene can be knocked out in a cell line by means of homologous recombination or by transfecting the cell line with an antisense sequence which prevents the expression of that gene, all as is well known to those of ordinary skill in this art. A gene can be knocked out in an animal such as a mouse, by the techniques discussed below.

Accordingly, even if it cannot be directly determined whether any of the specific DNA fragments of the present invention are parts of good genes or parts of bad genes, it is reasonably expected that they are parts of either one or the other, and, in either event, they have utility for the reasons discussed below. It can be determined whether they are good genes or bad genes without resorting to undue experimentation. Accordingly, such genes have utility and industrial applicability.

Good genes are useful as the protein encoded by such genes can be used to protect neural from, and ameliorate the effects of, hypoxia and ischemia, and ultimately in the therapeutic treatment of stroke, hypoxia and/or ischemia. Such genes may prevent apoptosis or promote angiogenesis. As to the latter, promotion of angiogenesis may be desirable, for example, in trauma situations where a limb must be reattached or in a transplant where revascularization is needed. Thus the genes, and the DNA encoding such a protein or active fragment or analog thereof, are useful in the recombinant production of such proteins or polypeptides. They are also useful as a target for assays for the discovery of drugs which selectively up-regulate such genes. The proteins encoded by such novel good genes, as well as active fragments thereof, analogs and functional derivatives thereof, are also part of the present invention and have utility to protect cells from, and to ameliorate the effects of, hypoxia and ischemia, and ultimately in the therapeutic treatment of stroke, hypoxia ischemia, and/or other conditions where such effects would be desirable.

It may turn out that the beneficial effect of up-regulation of a good gene is due to the production of a non-protein product of the gene's activity. Even in that case, however, up-regulation of the good gene will cause enhanced production of that product.

Good genes, whether novel or known, but whose relationship to hypoxia reported herein was previously unknown, may be used in novel processes which take advantage of these newly discovered properties. Thus, for example, the expression product of such genes, as well as active fragments, analogs and functional derivatives thereof, may be used to protect cells from the adverse effects of hypoxia or ischemia, to ameliorate the effects of hypoxia or ischemia, and ultimately for the treatment of the effects of stroke, hypoxia, ischemia, and/or other conditions where such effects would be desirable, by the therapeutic administration thereof in a manner which causes such product to be brought into the vicinity of the cells to be treated.

Bad genes are useful in that they can be used in diagnostic assays for cells that have been subjected to hypoxia or ischemia. If mRNA corresponding to such genes, or the translation product thereof, is found in the cells being assayed it is likely that they have been subjected to hypoxia or ischemia. If diagnosed pre-stroke, this may be predictive of incipient stroke. They are also useful as a target for assays for the discovery of drugs which selectively down-regulate such genes or are otherwise dominant negative with respect to the expression of the gene product of such genes. Antisense RNA that prevents the expression of such gene is also part of the present invention and is useful to protect neural cells from neurotoxicity, to ameliorate the effects of hypoxia or ischemia, and ultimately for the treatment of the effects of stroke, hypoxia and/or ischemia. The bad gene may also be used therapeutically when these "bad" effects may be useful for treating a certain condition. For example, promotion of apoptosis may be useful for removing unwanted cells, such as tumor cells. Prevention of angiogenesis may also be useful under certain circumstances.

It may turn out that the detrimental effect of up-regulation of a bad gene is due to the production of non-protein product of the gene's activity. Even in that case, however, down-regulation of the bad gene will cause diminished production of that product.

Bad genes, whether novel or known but whose relationship to hypoxia reported herein was previously unknown, may be used in novel processes which take advantage of these newly discovered properties. Antisense RNA having a sequence complementary to a portion of such gene and that prevents the expression of such gene may be produced and used therapeutically by administering same in a manner by which it enters cells which have been subjected to stroke, hypoxia, and/or ischemia in order to ameliorate the effects of such conditions. They may also be used in methods for assaying for drugs which down-regulate such genes. To the extent that such proteins are enzymes, the present invention comprehends the protection of neural cells from neurotoxicity, the amelioration of the effects of hypoxia or ischemia, and ultimately the therapeutic treatment of the effects of stroke, hypoxia and/or ischemia by administering an inhibitor of such enzyme in a manner that brings such inhibitor to the vicinity of the cells in which such enzyme has been up-regulated.

VI. Diagnostic Methods

As all of the genes of the present invention have been found to be modulated significantly upward after the cells have been subject to hypoxia, all of such genes may be considered to be a gene of interest for the purpose of the diagnostic assays reported herein.

Methods of detecting tissue hypoxia in mammalian tissue are based on the use of the mRNA of the genes of interest or the translation product thereof as a diagnostic marker for cells that have been subjected to hypoxia or ischemia. It is possible to determine the level of the mRNAs or protein translation products corresponding to these bad genes, in normal tissue or bodily fluids as compared to hypoxia tissue a bodily fluid from a subject which has suffered a hypoxic event, and, thus, determine the reference values of these genes on mRNAs or proteins which are indicative of tissue hypoxia. For identification of the gene, in situ hybridization, Southern blotting, single strand conformational polymorphism, restriction endonuclease fingerprinting (REF), PCR amplification and DNA-chip analysis using the nucleic acid sequences of the present invention as probes/primers can be used.

Methods of obtaining tissue samples for analysis include any surgical and non-surgical technique known in the art. Surgical methods include, but are not limited to biopsy such as fine needle aspirate, core biopsy, dilation and curettage.

Samples. The sample for use in the detection methods may be of any biological fluid or tissue which is reasonably expected to contain the messenger RNA transcribed from one of the above genes of interest, or a protein expressed therefrom one of the above bad genes. The bodily fluids can include tears, serum, urine, sweat or other bodily fluid where secreted proteins from the tissue that is undergoing an ischemic event can be localized. Preferably, the sample is composed of cells from the subject being tested which are suspect of having been subjected to a hypoxia event, such as neural cells from a suspected stroke area or cardiac cells from a suspect infarct area.

Analyte Binding Reagents. The assay target or analyte as a diagnostic marker may be a nucleic acid, such as mRNA of a gene of interest, or a protein translation product thereof. When the assay target is a nucleic acid, the preferred binding reagent is a complementary nucleic acid. However, the nucleic acid binding agent may also be a peptide or protein. A peptide phage library may be screened for peptides which bind the nucleic acid assay target. In a similar manner, a DNA binding protein may be randomly mutagenized in the region of its DNA recognition site, and the mutants screened for the ability to specifically bind the target. Or the hypervariable regions of antibodies may be mutagenized and the antibody mutants displayed on phage.

When the assay target is a protein, the preferred binding reagent is an antibody, the specifically binding fragment of an antibody, or a molecule that has the antigen-binding portion of an antibody. The antibody may be monoclonal or polyclonal. It can be obtained by first immunizing a mammal with the protein target, and recovering either polyclonal antiserum, or immunocytes for later fusion to obtain hybridomas, or by constructing an antibody phage library and screening the antibodies for binding to the target. The binding reagent may also be a binding molecule other than an antibody, such as a receptor fragment, an oligopeptide, or a nucleic acid. A suitable oligopeptide or nucleic acid may be identified by screening a suitable random library.

Signal Producing System (SPS). In order to detect the presence, or measure the amount, of an analyte, the assay must provide for a signal producing system (SPS) in which there is a detectable difference in the signal produced, depending on whether the analyte is present or absent (or, in a quantitative assay, on the amount of the analyte). The detectable signal may be one which is visually detectable, or one detectable only with instruments. Possible signals include production of colored or luminescent products, alteration of the characteristics (including amplitude or polarization) of absorption or emission of radiation by an assay component or product, and precipitation or agglutination of a component or product. The term "signal" is intended to include the discontinuance of an existing signal, or a change in the rate of change of an observable parameter, rather than a change in its absolute value. The signal may be monitored manually or automatically.

Labels. The component of the signal producing system which is most intimately associated with the diagnostic reagent for the analyte is called the "label". A label may be, e.g., a radioisotope, a fluorophore, an enzyme, a co-enzyme, an enzyme substrate, an electron-dense compound, an agglutinable particle, etc.

The radioactive isotope can be detected by such means as the use of a gamma counter or a scintillation counter or by autoradiography. Isotopes which are particularly useful for the purpose of the present invention are $^3$H, $^{32}$P, $^{125}$I, $^{131}$I, $^{35}$S, and $^{14}$C.

Diagnostic kits are also within the scope of this invention. Such kits include monoclonal antibodies or nucleic acid probes that can rapidly detect tissue hypoxia.

For nucleic acid probes, the radioactive labeling can be carried out according to any conventional method such as terminal labeling at the 3' or 5' position with the use of a radiolabeled nucleotide, a polynucleotide kinase (with or without dephosphorylation by a phosphatase) or a ligase (according to the extremity to be labeled). The probes can be the matrix for the synthesis of a chain consisting of several radioactive nucleotides or of several radioactive and non-radioactive nucleotides. The probes can also be prepared by a chemical synthesis using one or several radioactive nucleotides. Another method for radioactive labeling is a chemical iodination of the probes of the invention which leads to the binding of several $^{125}$I atoms on the probes.

The label may also be a fluorophore. When the fluorescently labeled reagent is exposed to light of the proper wavelength, its presence can then be detected due to fluorescence. Among the most commonly used fluorescent labeling compounds are fluorescein isothiocyanate, rhodamine, phycoerythrin, phycocyanin, allophycocyanin, o-phthaldehyde and fluorescamine.

Alternatively, fluorescence-emitting metals such as $^{125}$Eu, or others of the lanthanide series, may be incorporated into a diagnostic reagent using such metal chelating groups as diethylenetriaminepentaacetic acid (DTPA) of ethylenediamine-tetraacetic acid (EDTA).

The label may also be a chemiluminescent compound. The presence of the chemiluminescently labeled reagent is then determined by detecting the presence of luminescence that arises during the course of a chemical reaction. Examples of particularly useful chemiluminescent labeling compounds are luminol, isolumino, theromatic acridinium ester, imidazole, acridinium salt and oxalate ester.

Likewise, a bioluminescent compound may be used for labeling. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

Enzyme labels, such as horseradish peroxidase and alkaline phosphatase, can also be used. When an enzyme label is used, the signal producing system must also include a substrate for the enzyme. If the enzymatic reaction product is not itself detectable, the SPS will include one or more additional reactants so that a detectable product appears.

Conjugation Methods. A label may be conjugated, directly or indirectly (e.g., through a labeled anti-analyte binding reagent antibody), covalently (e.g., with N-succinimidyl 3-(2-pyridyldithio)propionate (SPDP)) or non-covalently, to the analyte binding reagent, to produce a diagnostic reagent.

Similarly, the analyte binding reagent may be conjugated to a solid phase support to form a solid phase ("capture") diagnostic reagent.

Suitable supports include glass, polystyrene, polypropylene, polyethylene, dextran, nylon, amylases, natural and modified celluloses, polyacrylamides, agaroses, and magnetite. The nature of the carrier can be either soluble to some extent or insoluble for the purposes of the present invention.

The support material may have virtually any possible structural configuration so long as the coupled molecule is capable of binding to its target. Thus the support configuration may be spherical, as in a bead, or cylindrical, as in the inside surface of a test tube, or the external surface of a rod. Alternatively, the surface may be flat such as a sheet, test strip, etc.

Binding Assay Formats. Binding assays may be divided into two basic types, heterogeneous and homogeneous. In heterogeneous assays, the interaction between the affinity molecule and the analyte does not affect the label, hence, to determine the amount or presence of analyte, bound label must be separated from free label. In homogeneous assays, the interaction does affect the activity of the label, and therefore analyte levels can be deduced without the need for a separation step.

In one embodiment, the analyte binding reagent is insolubilized by coupling it to a macromolecular support, and analyte in the sample is allowed to compete with a known quantity of a labeled or specifically labelable analyte analogue. The "analyte analogue" is a molecule capable of competing with analyte for binding to the analyte binding reagent, and the term is intended to include analyte itself. It may be labeled already, or it may be labeled subsequently by specifically binding the label to a moiety differentiating the analyte analogue from analyte. The solid and liquid phases are separated, and the labeled analyte analogue in one phase is quantified. The higher the level of analyte analogue in the solid phase, i.e., sticking to the analyte binding reagent, the lower the level of analyte in the sample.

In a "sandwich assay", both an insolubilized analyte binding reagent, and a labeled analyte binding reagent are employed. The analyte is captured by the insolubilized analyte binding reagent and is tagged by the labeled analyte binding reagent, forming a ternary complex. The reagents may be added to the sample in either order, or simultaneously. The analyte binding reagents may be the same or different. The amount of labeled analyte binding reagent in the ternary complex is directly proportional to the amount of analyte in the sample.

The two embodiments described above are both heterogeneous assays. However, homogeneous assays are conceivable. The key is that the label be affected by whether or not the complex is formed.

Detection of Genes of Interest. Detection of the mRNA of the genes of interest may be done by Northern blot analysis on tissue biopsies. Tissue samples from patients may be obtained and the total RNA extracted using RNAStat 60. The total RNA sample may then be resolved on denaturing gel by electrophoresis and then transferred onto a nylon membrane. After transfer of RNA onto the membrane, the membrane may then be used in hybridization with a suitable probe, which may be a synthetic probe directed against a gene already known to be a marker, or which may be a cDNA probe prepared directly from subtractive hybridization, wherein the fragment encoding the gene of interest, that is up-regulated in tissue hypoxia, will be labeled, preferably either radioactively with $^{32}$P or non-radioactively with DIG (Digoxigenin). A negative control, such as one composed of RNA sample from normal tissue of normal subjects, may be resolved side by side with the patients' sample, to determine quantitatively whether there is a significant increase in the level of gene expression. Elevation of the messenger RNA transcript from this gene would imply the presence of hypoxia, ischemia or other neurotoxic stress.

In a hybridization assay, a nucleic acid reagent is used as a probe. For probe use, only one reagent is needed, and it may hybridize to all or just a part of the target nucleic acid. Optionally, more than one probe may be used to increase specificity.

In probe-based assays, hybridizations may be carried out on filters or in solutions. Typical filters are nitrocellulose, nylon, and chemically-activated papers. The probe may be double stranded or single stranded, however, the double stranded nucleic acid will be denatured for binding.

Techniques for detecting a protein translation product of interest include, but are not limited to, immunoblotting or Western blotting, ELISA, sandwich assays, fluorescence, or biotin or enzymatic labeling with or without secondary antibodies.

Western blot analysis can be done on the tissue biopsies or tissue aspirates. This would involve resolving the proteins on an electrophoretic gel, such as an SDS PAGE gel, and transferring the resolved proteins onto a nitrocellulose or other suitable membrane. The proteins are incubated with a target binding molecule, such as an antibody.

This binding reagent may be labeled or not. If it is unlabeled, then one would also employ a secondary, labeled molecule which binds to the binding reagent. One approach involves avidinating one molecule and biotinylating the other. Another is for the secondary molecule to be a secondary antibody which binds the original binding reagent.

To improve detection of the specific protein, immunoprecipitation can be conducted. This typically will involve addition of a monoclonal antibody against the protein of interest to samples, then allowing the Ig-protein complex to precipitate after the addition of an affinity bead (ie antihuman Ig Sepharose bead). The immunoprecipitates will undergo several washings prior to transfer onto a nitrocellulose membrane. The Western blot analysis can be performed using another antibody against the primary antibody used.

There are a number of different methods of delivering the radiolabeled analyte binding reagent to the end-user in an amount sufficient to permit subsequent dynamic and/or static imaging using suitable radiodetecting devices. It may be administered by any means that enables the active agent to reach the agent's site of action in the body of a mammal. Because proteins and nucleic acids are subject to being digested when administered orally, parenteral administration, i.e., intravenous, subcutaneous, orintramuscular, would ordinarily be used to optimize absorption of an analyte binding reagent, such as an antibody, which is a protein.

The dosage is the smallest amount capable of providing a diagnostically effective image, and may be determined by means conventional in the art, using known radioimaging agents as a guide.

Typically, the imaging is carried out on the whole body of the subject, or on that portion of the body or organ relevant to the condition or disease under study. The amount of radiolabeled analyte binding reagent accumulated at a given point in time in relevant target organs can then be quantified.

A particularly suitable radiodetecting device is a scintillation camera, such as a gamma camera. A scintillation camera is a stationary device that can be used to image distribution of radiolabeled analyte binding reagent. The detection device in the camera senses the radioactive decay, the distribution of which can be recorded. Data produced by the imaging system can be digitized. The digitized information can be analyzed over time discontinuously or continuously. The digitized data can be processed to produce images, called frames, of the pattern of uptake of the radiolabeled analyte binding reagent in the target tissue/organ at a discrete point in time. In most continuous (dynamic) studies, quantitative data is obtained by observing changes in distributions of radioactive decay in the target tissue/organ over time. In other words, a time-activity analysis of the data will illustrate uptake through clearance of the radiolabeled binding protein by the target organs with time.

Various factors should be taken into consideration in selecting an appropriate radioisotope. The radioisotope must be selected with a view to obtaining good quality resolution upon imaging, should be safe for diagnostic use in humans and animals (except for animal models which will be sacrificed thereafter and will be maintained anaesthetized until then), and should preferably have a short physical half-life so as to decrease the amount of radiation received by the body (with the same exceptions). The radioisotope used should preferably be pharmacologically inert, and, in the quantities administered, should not have any substantial physiological effect.

The analyte binding reagent may be radiolabeled with different isotopes of iodine, for example $^{123}$I, $^{125}$I, or $^{131}$I (see for example, U.S. Pat. No. 4,609,725). The extent of radiolabeling must, however be monitored, since it will affect the calculations made based on the imaging results (i.e., a diiodinated analyte binding reagent will result in twice the radiation count of a similar monoiodinated analyte binding reagent over the same time frame).

In applications to human subjects, it may be desirable to use radioisotopes other than $^{125}$I for labeling in order to decrease the total dosimetry exposure of the human body and to optimize the detectability of the labeled molecule (though this radioisotope can be used if circumstances require). Ready availability for clinical use is also a factor. Accordingly, for human applications, preferred radiolabels are for example, $^{99m}$Tc, $^{67}$Ga, $^{68}$Ga, $^{90}$Y, $^{111}$In, $^{113m}$In, $^{123}$I, $^{186}$Re, $^{188}$Re or $^{211}$At.

The radiolabeled analyte binding reagent may be prepared by various methods. These include radiohalogenation by the chloramine-T method or the lactoperoxidase method and subsequent purification by HPLC (high pressure liquid chromatography), for example as described by Gutkowska et al (1987). Other known method of radiolabeling can be used, such as IODOBEADS™.

For animal models, such as mice or rats, the animal may be sacrificed after administration of the analyte binding reagent and regions which have been subjected to neurotoxic stress imaged on immobilized brain slices.

VII. Screening Methods

Each of the genes identified by means of the present invention can be used as a candidate gene in a screening assay for identifying and isolating inhibitors of hypoxia or other neurotoxic stress. Many types of screening assays are known to those of ordinary skill in the art. The specific assay which is chosen will depend to a great extent on the activity of the candidate gene or the protein expressed thereby. Thus, if it is known that the expression product of a candidate gene has enzymatic activity, then an assay which is based on inhibition of the enzymatic activity may be used. If the candidate protein is known to bind to a ligand or other interactor, then the assay can be based on the inhibition of such binding or interaction. When the candidate gene is a known gene, then many of its properties will also be known, and these can be used to determine the best screening assay. If the candidate gene is novel, then some analysis and/or experimentation will be appropriate in order to determine the best assay to be used to find inhibitors of the activity of that candidate gene. The analysis may involve a sequence analysis to find domains in the sequence which would shed light on its activity. Other experimentation described herein to identify the candidate gene and its activity, which experiment would not amount to undue experimentation, may also be engaged in so as to identify the type of screen that would be appropriate to find inhibitors or enhancers, as the case may be, for the candidate gene or the protein encoded thereby.

As is well known in the art, the screening assays may be in vivo or in vitro. An in vivo assay is a cell-based assay using any eukaryotic cell. One such cell-based system is particularly relevant in order to directly measure the activity of candidate genes which are pro-apoptotic functional genes, i.e., expression of the gene will cause apoptosis or otherwise cause cell death in target cells. One way of running such an in vivo assay uses tetracycline-inducible (Tet-inducible) gene expression. Tet-inducible gene expression is well known in the art (Hofmann et al, 1996). Tet-inducible retroviruses have been designed incorporating the Self-inactivating (SIN) feature of a 3' Ltr enhancer/promoter retroviral deletion mutant. Expression of this vector in cells is virtually undetectable in the presence of tetracycline or other active analogs. However, in the absence of Tet, expression is turned on to maximum within 48 hours after induction, with uniform increased expression of the whole population of cells that harbor the inducible retrovirus, indicating that expression is regulated uniformly within the infected cell population.

When dealing with pro-apoptotic function candidate genes, Tet-inducible expression causes apoptosis in target cells. One can screen for small molecules or peptides able to rescue the cells from the gene-triggered apoptosis.

If the gene product of the candidate gene phosphorylates with a specific target protein, a specific reporter gene construct can be designed such that phosphorylation of this reporter gene product causes its activation, which can be followed by a color reaction. The candidate gene can be specifically induced, using the Tet-inducible system discussed above, and a comparison of induced vs. non-induced genes provides a measure of reporter gene activation.

In a similar indirect assay, a reporter system can be designed that responds to changes in protein-protein interaction of the candidate protein. If the reporter responds to actual interaction with the candidate protein, a color reaction will occur.

One can also measure inhibition or stimulation of reporter gene activity by modulation of its expression levels via the specific candidate promoter or other regulatory elements. A specific promoter or regulatory element controlling the activity of a candidate gene is defined by methods well known in the art. A reporter gene is constructed which is controlled by the specific candidate gene promoter or regulatory elements. The DNA containing the specific promoter or regulatory agent is actually linked to the gene encoding the reporter. Reporter activity depends on specific activation of the promoter or regulatory element. Thus, inhibition or stimulation of the reporter will be a direct assay of stimulation/inhibition of the reporter gene.

Various in vitro screening assays are also well within the skill of those of ordinary skill in the art. For example, if enzymatic activity is to be measured, such as if the candidate protein has a kinase activity, the target protein can be defined and specific phosphorylation of the target can be followed. The assay may involve either inhibition of target phosphorylation or stimulation of target phosphorylation, both types of assay being well known in the art.

One can also measure in vitro interaction of a candidate protein with interactors. In this screen, the candidate protein is immobilized on beads. An interactor, such as a receptor ligand, is radioactively labeled and added. When it binds to the candidate protein on the bead, the amount of radioactivity carried on the beads (due to interaction with the candidate protein) can be measured. The assay would indicate inhibition of the interaction by measuring the amount of radioactivity on the bead.

Any of the screening assays, according to the present invention, will include a step of identifying the small molecule or peptide which tests positive in the assay and may also include the further step of producing that which has been so identified. The use of any such molecules identified for inhibiting hypoxia or other neurotoxic stress is also considered to be part of the present invention.

VIII. Therapeutic Methods Relating to Good Genes

In accordance with these findings, the present invention extends to the treatment of stroke by the administration of a stroke-ameliorating or stroke-inhibiting amount of an agent capable of at least partially preventing brain damage, or averting the occurrence or reducing the size and severity of an ischemic infarct due, for example, to stroke, aneurysm, cerebrovascular accident, apoplexy or other trauma. Other conditions in which apoptosis is to be prevented or angiogenesis promoted may also be treatable by administration of the good genes of the present invention. Exemplary situations where a promoter of angiogenesis would be useful include trauma situations where a limb must be reattached or in a transplant where revascularization is needed.

The present invention, therefore, extends to methods for the treatment of stroke or other conditions caused or exacerbated by hypoxia or ischemia as where apoptosis is to be prevented or angiogenesis promoted, and to corresponding pharmaceutical compositions, comprising and including, without limitation, as active ingredients a protein encoded by a good gene, as well as analogs, active fragments, functional derivatives or salts thereof.

Within minutes after cessation of local cerebral blood flow, a region of densely ischemic brain tissue becomes infarcted and dies. This infarcted core is surrounded however, by a zone of ischemic but potentially viable tissue termed the "ischemic penumbra," which receives suboptimal perfusion via collateral blood vessels. The volume of the penumbra that ultimately becomes infarcted after an acute arterial occlusion is determined by a variety of factors that mediate neurotoxicity within this zone during the hours following interrupted blood flow. The nature of these factors (including glutamate, superoxide radicals, and nitric oxide) is only partially understood, as are the complex interactions that will determine whether ischemic tissue will die or recover. Some of these factors are intrinsic to the locus of ischemia, and others are delivered to the penumbra via the circulation. The net result of signaling interactions between these factors can greatly enhance neuronal cytotoxicity in the ischemic penumbra, causing a significantly larger volume of brain damage and necrosis, with corresponding increases in functional damage. The good genes, in accordance with the present invention, participate in mediating increased volumes of cerebral infarction during focal cerebral ischemia.

Good genes may also be used as the target of screening processes to find agents capable of enhancing the expression of a good gene. Thus, the amount of mRNA produced by a cell, before and after subjecting the cell to a neurotoxic stress, such as hypoxia, and administering a test agent, will determine whether that test agent causes further enhancement of expression of that good gene, as compared to a control in which no test agent is added. Such testing can reveal agents which are useful in the treatment of stroke. Screening methods are discussed in Section VII, hereinabove.

IX. Therapeutic Methods Relating to Bad Genes

Bad genes may be used therapeutically for treating conditions in which promotion of apoptosis and/or inhibition of angiogenesis is desirable. Promotion of apoptosis would be useful in treating tumor cells. Inhibition of angiogenesis may be useful, for example, with vascular stents where ingrowth is undesirable. The present invention, therefore, extends to methods for the treatment of cancer and other conditions where promotion of apoptosis and/or inhibition of angiogenesis is desired, and to corresponding pharmaceutical compositions, comprising and including, without limitation, as active ingredients a protein encoded by a bad gene, as well as analogs, active fragments, functional derivatives or salts thereof.

Additionally, the ability of an agent to inhibit expression of bad genes provides an additional therapeutic mechanism in the treatment of stroke since it would be expected to result in a reduction in the size and severity of the infarction.

The present invention thus includes a method of screening for an agent capable of providing a neuroprotective effect and thus reducing the size and severity of infarct size in stroke, which method comprises administering a test agent concurrent with, or subsequent to, an infarct-producing amount of a product of a bad gene and measuring the resultant decrease in infarct size vis-a-vis a control dose of the infarct-producing amount of the polyamine. Such testing can reveal agents which are useful in the treatment of this aspect of stroke. Screening methods are discussed in Section VII, hereinabove.

The production and administration of antisense sequences and ribozymes that specifically bind and cleave a particular mRNA sequence are discussed in Sections XI and XII hereinafter. Such ribozymes and antisense sequences relating specifically to bad genes and the mRNA they describe will inhibit the expression of these bad genes and, thus, will provide an additional therapeutic mechanism in treating the effects of stroke, hypoxia and/or ischemia or other conditions in which apoptosis is to be inhibited and/or angiogenesis promoted. Similarly, negative dominant peptides are discussed in Section XIII. Such negative dominant peptides relating specifically to bad genes will inhibit the expression of these bad genes or the effects of the gene product of such bad genes and, thus, will provide yet another therapeutic mechanism in treating the effects of stroke, hypoxia and/or ischemia or other conditions in which apoptosis is to be inhibited and/or angiogenesis promoted.

X. Antibodies

The present invention also comprehends antibodies specific for the proteins encoded by a naturally-occurring cDNA which is part of the present invention as discussed above. Such an antibody may be used for diagnostic purposes to identify the presence of any such naturally-occurring proteins. Such antibody may be a polyclonal antibody or a monoclonal antibody or any other molecule that incorporates the antigen-binding portion of a monoclonal antibody specific for such a protein. Such other molecules may be a single-chain antibody, a humanized antibody, an F(ab) fraction, a chimeric antibody, an antibody to which is attached a label, such as fluorescent or radioactive label, or an immunotoxin in which a toxic molecule is bound to the antigen binding portion of the antibody. The examples are intended to be non-limiting. However, as long as such a molecule includes the antigen-binding portion of the antibody, it will be expected to bind to the protein and, thus, can be used for the same diagnostic purposes for which a monoclonal antibody can be used.

Conveniently, the antibodies can be prepared against the immunogen or portion thereof for example a synthetic peptide based on the sequence, or prepared recombinantly by cloning techniques or the natural gene product, and/or portions thereof can be isolated and used as the immunogen. Immunogens can be used to produce antibodies by standard antibody production technology well known to those skilled in the art as described generally in Harlow et al (1988) and Borrebaeck (1992). Antibody fragments can also be prepared from the antibodies and include Fab, F(ab')$_2$, and Fv by methods known to those skilled in the art.

For producing polyclonal antibodies a host, such as a rabbit or goat, is immunized with the immunogen or immunogen fragment, generally with an adjuvant and, if necessary, coupled to a carrier; antibodies to the immunogen are collected from the sera. Further, the polyclonal antibody can be absorbed such that it is monospecific. That is, the sera can be absorbed against related immunogens so that no cross-reactive antibodies remain in the sera rendering it monospecific.

For producing monoclonal antibodies the technique involves hyperimmunization of an appropriate donor with the immunogen, generally a mouse, and isolation of splenic antibody producing cells. These cells are fused to a cell having immortality, such as a myloma cell, to provide a fused cell hybrid which has immortality and secretes the required antibody. The cells are then cultured, in bulk, and the monoclonal antibodies harvested from the culture media for use.

For producing recombinant antibody (see generally Huston et al, 1991; Johnson et al, 1991; Mernaugh et al, 1995), messenger RNAs from antibody producing B-lymphocytes of animals, or hybridoma are reverse-transcribed to obtain complimentary DNAs (cDNAs). Antibody cDNA, which can be full or partial length, is amplified and cloned into a phage or a plasmid. The cDNA can be a partial length of heavy and light chain cDNA, separated or connected by a linker. The antibody, or antibody fragment, is expressed using a suitable expression system to obtain recombinant antibody. Antibody cDNA can also be obtained by screening pertinent expression libraries.

The antibody can be bound to a solid support substrate or conjugated with a detectable moiety or be both bound and conjugated, as is well known in the art. (For a general discussion of conjugation of fluorescent or enzymatic moieties see Johnstone et al, 1982.) The binding of antibodies to a solid support substrate is also well known in the art. (See for a general discussion Harlow et al, 1988, and Borrebaeck, 1992). The detectable moieties contemplated with the present invention can include, but are not limited to, fluorescent, metallic, enzymatic and radioactive markers such as biotin, gold, ferritin, alkaline phosphatase, β-galactosidase, peroxidase, urease, fluorescein, rhodamine, tritium, $^{14}$C and iodination.

XI. Antisense Sequences

In order to manipulate the expression of a bad gene, it is desirable to produce antisense RNA in a cell. To this end, the complete or partial cDNA of a bad gene in accordance with the present invention is inserted into an expression vector comprising a promoter. The 3' end of the cDNA is thereby inserted adjacent to the 3' end of the promoter, with the 5' end of the cDNA being separated from the 3' end of the promoter by said cDNA. Upon expression of the cDNA in a cell, an antisense RNA is therefore produced which is incapable of coding for the protein. The presence of antisense RNA in the cell reduces the expression of the cellular (genomic) copy of the bad gene.

For the production of antisense RNA, the complete cDNA may be used. Alternatively, a fragment thereof may be used, which is preferably between about 9 and 2,000 nucleotides in length, more preferably between 15 and 500 nucleotides, and most preferably between 30 and 150 nucleotides.

The fragment is preferably corresponding to a region within the 5' half of the cDNA, more preferably the 5' region comprising the 5' untranslated region and/or the first exon region, and most preferably comprising the ATG translation start site. Alternatively, the fragment may correspond to DNA sequence of the 5' untranslated region only.

Antisense intervention in the expression of specific genes can be achieved by the use of synthetic AS oligonucleotide sequences (for recent reports see Lefebvre-d'Hellencourt et al, 1995; Agrawal, 1996; Lev-Lehman et al, 1997). The oligonucleotide is preferably a DNA oligonucleotide. The length of the antisense oligonucleotide is preferably between 9 and 150, more preferably between 12 and 60, and most preferably between 15 and 50 nucleotides. Suitable antisense oligonucleotides that inhibit the production of the protein of the present invention from its encoding mRNA can be readily determined with only routine experimentation through the use of a series of overlapping oligonucleotides similar to a "gene walking" technique that is well-known in the art. Such a "walking" technique as well-known in the art of antisense development can be done with synthetic oligonucleotides to walk along the entire length of the sequence complementary to the mRNA in segments on the order of 9 to 150 nucleotides in length. This "gene walking" technique will identify the oligonucleotides that are complementary to accessible regions on the target mRNA and exert inhibitory antisense activity.

The AS oligonucleotide sequence is designed to complement a target mRNA of interest and form an RNA:AS duplex. This duplex formation can prevent processing, splicing, transport or translation of the relevant mRNA. Moreover, certain AS nucleotide sequences can elicit cellular RNase H activity when hybridized with their target mRNA, resulting in mRNA degradation (Calabretta et al, 1996). In that case, RNase H will cleave the RNA component of the duplex and can potentially release the AS to further hybridize with additional molecules of the target RNA. An additional mode of action results from the interaction of AS with genomic DNA to form a triple helix which can be transcriptionally inactive.

The sequence target segment for the antisense oligonucleotide is selected such that the sequence exhibits suitable energy related characteristics important for oligonucleotide duplex formation with their complementary templates, and shows a low potential for self-dimerization or self-complementation (Anazodo et al, 1996). For example, the computer program OLIGO 4.0 (National Biosciences, Inc.), can be used to determine antisense sequence melting temperature, free energy properties, and to estimate potential self-dimer formation and self-complimentary properties. The program allows the determination of a qualitative estimation of these two parameters (potential self-dimer formation and self-complimentary) and provides an indication of "no potential" or "some potential" or "essentially complete potential". Using this program target segments are generally selected that have estimates of no potential in these parameters. However, segments can be used that have "some potential" in one of the categories. A balance of the parameters is used in the selection as is known in the art. Further, the oligonucleotides are also selected as needed so that analog substitution do not substantially affect function.

Alternatively, an oligonucleotide based on the coding sequence of a protein capable of binding to a bad gene or the protein encoded thereby can be designed using Oligo 4.0 (National Biosciences, Inc.). Antisense molecules may also be designed to inhibit translation of an mRNA into a polypeptide by preparing an antisense which will bind in the region spanning approximately −10 to +10 nucleotides at the 5' end of the coding sequence.

The mechanism of action of antisense RNA and the current state of the art on use of antisense tools is reviewed in Kumar et al (1998). There are reviews on the chemical (Crooke, 1995; Uhlmann et al, 1990), cellular (Wagner, 1994) and therapeutic (Hanania, et al, 1995; Scanlon, et al, 1995; Gewirtz, 1993) aspects of this rapidly developing technology. The use of antisense oligonucleotides in inhibition of BMP receptor synthesis has been described by Yeh et al (1998). The use of antisense oligonucleotides for inhibiting the synthesis of the voltage-dependent potassium channel gene Kv1.4 has been described by Meiri et al (1998). The use of antisense oligonucleotides for inhibition of the synthesis of Bcl-x has been described by Kondo et al (1998). The therapeutic use of antisense drugs is discussed by Stix (1998); Flanagan (1998); Guinot et al (1998), and references therein. Within a relatively short time, ample information has accumulated about the in vitro use of AS nucleotide sequences in cultured primary cells and cell lines as well as for in vivo administration of such nucleotide sequences for suppressing specific processes and changing body functions in a transient manner. Further, enough experience is now available in vitro and in vivo in animal models and human clinical trials to predict human efficacy.

Modifications of oligonucleotides that enhance desired properties are generally used when designing antisense oligonucleotides. For instance, phosphorothioate bonds are used instead of the phosphoester bonds that naturally occur in DNA, mainly because such phosphorothioate oligonucleotides are less prone to degradation by cellular enzymes. Peng Ho et al teach that undesired in vivo side effects of phosphorothioate oligonucleotides may be reduced when using a mixed phosphodiester-phosphorothioate backbone. Preferably, 2'-methoxyribonucleotide modifications in 60% of the oligonucleotide is used. Such modified oligonucleotides are capable of eliciting an antisense effect comparable to the effect observed with phosphorothioate oligonucleotides. Peng Ho et al teach further that oligonucleotide analogs incapable of supporting ribonuclease H activity are inactive.

Therefore, the preferred antisense oligonucleotide of the present invention has a mixed phosphodiester-phosphorothioate backbone. Preferably, 2'-methoxyribonucleotide modifications in about 30% to 80%, more preferably about 60%, of the oligonucleotide are used.

In the practice of the invention, antisense oligonucleotides or antisense RNA may be used. The length of the antisense RNA is preferably from about 9 to about 3,000 nucleotides, more preferably from about 20 to about 1,000 nucleotides, most preferably from about 50 to about 500 nucleotides.

In order to be effective, the antisense oligonucleotides of the present invention must travel across cell membranes. In general, antisense oligonucleotides have the ability to cross cell membranes, apparently by uptake via specific receptors. As the antisense oligonucleotides are single-stranded molecules, they are to a degree hydrophobic, which enhances passive diffusion through membranes. Modifications may be introduced to an antisense oligonucleotide to improve its ability to cross membranes. For instance, the oligonucleotide molecule may be linked to a group which includes partially unsaturated aliphatic hydrocarbon chain and one or more polar or charged groups such as carboxylic acid groups, ester groups, and alcohol groups. Alternatively, oligonucleotides may be linked to peptide structures, which are preferably membranotropic peptides. Such modified oligonucleotides penetrate membranes more easily, which is critical for their function and may, therefore, significantly enhance their activity. Palmityl-linked oligonucleotides have been described by Gerster et al (1998). Geraniol-linked oligonucleotides have been described by Shoji et al (1998). Oligonucleotides linked to peptides, e.g., membranotropic peptides, and their preparation have been described by Soukchareun et al (1998). Modifications of antisense molecules or other drugs that target the molecule to certain cells and enhance uptake of the oligonucleotide by said cells are described by Wang (1998).

The antisense oligonucleotides of the invention are generally provided in the form of pharmaceutical compositions. These compositions are for use by injection, topical administration, or oral uptake.

Preferred uses of the pharmaceutical compositions of the invention by injection are subcutaneous injection, intraperitoneal injection, and intramuscular injection.

The pharmaceutical composition of the invention generally comprises a buffering agent, an agent which adjusts the osmolarity thereof, and optionally, one or more carriers, excipients and/or additives as known in the art, e.g., for the purposes of adding flavors, colors, lubrication, or the like to the pharmaceutical composition.

Carriers may include starch and derivatives thereof, cellulose and derivatives thereof, e.g., microcrystalline cellulose, Xanthum gum, and the like. Lubricants may include hydrogenated castor oil and the like.

A preferred buffering agent is phosphate-buffered saline solution (PBS), which solution is also adjusted for osmolarity.

A preferred pharmaceutical formulation is one lacking a carrier. Such formulations are preferably used for administration by injection, including intravenous injection.

The preparation of pharmaceutical compositions is well known in the art and has been described in many articles and textbooks, see e.g., *Remington's Pharmaceutical Sciences*, especially pp 1521-1712 therein (Gennaro, 1990).

Additives may also be selected to enhance uptake of the antisense oligonucleotide across cell membranes. Such agents are generally agents that will enhance cellular uptake of double-stranded DNA molecules. For instance, certain lipid molecules have been developed for this purpose, including the transfection reagents DOTAP (Boehringer Mannheim), Lipofectin, Lipofectam, and Transfectam, which are available commercially. For a comparison of various of these reagents in enhancing antisense oligonucleotide uptake, see e.g., Quattrone et al (1995) and Capaccioli et al (1993). The antisense oligonucleotide of the invention may also be enclosed within liposomes. The preparation and use of liposomes, e.g., using the above-mentioned transfection reagents, is well known in the art. Other methods of obtaining liposomes include the use of Sendai virus or of other viruses. Examples of publications disclosing oligonucleotide transfer into cells using the liposome technique are, e.g., Meyer et al (1998), Kita et al (1999), Nakamura et al (1998), Abe et al (1998), Soni et al (1998), Bai et al (1998), see also discussion in the same Journal p. 819-20, Bochot et al (1998), Noguchi et al (1998), Yang et al (1998), Kanamaru et al (1998), and references therein. The use of Lipofectin in liposome-mediated oligonucleotide uptake is described in Sugawa et al (1998). The use of fusogenic cationic-lipid-reconstituted influenza-virus envelopes (cationic virosomes) is described in Waelti et al (1998).

The above-mentioned cationic or non-ionic lipid agents not only serve to enhance uptake of oligonucleotides into cells, but also improve the stability of oligonucleotides that have been taken up by the cell.

XII. Ribozymes

Instead of an antisense sequence as discussed herein above, ribozymes can be utilized. This is particularly necessary in cases where antisense therapy is limited by stoichiometric considerations (Sarver et al, 1990). Ribozymes can then be used that will target the same sequence. Ribozymes are RNA molecules that possess RNA catalytic ability (see Cech for review) that cleave a specific site in a target RNA. The number of RNA molecules that are cleaved by a ribozyme is greater than the number predicted by stochiochemistry. (Hampel et al, 1989; Uhlenbeck, 1987).

Given the known mRNA sequence of a gene, ribozymes, which are RNA molecule that specifically bind and cleave said mRNA sequence (see, e.g., Chen et al (1992), Zhao et al (1993), Shore et al (1993), Joseph et al (1993), Shimayama et al (1993), and Cantor et al (1993), may be designed.

Ribozymes catalyze the phosphodiester bond cleavage of RNA. Several ribozyme structural families have been identified including Group I introns, RNase P, the hepatitis delta virus ribozyme, hammerhead ribozymes and the hairpin ribozyme originally derived from the negative strand of the tobacco ringspot virus satellite RNA (sTRSV) (Sullivan, 1994; U.S. Pat. No. 5,225,347, columns 4-5). The latter two families are derived from viroids and virusoids, in which the ribozyme is believed to separate monomers from oligomers created during rolling circle replication (Symons, 1989 and 1992). Hammerhead and hairpin ribozyme motifs are most commonly adapted for trans-cleavage of mRNAs for gene therapy (Sullivan, 1994). The ribozyme type utilized in the present invention is selected as is known in the art. Hairpin ribozymes are now in clinical trial and are the preferred type. In general the ribozyme is from 30-100 nucleotides in length.

Accordingly, a ribozyme-encoding RNA sequence may be designed that cleaves the mRNA of a bad gene of the present invention. The site of cleavage is preferably located in the coding region or in the 5' non-translated region, more preferably, in the 5' part of the coding region close to the AUG translational start codon.

A DNA encoding a ribozyme according to the present invention may be introduced into cells by way of DNA uptake, uptake of modified DNA (see modifications for oligonucleotides and proteins that result in enhanced membrane permeability, as described above for oligonucleotides and described below for proteins), or viral vector-mediated gene transfer.

XIII. Negative Dominant Peptides

Negative dominant peptide refers to a peptide encoded by a cDNA sequence that encodes only a part of a protein, i.e. a peptide (see Herskowitz, 1987). This peptide can have a different function from the protein it was derived from. It can interact with the full protein and inhibit its activity or it can interact with other proteins and inhibit their activity in response to the full protein. Negative dominant means that the peptide is able to overcome the natural proteins and fully inhibit their activity to give the cell a different characteristic, such as resistance or sensitization to killing. For therapeutic intervention either the peptide itself is delivered as the active ingredient of a pharmaceutical composition or the cDNA can be delivered to the cell utilizing the same methods as for antisense delivery.

XIV. Introduction of Proteins, Peptides, and DNA into Cells

The present invention provides proteins encoded by good genes, peptides derived therefrom, antisense DNA molecules corresponding to bad genes, peptides which are negative dominant for bad genes, and oligonucleotides. A therapeutic or research-associated use of these tools necessitates their introduction into cells of a living organism or into cultured cells. For this purpose, it is desired to improve membrane permeability of peptides, proteins and oligonucleotides. Ways to improve membrane permeability of oligonucleotides have been discussed above. The same principle, namely, derivatization with lipophilic structures, may also be used in creating peptides and proteins with enhanced membrane permeability. For instance, the sequence of a known membranotropic peptide as noted above may be added to the sequence of the peptide or protein. Further, the peptide or protein may be derivatized by partly lipophilic structures such as the above-noted hydrocarbon chains, which are substituted with at least one polar or charged group. For example, lauroyl derivatives of peptides have been described by Muranishi et al (1991). Further modifications of peptides and proteins include the oxidation of methionine residues to thereby create sulfoxide groups, as described by Zacharia et al (1991). Zacharia and coworkers also described peptide or derivatives wherein the relatively hydrophobic peptide bond is replaced by its ketomethylene isoester ($COCH_2$). It is known to those of skill in the art of protein and peptide chemistry these and other modifications enhance membrane permeability.

Another way of enhancing membrane permeability is to make use of receptors, such as virus receptors, on cell surfaces in order to induce cellular uptake of the peptide or protein. This mechanism is used frequently by viruses, which bind specifically to certain cell surface molecules. Upon binding, the cell takes the virus up into its interior. The cell surface molecule is called a virus receptor. For instance, the integrin molecules CAR and AdV have been described as virus receptors for Adenovirus (Hemmi et al, 1998, and references cited therein). The CD4, GPR1, GPR15, and STRL33 molecules have been identified as receptors/coreceptors for HIV (Edinger et al, 1998 and references cited therein).

By conjugating peptides, proteins or oligonucleotides to molecules that are known to bind to cell surface receptors, the membrane permeability of said peptides, proteins or oligonucleotides will be enhanced. Examples of suitable groups for forming conjugates are sugars, vitamins, hormones, cytokines, transferrin, asialoglycoprotein, and the like molecules. Low et al U.S. Pat. No. 5,108,921 describes the use of these molecules for the purpose of enhancing membrane permeability of peptides, proteins and oligonucleotides, and the preparation of said conjugates.

Low and coworkers further teach that molecules such as folate or biotin may be used to target the conjugate to a multitude of cells in an organism, because of the abundant and non-specific expression of the receptors for these molecules.

The above use of cell surface proteins for enhancing membrane permeability of a peptide, protein or oligonucleotide of the invention may also be used in targeting the peptide, protein or oligonucleotide of the present invention to certain cell types or tissues. For instance, if it is desired to target neural cells, it is preferable to use a cell surface protein that is expressed more abundantly on the surface of those cells.

The protein, peptide or oligonucleotide of the invention may therefore, using the above-described conjugation techniques, be targeted to a certain cell type. For instance, if it is desired to protect from neurotoxic stress in neural cell, a good gene, or protein encoded thereby, or an antisense or ribozyme of the invention designed to inhibit a bad gene, may be targeted at such cells, for instance, by using molecules that are expressed on these cells. The skilled person will recognize the possibilities of using a cell surface marker selected from a multitude of known markers of neural and other cells, and of these, further selecting those that are expressed constitutively or inducibly.

XV. Virus-Mediated Cellular Targeting

The proteins, peptides and antisense sequences of the present invention may be introduced into cells by the use of a viral vector. The use of a vaccinia vector for this purpose is described in Chapter 16 of Ausubel et al (1994-2000). The use of adenovirus vectors has been described, e.g., by Teoh et al (1998), Narumi et al (1998), Pederson et al (1998), Guang-Lin et al (1998), and references therein, Nishida et al (1998), Schwarzenberger et al (1998), and Cao et al (1998). Retroviral transfer of antisense sequences has been described by Daniel et al (1998). The use of SV-40 derived viral vectors and SV-40 based packaging systems has been described by Fang et al (1997). The use of papovaviruses which specifically target B-lymphocytes, has been described by Langner et al (1998).

When using viruses as vectors, the viral surface proteins are generally used to target the virus. As many viruses, such as the above adenovirus, are rather unspecific in their cellular tropism, it may be desirable to impart further specificity by using a cell-type or tissue-specific promoter. Griscelli et al (1998) teach the use of the ventricle-specific cardiac myosin light chain 2 promoter for heart-specific targeting of a gene whose transfer is mediated by adenovirus.

Alternatively, the viral vector may be engineered to express an additional protein on its surface, or the surface protein of the viral vector may be changed to incorporate a desired peptide sequence. The viral vector may thus be engineered to express one or more additional epitopes which may be used to target said viral vector. For instance, cytokine epitopes, MHC class II-binding peptides, or epitopes derived from homing molecules may be used to target the viral vector in accordance with the teaching of the invention. The above Langer et al. (1998) reference teach the use of heterologous binding motifs to target B-lymphotrophic papoaviruses.

XVI. Pharmaceutical Compositions

The pharmaceutical compositions of the invention are prepared generally as known in the art. Thus, pharmaceutical compositions comprising nucleic acids, e.g., ribozymes, antisense RNA or antisense oligonucleotides, are prepared as described above for pharmaceutical compositions comprising oligonucleotides and/or antisense RNA. The above considerations apply generally also to other pharmaceutical compositions. For instance, the pharmaceutical composition of the invention may contain naked DNA, e.g., good genes or fragments or derivatives thereof and a pharmaceutically acceptable carrier as known in the art. A variety of ways to enhance uptake of naked DNA is known in the art. For instance, cationic liposomes (Yotsuyanagi et al, 1998), dicationic amphiphiles (Weissig et al, 1998), fusogenic liposomes (Mizuguchi et al, 1996), mixtures of stearyl-poly(L-lysine) and low density lipoprotein (LDL), (terplex, Kim et al, 1998), and even whole bacteria of an attenuated mutant strain of *Salmonella typhimurium* (Paglia et al, 1998) have been used in the preparation of pharmaceutical compositions containing DNA.

Administration of virus particles has been described in prior art publications, see, e.g., U.S. Pat. No. 5,882,877, where Adenovirus based vectors and administration of the DNA thereof is described. The viral DNA was purified on a CsCl gradient and then dialyzed against Tris-buffered saline to remove CsCl. In these preparations, viral titers (pfu/ml) of $10^{14}$ to $10^{10}$ are preferably used. Administration of virus particles as a solution in buffered saline, to be preferably administered by subcutaneous injection, is known from U.S. Pat. No. 5,846,546. Croyle and coworkers (Croyle et al, 1998) describe a process for the preparation of a pharmaceutical composition of recombinant adenoviral vectors for oral gene delivery, using CsCl gradients and lyophilization in a sucrose-containing buffer.

The active ingredients of the pharmaceutical composition can include oligonucleotides that are nuclease resistant needed for the practice of the invention or a fragment thereof shown to have the same effect targeted against the appropriate sequence(s) and/or ribozymes. Combinations of active ingredients as disclosed in the present invention can be used including combinations of antisense sequences.

Where the pharmaceutical composition of the invention includes a peptide or protein according to the present invention, the composition will generally contain salts, preferably in physiological concentration, such as PBS (phosphate-buffered saline), or sodium chloride (0.9% w/v), and a buffering agent, such as phosphate buffer in water or in the well-known PBS buffer. In the following section, the term "peptide" is meant to include all proteins or peptides according to the invention. The preparation of pharmaceutical compositions is well known in the art, see e.g., U.S. Pat. Nos. 5,736,519, 5,733,877, 5,554,378, 5,439,688, 5,418,219, 5,354,900, 5,298,246, 5,164,372, 4,900,549, 4,755,383, 4,639,435, 4,457,917, and 4,064,236.

The peptide of the present invention, or a pharmacologically acceptable salt thereof is preferably mixed with an excipient, carrier, diluent, and optionally, a preservative or the like, pharmacologically acceptable vehicles as known in the art, see, e.g., the above U.S. patents. Examples of excipients include, glucose, mannitol, inositol, sucrose, lactose, fructose, starch, corn starch, microcrystalline cellulose, hydroxypropylcellulose, hydroxypropyl-methylcellulose, polyvinylpyrrolidone and the like. Optionally, a thickener may be added, such as a natural gum, a cellulose derivative, an acrylic or vinyl polymer, or the like.

The pharmaceutical composition is provided in solid, liquid or semi-solid form. A solid preparation may be prepared by blending the above components to provide a powdery composition. Alternatively, the pharmaceutical composition is provided as a lyophilized preparation. The liquid preparation is provided preferably as an aqueous solution, aqueous suspension, oil suspension or microcapsule composition. A semi-solid composition is provided preferably as hydrous or oily gel or ointment. About 0.001 to 60 w/v %, preferably about 0.05 to 25 w/v % of peptide is provided in the composition.

A solid composition may be prepared by mixing an excipient with a solution of the peptide of the invention, gradually adding a small quantity of water, and kneading the mixture. After drying, preferably in vacuo, the mixture is pulverized. A liquid composition may be prepared by dissolving, suspending or emulsifying the peptide of the invention in water, a buffer solution or the like. An oil suspension may be prepared by suspending or emulsifying the peptide of the invention or protein in an oleaginous base, such as sesame oil, olive oil, corn oil, soybean oil, cottonseed oil, peanut oil, lanolin, petroleum jelly, paraffin, Isopar, silicone oil, fatty acids of 6 to 30 carbon atoms or the corresponding glycerol or alcohol esters. Buffers include Sorensen buffer (*Ergeb Physiol,* 12:393, 1912), Clark-Lubs buffer (*J Bact,* 2 (1):109, 191, 1917), MacIlvaine buffer (*J Biol Chem,* 49:183, 1921), Michaelis buffer (*Die Wasserstoffinonenkonzentration,* p. 186, 1914), and Kolthoff buffer (*Biochem Z,* 179:410, 1926).

A composition may be prepared as a hydrous gel, e.g., for transnasal administration. A hydrous gel base is dissolved or dispersed in aqueous solution containing a buffer, and the peptide of the invention, and the solution warmed or cooled to give a stable gel.

Preferably, the peptide of the invention is administered through intravenous, intramuscular or subcutaneous administration. Oral administration is expected to be less effective, because the peptide may be digested before being taken up. Of course, this consideration may apply less to a peptide of the invention which is modified, e.g., by being a cyclic peptide, by containing non-naturally occurring amino acids, such as D-amino acids, or other modifications which enhance the resistance of the peptide to biodegradation. Decomposition in the digestive tract may be lessened by use of certain compositions, for instance, by confining the peptide of the invention in microcapsules such as liposomes. The pharmaceutical composition of the invention may also be administered to other mucous membranes. The pharmaceutical composition is then provided in the form of a suppository, nasal spray or sublingual tablet. The dosage of the peptide of the invention may depend upon the condition to be treated, the patient's age, bodyweight, and the route of administration, and will be determined by the attending physician.

The uptake of a peptide of the invention may be facilitated by a number of methods. For instance, a non-toxic derivative of the cholera toxin B subunit, or of the structurally related subunit B of the heal-labile enterotoxin of enterotoxic *Eschericia coli* may be added to the composition, see U.S. Pat. No. 5,554,378.

In another embodiment, the peptide of the invention is provided in a pharmaceutical composition comprising a biodegradable polymer selected from poly-1,4-butylene succinate, poly-2,3-butylene succinate, poly-1,4-butylene fumarate and poly-2,3-butylene succinate, incorporating the peptide of the invention as the pamoate, tannate, stearate or palmitate thereof. Such compositions are described, e.g., in U.S. Pat. No. 5,439,688.

In a further embodiment, a composition of the invention is a fat emulsion. The fat emulsion may be prepared by adding to a fat or oil about 0.1-2.4 w/w of emulsifier such as a phospholipid, an emulsifying aid, a stabilizer, mixing mechanically, aided by heating and/or removing solvents, adding water and isotonic agent, and optionally, adjusting adding the pH agent, isotonic agent. The mixture is then homogenized. Preferably, such fat emulsions contain an electric charge adjusting agent, such as acidic phospholipids, fatty acids, bilic acids, and salts therof. Acidic phospholipids include phosphatidylserine, phosphatidylglycerol, phosphatidylinositol, and phosphatidic acid. Bilic acids include deoxycholic acid, and taurocholic acid. The preparation of such pharmaceutical compositions is described in U.S. Pat. No. 5,733,877.

The pharmaceutical compositions containing the active ingredients of the present invention as described herein above are administered and dosed in accordance with good medical practice, taking into account the clinical condition of the individual patient, the site and method of administration, scheduling of administration, patient age, sex, body weight and other factors known to medical practitioners. The pharmaceutically "effective amount" for purposes herein is thus determined by such considerations as are known in the medical arts. The amount must be effective to achieve improvement including but not limited to improved survival rate or more rapid recovery, or improvement or elimination of symptoms and other indicators as are selected as appropriate measures by those skilled in the medical arts. The pharmaceutical compositions can be combinations of the active ingredients but will include at least one active ingredient.

The doses can be single doses or multiple doses over a period of several days. The treatment generally has a length proportional to the length of the disease process and drug effectiveness and the patient species being treated.

In one embodiment, the compound of the present invention can be administered initially by intravenous injection to bring blood levels to a suitable level. The patient's levels are then maintained by an oral dosage form, although other forms of administration, dependent upon the patient's condition and as indicated above, can be used. The quantity to be administered will vary for the patient being treated and will vary from about 100 ng/kg of body weight to 100 mg/kg of body weight per day and preferably will be from 10 µg/kg to 10 mg/kg per day.

XVII. Knock-Out or Transgenic Animals

Transgenic Mice. The introduction of gene constructs into the genome of mice (transgenic mice) is a well-established procedure. Transgenic mice provide the opportunity to examine the phenotypic outcome of over-expression or ectopic expression of genes (gain-of-function experiments). Specific phenotypes obtained after such expression is a very strong predictor of gene function. Many human genes have been expressed in transgenic mice and in most cases they function appropriately. Thus, for the purpose of examining gain-of-function, human genes can be used. Specific plasmid vector constructs are available. They carry any of a variety of promoters that allow expression of the gene in specific tissues. For example, promoters that are brain specific are available, liver specific promoters, vascular-endothelial cell specific promoters, bone specific promoters, cardiac muscle specific promoters and many more. While mice are specifically discussed herein as the transgenic animal, those of ordinary skill in the art well understand that any other eukaryotic animal can be used in the same way as described for mice to make a corresponding transgenic animal.

Knockout Mice. Loss-of-function experiments in mice are mostly done by the technique of gene knockout. The technology is well established. It requires the use of mouse genes for the purpose of generating knockout of the specific gene in embryonic stem (ES) cells that are then incorporated into the mouse germ-line cells from which mice carrying the gene knockout are generated. From a human gene there are several ways to recover the homologous mouse gene. One way is to use the human gene to probe mouse genomic libraries of lambda phages, cosmids or BACs. Positive clones are examined and sequenced to verify the identity of the mouse gene. Another way is to mine the mouse EST database to find the matching mouse sequences. This can be the basis for generating primer-pairs or specific mouse probes that allow an efficient screen of the mouse genomic libraries mentioned above by PCR or by hybridization. For the vast majority of genes the mouse homologue of the human gene retains the same biological function. The loss-of-function experiments in mice indicate the consequences of absence of expression of the gene on the phenotype of the mouse and the information obtained is applicable to the function of the gene in humans. On many occasions a specific phenotype observed in knock-out mice was similar to a specific human inherited disease and the gene was then proved to be involved and mutated in the human disease. While mice are specifically discussed herein as the knockout animal, those of ordinary skill in the art well understand that any other eukaryotic animal can be used in the same way as described for mice to make a corresponding knockout animal.

The transgenics and knock-outs of the present invention are constructed using standard methods known in the art and as set forth in U.S. Pat. Nos. 5,487,992, 5,464,764, 5,387,742, 5,360,735, 5,347,075, 5,298,422, 5,288,846, 5,221,778, 5,175,385, 5,175,384, 5,175,383, 4,736,866 as well as Burke et al (1991), Capecchi (1989), Davies et al (1992), Dickinson et al (1993), Duff et al (1995), Huxley et al (1991), Jakobovits et al (1993), Lamb et al (1993), Pearson et al (1993), Rothstein (1991), Schedl et al (1993), Strauss et al (1993). Further, patent applications WO 94/23049, WO 93/14200, WO 94/06908, WO 94/28123 also provide information.

More specifically, any techniques known in the art can be used to introduce the transgene expressibly into animals to produce the parental lines of animals. Such techniques include, but are not limited to, pronuclear microinjection (U.S. Pat. No. 4,873,191); retrovirus mediated gene transfer into germ lines (Van der Putten et al, 1985); gene targeting in embryonic stem cells (Thompson et al, 1989; Mansour, 1990 and U.S. Pat. No. 5,614,396); electroporation of embryos (Lo, 1983); and sperm-mediated gene transfer (Lavitrano et al, 1989). For a review of such techniques see Gordon (1989).

Further, one parent strain instead of carrying a direct human transgene can have the homologous endogenous gene modified by gene targeting such that it approximates the transgene. That is, the endogenous gene has been "humanized" and/or mutated (Reaume et al, 1996). It should be noted that if the animal and human sequence are essentially homologous a "humanized" gene is not required. The transgenic parent can also carry an over expressed sequence, either the non-mutant or a mutant sequence and humanized or not as required. The term transgene is therefore used to refer to all these possibilities.

Additionally, cells can be isolated from the offspring which carry a transgene from each transgenic parent and that are used to establish primary cell cultures or cell lines as is known in the art.

Where appropriate, a parent strain will be homozygous for the transgene. Additionally, where appropriate, the endogenous non-transgene in the genome that is homologous to the transgene will be non-expressive. By non-expressive is meant that the endogenous gene will not be expressed and that this non-expression is heritable in the offspring. For example, the endogenous homologous gene could be "knocked-out" by methods known in the art. Alternatively, the parental strain that receives one of the transgenes could carry a mutation at the endogenous homologous gene rendering it non-expressed.

XVIII. Promoters

As promoters and regulatory elements of the candidate genes in accordance with the present invention are also useful in the screening assays described in Section VIII, the present invention is also directed to the sequence of such promoters and/or other regulatory agents. Once the gene has been identified, it is within the routine skill in the art for one ordinary skill to identify the sequence of the promoter region or other regulatory regions. This may be accomplished as discussed below.

It is well recognized that promoters are generally located upstream of the coding sequence. There are numerous methods used conventionally in the art for determining a promoter region and portions of that region essential for promoter activity. For example, Kähäri et al (1990) made constructs in which a region from −2260 to −14 upstream of the ATG initiation codon of the human elastin gene was systematically truncated from −2260 towards −14 to create a set of nested deletions, all with the same −14 end point, which is linked to and controls the expression of a coding sequence for a reporter molecule (chloramphenicol acetyltransferase). The constructs are assayed for the expression of the reporter as a measure of the promoter activity of the truncated DNA fragments. Using this type of deletion analysis, Kähäri et al isolated a 497 bp fragment which provided maximal gene expression.

The above method is directed to locating the promoter region, as well as identifying the portions thereof essential for activity. Other mutagenesis techniques, such as linker scanning, which generate a series of clustered point mutations can also be used to fine map the sequence elements required for promoter function.

Although in a great majority of cases the 5'-flanking region is sufficient to promote gene expression, it has been reported that in some instances intron, or even the 3'-untranslated sequences, provide regulatory sequences that contribute to promoter activity. For example, intron I sequences were found to be important for high-level and tissue-specific expression of an alpha-skeletal actin gene, a beta-globin gene and a peripherin gene (Reecy et al, 1998; James-Pederson et al, 1995; Belecky-Adams et al, 1993). In view of these examples of introns or 3'-untranslated sequences contributing to promoter activity, promoter constructs (i.e., fused to reporter gene) may include intron I sequences of the candidate gene and, when necessary, 3'-untranslated sequences. In the former case, a DNA fragment can be isolated that spans the 5'-flanking region, the first exon and the first intron, followed by the reporter gene. The translation initiation codon of the candidate gene could also be mutated to avoid translation of truncated candidate gene product.

XIX. EXAMPLES

General Methods

Most of the techniques used in molecular biology are widely practiced in the art, and most practitioners are familiar with the standard resource materials which describe specific conditions and procedures. However, for convenience, the following paragraphs can serve as a guideline.

General methods in molecular biology: Standard molecular biology techniques known in the art and not specifically described were generally followed as in Sambrook et al (1989), and in Ausubel et al (1989), particularly for the Northern Analysis and in situ analysis and in Perbal (1988), and in Watson et al. Polymerase chain reaction (PCR) was carried out generally as in *PCR Protocols: A Guide To Methods And Applications*, Academic Press, San Diego, Calif. (1990).

Reactions and manipulations involving other nucleic acid techniques, unless stated otherwise, were performed as generally described in Sambrook et al (1989), and methodology as set forth in U.S. Pat. Nos. 4,666,828; 4,683,202; 4,801,531; 5,192,659 and 5,272,057 and incorporated herein by reference.

Additionally, in situ (In cell) PCR in combination with flow cytometry can be used for detection of cells containing specific DNA and mRNA sequences (Testoni et al, 1996).

General methods in immunology: Standard methods in immunology known in the art and not specifically described are generally followed as in Stites et al (1994) and Mishell et al (1980). Available immunoassays are extensively described in the patent and scientific literature. See, for example, U.S. Pat. Nos. 3,791,932; 3,839,153; 3,850,752; 3,850,578; 3,853, 987; 3,867,517; 3,879,262; 3,901,654; 3,935,074; 3,984,533; 3,996,345; 4,034,074; 4,098,876; 4,879,219; 5,011,771 and 5,281,521 as well as Sambrook et al (1989).

General Methods of the Invention

The general methods of the invention are generally as described in U.S. patent application Ser. No. 09/309,862 of same applicant which is by reference incorporated herein in its entirety.

In brief, U.S. Ser. No. 09/309,862 provides methods for identifying genes regulated at the RNA level by cue-induced gene expression. It relates to the rapid isolation of differentially expressed or developmentally regulated gene sequences through analysis of mRNAs obtained from specific cellular compartments and comparing the changes in the relative abundance of the mRNA in these compartments as a result of applying a cue to the tested biological samples. The cellular compartments include polysomal and non-polysomal fractions, nuclear fractions, cytoplasmic fractions and spliceosomal fractions. The method includes the steps of exposing cells or tissue to a cue or stimulus such as mechanical, chemical, toxic, pharmaceutical or other stress, hormones, physiological disorders or disease; fractionating the cells into compartments such as polysomes, nuclei, cytoplasm and splicesomes; extracting the mRNA from these fractions, and subjecting the mRNA to differential analysis using accepted methodologies, such as gene expression array (GEM).

The method is designed for identifying and cloning genes which are either up- or down-regulated responsive to a specific pathology, stress, physiological condition, and so on, and in general, to any factor that can influence cells or organisms to alter their gene expression.

Further in U.S. Ser. No. 09/309,862, an example is provided which shows the use of RNA isolation from nuclei for isolating genes whose steady state levels show only minor changes, but which show high differential expression when detected by nuclear RNA probe. Most such genes are regulated at the transcriptional level.

The specific mRNA of the invention is total cellular mRNA, and regulation is specifically on the transcriptional level.

In order to identify genes whose expression is either induced or reduced by hypoxia, the following experimental techniques were conducted.

Preparation of Custom Hypoxia-Specific Microarrays

The first step in identifying the genes of the present invention involves the preparation of a microarray containing genes which are suspected of either being induced by hypoxia after 16 hours, reduced by hypoxia after 16 hours, or induced by hypoxia after 4 hours, which genes are obtained either from the rat C6 glioma cell line or the human A172 glioma cell line.

In the preparation of such a microarray, each of the cell lines were exposed to hypoxic conditions (0.5% $O_2$ and 5% $CO_2$) for 4 or 16 hours and compared to cells grown under normal conditions (normoxia). Three enriched libraries were made by the suppression subtractive hybridization (SSH) method using the "PCR-Select cDNA subtraction kit" from CLONTECH. The subtractive libraries were made from the following sample:

1. 16 hours hypoxia vs. normal (genes induced by hypoxia after 16 hours).
2. normal vs. 16 hours hypoxia (genes reduced by hypoxia after 16 hours).
3. 4 hours hypoxia vs. normal (genes induced by hypoxia after 4 hours).

From library 1, 1000 colonies were grown, and the plasmids prepared in 96 well format. From libraries 2 and 3, 500 colonies were processed from each. Thus, a total of 2000 individual plasmids were prepared and used for the fabrication of a Gene Expression Microarray (GEM). For this, the inserts of each plasmid were amplified by PCR and robotically fabricated on the glass. cDNA chip printing was performed by Synteni (Wang et al, 1999)

Preparation of Probes for Microarray Hybridization

Isolated messenger RNA is labeled with fluorescent dNTP's using a reverse transcription reaction, using 50 µg template RNA (probes derived from nuclear RNA and total RNA), to generate a labeled cDNA probe. mRNA is extracted from either C6 or A172 cells cultured in normoxia conditions and labeled with Cy3-dCTP (Amersham) and mRNA extracted from C6 or A172 cells cultured under hypoxic conditions is labeled with Cy5-dCTP (Amersham). The two labeled cDNA probes are then mixed and hybridized onto microarrays (Schena et al, 1996; Wang et al, 1999). Following hybridization the microarray was scanned using a laser scanner and the amount of fluorescence of each of the fluorescence dyes was measured for each cDNA clone on the microarray giving an indication of the level of mRNA in each of the original mRNA populations being tested. Comparison of the fluorescence on each cDNA clone on the microarray between the two different fluorescent dyes is a measure for the differential expression of the indicated genes between the two experimental conditions.

The following probes were made from C6 and A172 for screening the GEM:

1. Normoxia (Cy3 labeled)+16 hours hypoxia (Cy5 labeled).

2. Normoxia (Cy3 labeled)+4 hours hypoxia (Cy5 labeled).

The following cDNA sequences of the present invention were found to be induced under hypoxic conditions.

In Situ Analysis:

In situ analysis is performed for the candidate genes identified by the differential response to exposure to hypoxic conditions as described above. The expression is studied in normal tissues and in pathological models as described herein.

Utilizing microarray hybridization the sequences set forth herein were identified and cloned as being differentially expressed under hypoxic conditions (see also Braren et al, 1997).

In parallel experiments Northern Analysis results and results obtained by the gene expression microarray analysis where found to coincide and either can be used to determine hypoxia-regulated response. As well in other experiments, the results from in situ analysis showed a high degree of correlation with the Northern Analysis and microarray analysis.

The sequences are listed that were found, the sequences are identified by clone number. In some cases either end of the clone has been sequenced for use or the entire clone sequence and protein sequence are provided.

Unigem1 (Syntheni) was utilized for screening of human glioma cell line A172 to identify genes whose expression is modified by hypoxia.

A Retinopathy Model:

Three major biological processes occur in nervous tissues under hypoxic conditions:
1. apoptotic death of hypoxia-damaged cells;
2. angiogenesis induced by factors secreted by hypoxia-suffering cells (a feedback control of oxygen concentration in tissue); and
3. secretion of neurotrophic and neuroprotective factors.

Therefore, it was assumed that among novel genes transcriptionally regulated by hypoxia in C6 and A172 glioma cells, there are those with pro- and antiapoptotic function as well as secreted neurotrophic, neuroprotective and angiogenic factors. It is worth noting, that regulation of apoptosis and angiogenesis is closely linked to cancerogenesis.

As initial step of biological characterization, candidate genes were tested for their ability to induce/protect cells from apoptosis, for neurotrophic activity and for angiogenic/anti-angiogenic activity.

Cell Culture

MCF7 Tet-off (Clontech) human epithelial breast carcinoma cells and their transfected derivatives were maintained in DMEM supplemented with 10% FCS, 2 mM L-glutamine, 20 U/ml penicillin, 20 μg/ml streptomycin, and 100 μg/ml neomycin. The transfectants were cultured in the presence of 1 μg of tetracycline per ml. For UV treatment, cells were irradiated with 100 Mj/cm$^2$ short wavelength UV (UV Crosslinker, Fisher) and then incubated at 37° C. for 24 hours. Cells were stained with 0.5% methylene blue in 50% ethanol.

Human umbilical vein endothelial cells (HUVEC) were grown in M199 medium supplemented with 20% FCS, 2 mM L-glutamine, 20 U/ml penicillin, 20 μg/ml streptomycin, 0.001 mg/ml Heparin, 0.1 mg/ml ECGS.

Expression Vectors and Transfection Methods pTet-Splice/95 flag construct was prepared by EcoRI/HindIII subcloning from pLPC flag into pTet-splice.

MCF7 Tet-off cells were transfected with pTet-Splice/95 Flag using lipofectamine reagent. Stable transfectants were obtained by cotranfection of 0.5 μg of a thymidine kinase hygromycin plasmid. Cells were selected with 100 μg per ml hygromycin in the presence of 2 μg per ml tetracycline in the medium. Clones were screened for tetracycline-sensitive HP95 expression by Northern blot.

Growth Rate Analysis

MCF7 cells and their HP95 transfectants were seeded at 10$^4$ cells per 35-mm-diameter dish with or without tetracycline. At daily intervals, cells were collected by trypsinization and counted. This experiment was done in triplicate.

Assessment of Cell Viability

The cell viability was estimated by the lactate dehydrogenase (LDH) leakage method using a Cytotoxicity Detection Kit (Molecular Biochemicals) according to the manufacturer's protocol. LDH activity was measured as the optimal density at 492 nm.

Ischemia

Ischemia was achieved by incubating cells in a glucose free medium in a humidified environment at 37° C. in a three gas incubator maintained at 5% $CO_2$ and 0.5% $O_2$ for 16 hours.

Oxidative Stress

MCF7 cells were treated by adding to complete medium freshly prepared hydrogen peroxide at the concentration of 1 mM for 24 hours.

Serum Starvation Experiment

MCF7 clones were plated at 10$^4$ cells in six-well plates in DMEM containing 10% FCS with or without tetracycline. The medium was replaced 72 hours later with medium containing 0.1% serum in the presence or absence of tetracycline. After 24 hours cell viability was measured.

Annexin V Apoptosis Assay

The MCF7 clones were seeded into 60 mm culture dishes (1×10$^5$ cells/dish) and were maintained in the presence or absence of tetracycline for 72 hours. The cells were collected by trypsinization, centrifuged and washed in phosphate-buffered saline (PBS). The cells were then resuspended in 200 μl of 1× binding buffer. The apoptotic cells were analyzed using a Annexin V apoptosis assay kit (ALEXIS Biochemicals) according to the manufacturer's protocol.

Western Blot Analysis

Cells were washed with phosphate-buffered saline, and lysed in lysis buffer containing 10 mM Tris-HCl, pH 7.4, 1% (v/v) Noidet P40, 0.1% (w/v) sodium deoxycholate, 0.1% (w/v) sodium deoxycholate, 0.1% (w/v) SDS, 0.15 M NaCl, and protease inhibitor cocktail (Boehringer Mannheim). The whole cell lysates were clarified by centrifugation at 12,000×g for 30 minutes. Lysates containing 30 μg of protein were fractionated by SDS-10% polyacrylamide gel and transferred onto membrane (Schleicher & Schuell). The blots were incubated with antibody specific for Bcl-2 (Transduction Laboratories) and with the second antibody for detection of Bcl-2 using the ECL detection system (Amersham).

Collection of Conditioned Medium

The MCF7 clones (1×10$^5$ cells/dish) were grown in HUVEC medium in the presence or absence of tetracycline for 72 hours. Cell-conditioned media were collected, centrifuged at 15,000×g for 10 minutes. HUVEC, MCF7 and PC12 cells were seeded into 6 wells culture dishes (3×10$^4$ cells/well) 72 hours later, the conditioned medium was added (1:1). After 24 hours cell viability was measured.

Middle Cerebral Artery Occlusion (MCAO) Stroke Model

The stroke model was implied in the stroke-prone spontaneously hypertensive rat strain. Occlusion was permanent and unilateral—by electrocoagulation of MCA. This led to focal brain ischemia at the ipsilateral side of brain cortex leaving the contralateral side intact (control). Experimental animals were sacrificed 1, 2, 4, 12, 24, 48 and 72 hours after the operation, respectively. Brains were removed, fixed in formalin, embedded into paraffin and coronal sections were performed for the further use in in situ hybridization with Hypoptin-specific riboprobes. VEGF- and PGK-specific riboprobes were used as positive controls.

In Situ Hybridization

Radioactive in situ hybridization was performed according to previously published protocol (Faerman et al, 1997) with slight modifications. Deparaffinized sections were heated in 2×SSC at 70° C. for 30 minutes, rinsed in distilled water and incubated with 10 mg/ml proteinase K in 0.2M Tris-HCl (pH7.4), 0.05 M EDTA at 37° C. for 20 minutes. After proteinase digestion, slides were postfixed in 4% paraformaldehyde in PBS (20 minutes), quenched in 0.2% glycine (5 minutes), rinsed in distilled water, rapidly dehydrated through graded ethanols and air-dried. The hybridization mixture contained 50% formamide, 4×SSC (pH 8.0), 1×Denhardt's, 0.5 mg/ml herring sperm DNA, 0.25 mg/ml yeast RNA, 10 mM DTT, 10% dextran sulfate and $2 \times 10^4$ cpm/l of [$^{35}$S]-UTP-labeled riboprobe. After application of the hybridization mixture, sections were covered with sheets of polypropylene film cut from autoclavable disposposal bags and incubated in humidified chamber at 65° C. overnight. After hybridization covering film was floated off in 5×SSC with 10 mM DTT at 65° C. and slides were washed at high stringency: 2×SSC, 50% formamide, 10 mM DTT at 65° C. for 30 minutes and treated with RNAse A (10 μg/ml) for 30 minutes at 37° C. The high stringency washing step was repeated and slides were next washed in 2×SSC and 0.1×SSC (15 minutes each) at 37° C. Then slides were rapidly dehydrated through ascending ethanols and air-dried. For autoradiography slides were dipped in Kodak NTB-2 nuclear track emulsion diluted 1:1 with double-distilled water and were exposed for 3 weeks in light-tight box containing dessicant at 4° C. Exposed slides were developed in Kodak D-19 developer, fixed in Kodak fixer and counterstained with hematoxilin-eosin.

Microphotographs were taken using Zeiss Axioscop-2 microscope equipped with Diagnostic Instruments Spot RT CCD camera.

The sequences of the invention, the methods used therewith and the utility of the present invention can be shown by the following non-limiting examples:

Example 1

92 (SEQ ID NO:1)

Northern Blot Analysis:

Gene 92 is found up-regulated after 16 hours of hypoxia. On Northern blots, it appears as a single 5 Kb transcript.

Cloning:

Several partial human cDNA clones corresponding to gene 92 were isolated from human A172 cDNA library. The length of available contig is 2212 bp and it contains an ORF potentially coding for a 437 amino acid (265-1576 bp) protein (SEQ ID NO:2). The putative initiating ATG codon is preceded by in frame stop codon.

Bioinformatic Analysis:

Similarity search with 92 cDNA sequence against the public databases have shown 60% similarity to unknown *Drosophila* DNA sequence (AC004283) and mainly encompasses the 3' UTR and a part of the coding sequence. The search against the protein public databases gave partial similarity to hypothetical *C. elegans* protein (1703624) (77% similarity and 46% Identity).

The 92 cDNA sequence contains a region of 55 nucleotides (336-390 bp) that is constituted of CGG repeats. On the level of amino acids it appears as a GGD/SFGG (SEQ ID NO:20) repeated unit (aa 24-44). Two of the isolated cDNA clones contain a 30 nucleotides in frame deletion within this region, indicating that the amount of repeats can be variable. Forty-four of these nucleotides form a strong stem and loop secondary structure. When 92 cDNA was in vitro translated, the obtained protein had much smaller size than expected (30 kD instead of 45 kD). This, means that the stem and loop structure formed right downstream to the putative initiation codon prevents the proper progression of ribosome and the initiation actually starts from the next in frame ATG located at position 820-822.

Example 2

95 (SEQ ID NO:3)

Identification of Gene 95 mRNA Induction Under Hypoxic Treatments cDNA microarray differential expression was performed in order to identify genes that were responsive to hypoxia in human A172 glioma cells. 95 mRNA levels were significantly elevated under hypoxia. Northern blot analysis was performed in order to verify these observations. The 95 mRNA levels (3.9 kb) were highly induced by hypoxia in A172 glioma cells. Human EST that contained a full-length cDNA was identified as the human 95 transcript (SEQ ID NO:3). By in vitro translation this cDNA gave rise to a protein product of 62 Kd (SEQ ID NO:4). The sequence is 480 aa corresponding to nucleotides 323-1762 of SEQ ID NO:3.

Figure 1:
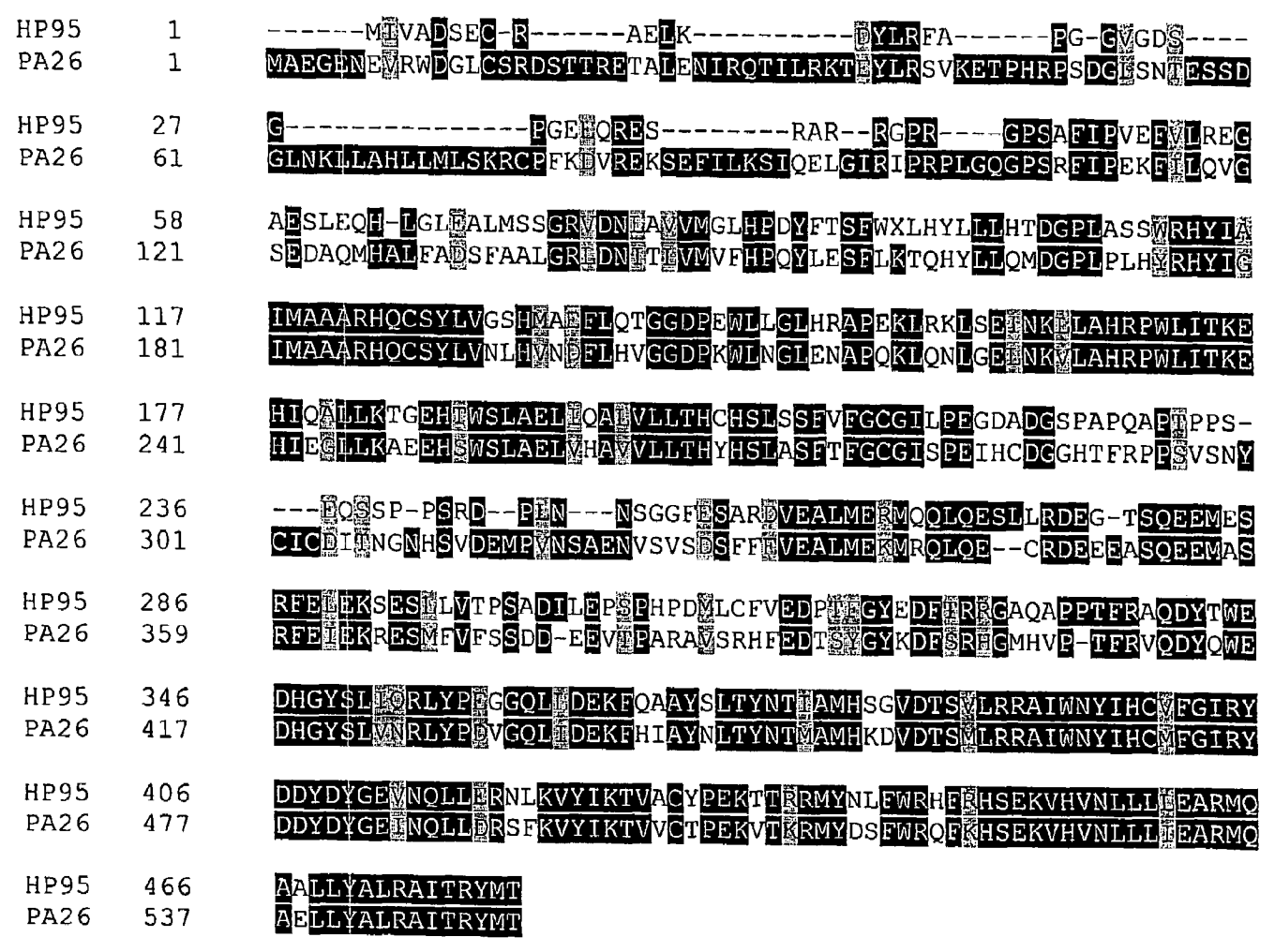

Gene 95 shares homology with the PA26 gene (FIG. 1). However, PA26 mRNA levels were not influenced by hypoxia in A172 cells (results not shown). Incubation of various cell lines from different origin (H1299, MCF7, Skov3) revealed high induction of 95 mRNA after 4 and 16 hours of hypoxic treatments (results not shown). p53 was not essential for the hypoxia-induced up-regulation, since 95 mRNA levels were increased during hypoxia, regardless of the p53 status of the cells.

The results from testing on a variety of cell lines prove that the hypoxia-induced up-regulation of expression of this gene is not limited to a specific cell line, but is found in a variety of cell lines. This confirms the expectation that such up-regulation will be found in any human cell subjected to hypoxia. Therefore, gene 95 and its encoded protein are excellent candidates for diagnostic testing of tissue or fluids for having been subjected to hypoxia, as described above.

Gene 95 mRNA was Up-Regulated Following DNA Damage in a p53 Dependent Manner

The effect of DNA damage on 95 mRNA was examined. Different cell lines were exposed to doxorubicin, a DNA-damaging agent that induces DNA breaks, or to UV radiation. 95 mRNA was strongly induced 24 hours after doxorubicin treatment in p53 wild type cells (MCF7, HEF and 293). In contrast, no induction was detected in p53-deficient cells (MDAH041, H1299). Similar results were obtained for cells exposed to UV radiation (data not shown). To verify the hypothesis on regulation of 95 by p53 under DNA-damage, MCF7 and their derivatives transduced with GSE56 (p53 dominant negative) were exposed to doxorubicin, UV radiation and hypoxia. GSE56 completely abrogated the induction of 95 by DNA-damaging agents, but did not affect its induction by hypoxia.

Inducible Expression of 95 in MCF7 Cells Revealed Delay in Their Growth Rate and Induced Apoptosis To permit conditional expression of a potential antiproliferative gene, human epithelial breast carcinoma MCF7 cells were stably transfected with a tetracycline-repressible vector containing flag-epitope-tagged 95. Two clones of MCF7 cells, which showed tetracycline-sensitive expression of 95 were obtained by Northern blot. To investigate how 95 overexpression affects the growth rate of proliferating breast tumor cells, the growth of the transfectant clones and control clones in the presence or absence of tetracycline was determined. As shown in FIG. 2, 95 overexpressing clones showed significant delay in growth compared with non-induced cells.

In order to determine whether this growth inhibition was due to 95-induced cell apoptosis, the 95 inducible clones were grown for 72 hours in the presence or absence of tetracycline. Overexpression of 95 resulted in cell apoptosis as determined by Annexin V apoptosis assay. Since it is known that Bcl-2 has a protective effect against apoptosis, its expression in MCF7-95 induced clones by Western analysis was tested. Dephosphorylated-Bcl-2 expression was induced in 95 overexpressing clones.

95 Induced DNA Damaged Apoptosis in MCF7 Cells

To find whether DNA damaged agents can stimulate apoptosis in 95 overexpressing cells, MCF7-95 inducible clones were treated with doxorubicin or exposed to UV irradiation in the presence or absence of tetracycline. Both stimuli induced apoptosis in >90% of the MCF7-95 expressing cells. Treatment with taxol, which is an antimicrotubule agent, revealed no difference between MCF7-95 inducible and control clones.

To investigate how 95 overexpression affects the response of proliferating breast tumor cells to mitogens, the response to serum-starved conditions (0.1% serum) was determined. Over-expression of 95 in MCF7 induced serum deprivation cell death, as was assessed by measuring lactate dehydrogenase (LDH) activity released from cells, by a spectrophometric method (FIG. 3).

Conditioned Medium from MCF7-95 Inducible Clones Promoted Cell Death

In order to determine whether MCF7-95 conditioned medium can stimulate apoptosis in other cells, conditioned medium was collected from MCF7-95 inducible clones that were grown in the presence or absence of tetracycline, and was added to human umbilical vein endothelial cells (HUVEC). After incubation of 24 hours, HUVEC cell death was measured. Conditioned medium from MCF7 clones overexpressing 95 promoted HUVEC cell death. The same phenomena was observed by adding the MCF7-95 conditioned medium to non-transfected MCF7 and PC12 cells.

Figure 4:
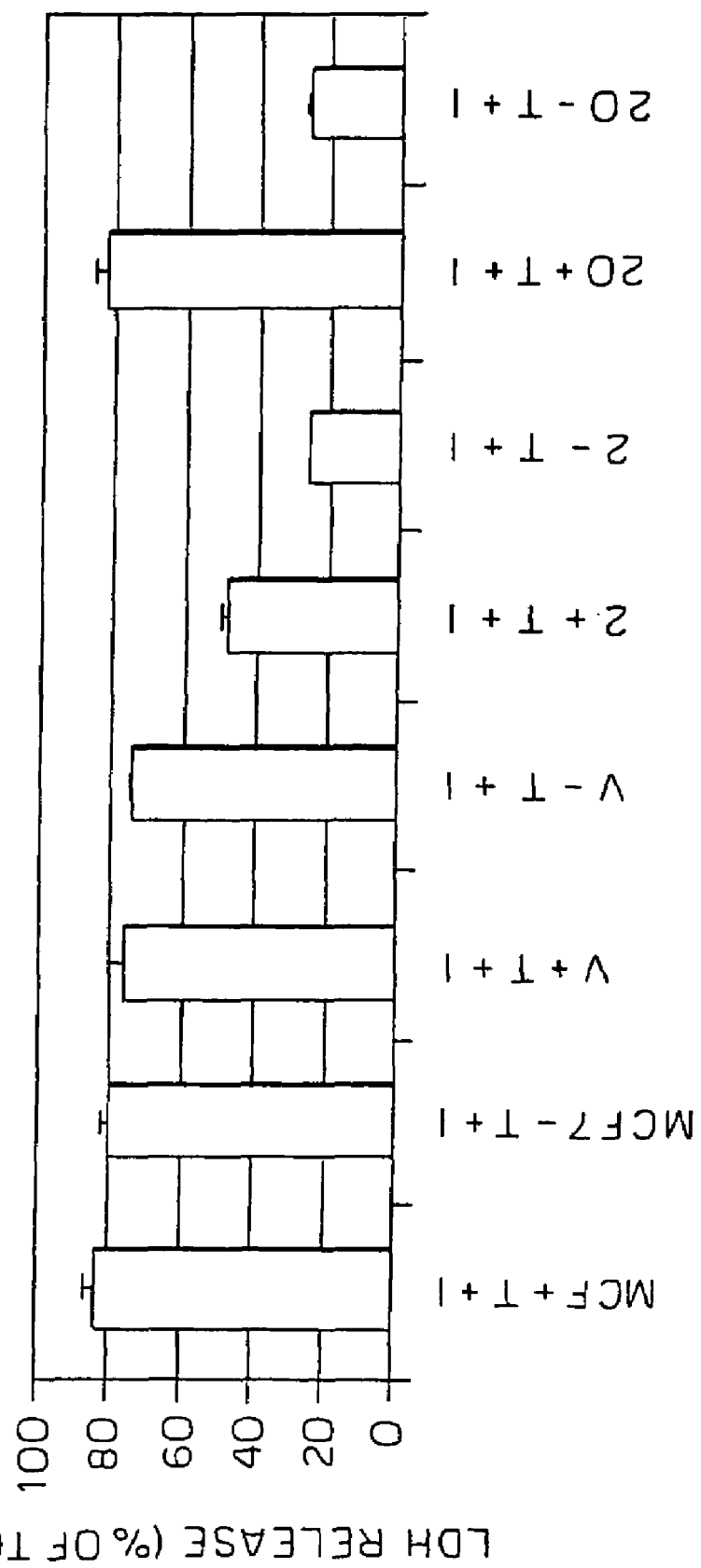
FIG. 4 is a graph showing the effects of 95 overexpression on protection of MCF7 cells against ischemia-induced cell death. T is tetracycline and I is ischemia.

95 Overexpression Protected MCF7 Cells Against Hypoxia and $H_2O_2$-Induced Cell Death To find the roles of 95 in hypoxia-induced cell death, the inducible clones were grown under ischemic conditions in the presence or absence of tetracycline. 95 overexpression protected MCF7 cells against hypoxia-induced cell death, as was assessed by measuring lactate dehydrogenase (LDH) activity released from cells (FIG. 4).

$H_2O_2$ is a natural product of metabolism, but at sufficient concentrations it produces cell damage. To demonstrate whether $H_2O_2$ induces apoptosis in MCF7-95 inducible clones, the cells were treated with 1 mM $H_2O_2$ for 24 hours. As shown in FIG. 5, 95 overexpression protected MCF7 cells against $H_2O_2$ induced apoptosis.

95 Expression was Up-regulated in the Brain of a Rat Model of Stroke

The $^{35}$S-labeled probe specific to the gene 95 was hybridized to coronal section of rat brains fixed at different time points (30 minutes, 1 hour, 2 hours, 4 hours, 12 hours, 24 hours, 48 hours, 72 hours) after permanent middle cerebral artery occlusion (MCAO). Results of this in situ hybridization study revealed the expression of the gene 95 at 12 and 24 hours after MCAO. Hybridization signal located to the subset of neurons in the transitional zone between the ischemic core and peri-infarct area.

95 Expression was Up-Regulated in Tumors (Not Necessarily Human)

Sections of tumors grown from C6 glioma cells in nude mice were hybridized to $^{35}$S-labeled riboprobe specific to the gene 95. Results of in situ hybridization demonstrated expression of the 95 gene in tumor cells surrounding necrotic areas. This pattern of expression closely resembles that of the VEGF revealed by hybridization of the corresponding probe to the parallel sections. These results suggest activation of the gene 95 expression in hypoxic areas within growing tumors.

Discussion

HIF-1 is a major regulator of the adaptation of the cells to hypoxic conditions. As observed with ES cells, this transcription factor is necessary to maintain cell proliferation in hypoxia (Iyer et al, 1997). However, HIF-1 is also involved in apoptosis in ES cells (Carmeliet et al, 1998). In hypoxia, HIF-1α is stabilized and is able to interact with p53. This interaction leads to stabilization and increased cellular p53, which, however, inhibits HIF-1α activity (Blagosklonny et al, 1998; An et al, 1998). Coexpression of HIF-1α and wild-type p53 leads to the inhibition of the HIF-1-induced transactivation (Blagosklonny et al, 1998). The dual role of HIF-1 as a necessary factor in survival to hypoxic stresses, but also as a pro-apoptotic protein, is not clear.

A novel p53 target gene, 95 has been isolated and characterized. It shares homology with PA26, a member of the GADD family. 95 is up-regulated and induces DNA damaged apoptosis in a p53 dependent manner. In contrast, 95 is up-regulated and protects MCF7 cells against ischemia and $H_2O_2$-induced cell death.

Hydrogen peroxide ($H_2O_2$) has been known to activate the mitochondrial permeability transition pore and the release of the mitochondrial protein cytochrome c (Stridh et al, 1998; Sugano et al, 1999). In the cytosol, cytochrome c in combination with Apaf-1 activates caspase-9, which then finally leads to activation of caspase-3 and apoptosis (Hampton et al, 1997). Caspases are evolutionarily conserved executioners of programmed cell death in normal development and are also implicated in a variety of pathological conditions, including cerebral ischemia (Nicholson et al, 1997). A recent study provides in vitro and in vivo evidence that a family of caspases plays a pivotal role in the hypoxia- and ischemia-induced death of oligodendrocytes (Shibata et al, 2000). The present results suggest that 95 is up-regulated by hypoxia, brain ischemia and $H_2O_2$, and that it plays a suppressive role in ischemia- and $H_2O_2$-induced apoptosis. Further investigation will be necessary to determine whether caspases are involved in 95 apoptotic machinery.

Bcl-2, a 26-kDa membrane-anchored proto-oncoprotein, was the first gene product discovered as an apoptosis suppressor acting in various cells (Reed et al, 1994). After cerebral ischemia, Bcl-2 is induced in surviving neurons (Clark et al, 1997), suggesting its protective effect on ischemic brain injury. Overexpression of Bcl-2 by gene transfer or in transgenic mice reduces the volume of infarction after cerebral ischemia (Martinou et al, 1994; Lawrence et al, 1996). Two mechanisms can be involved in the pro-survival effect of Bcl-2 against ischemic insults. The first is the anti-apoptotic effect of Bcl-2 and the second is its function as an antioxidant (Hockenbery et al, 1993). Recently, it was shown that ischemic insults dephosphorylated Bcl-2 in a time-dependent fashion without affecting the total amount of protein, and suggested that dephosphorylation of serine 70 is one of the critical factors in decreasing the anti-apoptotic function of Bcl-2 (Itakura et al, 2000). The present results show that overexpression of 95 in MCF7 cells induces dephosphorylated-Bcl-2 expression, and suggest that dephosphorylation of Bcl-2 may be involved in 95-induced apoptosis.

Several previous studies have implicated GADD153 expression in the mechanism of growth arrest and apoptosis (Barone et al, 1994; Chen et al, 1996). Introduction of GADD153 gene into gastric cancer cells can modulate sensitivity to anticancer agents in association with apoptosis (Kim et al, 1999). Furthermore, loss of GADD 153 gene expression leads to high genetic instability of oral melanoma cells (Korabiowska et al, 1999). In this study, it was shown that introduction of 95 gene into human epithelial breast carcinoma MCF7 cells can modulate their sensitivity to the anticancer agent doxorubicin. 95 has been mapped to 1p34-35 (HTGS), a part of chromosome 1 frequently deleted in high stage neuroblastoma tumors and sporadic breast tumors (Jogi et al, 2000; Phelan et al, 1996). Future mutations analysis of 95 in neuroblastoma and breast tumor samples will answer whether 95 is likely to be involved in the genesis of these tumors.

GADD153 and 95 could possess functions analogous to traditional stress-response genes, serving to protect cells from stress-induced damage and/or aiding the recovery of normal cellular functions following stress. One way in which p53 is thought to potentiate genomic stability, and consequently inhibit tumorigenesis is the removal of damaged cells through the triggering of apoptosis via transcriptional induction of genes that encode proapoptotic factors, such as 95. This study suggests that 95 induces DNA damage mediated apoptosis in a p53 dependent manner and protects against oxidative stress mediated apoptosis in a p53 independent mechanism. The identification of key events in the apoptotic pathway that are affected by cellular responses, such as the expression of 95, could facilitate the identification of targets for the manipulation of this protein, which may have important medical implications.

Accordingly, it is clear that 95 is a good gene and has all of the utilities discussed herein for good genes. Promotion of apoptosis in DNA damaged cells is also a beneficial property. Thus, administration of the 95 gene product to the site of a hypoxic event will help to ameliorate the undesirable effects of such an event.

Example 3

98 (SEQ ID NO:5)

Northern Blot Analysis:

Expression of gene 98 is strongly up-regulated by hypoxia already after four hours of exposure. On Northern blots, it appears as a single mRNA species of 4.4. Kb.

Cloning:

A full-length 98 cDNA was cloned. It is 4138 bp long and contains an single ORF encompassing the nucleotides 204-1445. The putative protein is 414 amino acids long.

Bioinformatic Analysis:

Search of the public databases revealed that 98 encoded protein is similar to two other human proteins: (1) a putative protein encoded by anonymous human 24945 mRNA sequence (AF131826) and (2) VDUP1 (protein induced in HL-60 cells by dihydroxy vitamin D3 treatment) (S73591). No significant structural features were found by existing protein analysis tools within the 98 putative protein.

It was previously demonstrated that treatment with vitamin D3 can induce apoptosis in C6 rat glioma cells (Baudet et al, 1996). Therefore, the relationship between the vitamin D-induced cell killing and 98 gene expression and function in glioma cells was studied.

The mammalian 98 expression vector was then prepared and its effects studied.

Example 4

60F6 (SEQ ID NO: 6)

Northern Blot Analysis:

Expression of this gene is moderately up-regulated after 16 hours of hypoxia. On Northern blot, it appears as a single 3.0 Kb species.

Cloning:

A complete 60F6 human cDNA clone was isolated from A172 cDNA library. The contig is 2675 bp long and contains a single ORF (bp 134-866) able to code for a putative protein of 244 amino acids (SEQ ID NO:7).

Bioinformatic Analysis:

A similarity search against the public databases revealed that the N-terminal half of 60F6 sequence exactly corresponds to a human cDNA coding for RhoE/Rho8 small GTP-binding protein (P52199, HSRHO8GRN). The identity of gene 60F6 was not determined before, because the small sequenced fragment that was initially possessed, originated from the Rho8 long 3' UTR. All the sequence information available in public databases did not include the long 3' UTR of Rho8. Structurally, Rho8 belongs to a family of Ras-related GTPases that regulate the actin cytoskeleton. However, this protein is unique in that it is constitutively active: GTPase deficient and in vivo farnesylated (Foster et al, 1996). Therefore, it is intriguing to find that this constitutively active G-protein is regulated on the level of transcription. Hypoxia regulation of Rho8 was not previously described.

Example 5

648 (lysyl hydroxylase 2) (SEQ ID NO:8, 10 and 12)

Northern Analysis

Probe 648 has detected a single 3.8 Kb transcript on Northern blots. Expression was induced in C6 glioma cells already after 4 hours of hypoxia.

Cloning

After extension of initial cDNA probe by RACE it became evident that identified rat sequence (SEQ ID NO:8), encoding a 758 aa of SEQ ID NO:9, is able to code for protein that represents a rat homologue of human lysyl hydroxylase 2 (PLOD2). The full-length open reading frames were cloned for both human (SEQ ID NO:10) and rat (SEQ ID NO:12) lysyl hydroxylase 2 homologues (by PCR, using primers built on the basis of known sequence, for human variant, and degenerative primers, for rat variant). The encoded proteins (SEQ ID NOs:11 and 13, respectively) have well defined signal peptides.

Bioinformatics Data

The cloned rat 648 cDNA contains an ORF coding for a putative protein that is 88% identical to the published human PLOD2 sequences. The least conserved sequences are within the signal peptide, however its functional features are completely preserved. The cloned human cDNA is almost identical to published human PLOD2 sequence. The word "almost" in the previous sentence stems from the fact that both in human and in rat cDNA species cloned in the inventors' laboratory a stretch of amino acids between positions 501-521 of published sequence PLOD2 sequence was absent. Therefore, the present PLOD2 variants are differentially spliced. Both rat and human homologues were amplified from RNA extracted from glioma cell lines cultured in hypoxic conditions.

Literature Review

Lysyl hydroxylases are the enzymes that catalyze the formation of hydroxylysine in collagens and other proteins with collagen-like amino-acid sequences, by the hydroxylation of lysine residue in X-K-G sequences. The hydroxylysine residues have two important functions: (1) serve as sites of attachment of carbohydrate units, and (2) they are essential for the stability of the intermolecular collagen crosslinks. Congenital deficiency of lysyl hydroxylase in humans leads to increased solubility of collagens and, consequently, to numerous defects in organization of connective tissue in various organs. There are three known isoforms of lysyl hydroxylase, encoded by different genes. In humans, PLOD2 was found to be highly expressed in pancreas, skeletal muscle, heart and placenta (by Northern blot). Nothing is known either about the regulation of PLOD2 expression by hypoxia or about its involvement in angiogenesis and tumorigenesis. Induction of PLOD2 by hypoxia can probably account for hypoxia-induced tissue fibrosis. Indeed, specific lysyl hydroxylase inhibitor, minoxidil, was able to suppress both cellular collagen production and fibroblasts proliferation (Murad et al, 1987; Saika et al, 1995). There were suggestions in literature to use modified lysyl hydroxylase inhibitor for treatment of vitreoretinopathy (Handa et al, 1993).

Analysis of Alternatively Spliced Versions of Gene 648

In order to establish whether the observed alternative splicing of PLOD2 is regulated by hypoxia, a set of PCR primers were synthesized that flank the alternatively spliced region. The expected sizes of RT-PCR products are: 216 bp, for published sequence and 156 bp, for the present sequence. Semi-quantitative RT-PCR was performed on RNA template extracted from human glioma A172 cell culture in either normoxia or in hypoxia for 4 and 16 hours. The obtained results clearly demonstrate that both PLOD2 forms are hypoxia regulated, but the form of the invention appears only in hypoxic conditions.

Testing Potential Pro- and Antiapoptotic Activity in Transient Transfection Assays pcDNA3-648 was transiently co-transfected together with pcDNA3-GFP in Hela and 293 cells. 24 and 48 hours later the cells were fixed and stained with DAPI. No apoptotic effect was observed in the transfected cells. In order to evaluate the anti-apoptotic properties of the 648 protein, a co-transfection assay was conducted using the pcDNA3-GFP and the FAS plasmids. No anti-apoptotic effect was observed.

Obtaining Stable Cell Clones Overexpressing 648 cDNA

C6 were stably transfected with 5 μg of the pcDNA3-648 plasmid. Following G418 selection the level of expression was measured using Northern blot analysis in comparison to its level in C6 cells after 16 hours under hypoxic conditions. Out of 18 independent clones from the pcDNA3-648 transfection, no one was positive.

In Situ Hybridization Analysis

Retinopathy Model

Probe 648 demonstrates clear hybridization signal throughout the inner nuclear layer of "hypoxic" pup's retina while "normoxic" retina is negative for the expression. No hybridization signal was detected in adult retina.

In mouse embryo sections hybridization signal was detected in some apoptotic cells in the roof of the fourth brain ventricle and in developing retina ganglia, where expressing cells had no apoptotic features.

Multi-tissue block hybridization shows expression of 648 gene (rat PLOD2) in visceral smooth muscles in oviduct, uterus, stomach and intestine. Vascular smooth muscles do not display hybridization signal.

The most prominent cell type hybridizing to 648 probe in the ovary are granulosa cells of larger secondary follicles. No hybridization signal is detected in granulosa cells of primary and small secondary follicles. Significantly, hybridization signal is weakened in postovulatory follicles and completely disappears in corpora lutea. This shows that expression in granulosa cells is established at later stages of follicular maturation and it is abruptly down-regulated upon ovulation and the onset of conversion into lutein cells. On the other hand, follicular involution is not accompanied by the changes in 648 expression since strong hybridization signal is preserved in granulosa cells of atretic follicles.

Weak hybridization signal can be seen in some stromal cells surrounding large secondary follicles and corpora lutea as well as in cells of theca internal of secondary follicles. Prominent signal is found in "interstitial glands". This shows distinct regulation of 648 expression in theca cells undergoing "luteinization" in different locations: it is down regulated in corpora lutea but preserved or even up-regulated in interstitial glands.

As to the germinal cells, an oocyte that expresses 648 was found only in one primary follicle while many other primary and secondary follicles had no hybridization signal. This shows a transient expression of 648 in oocytes at some stage of their development.

Discrepancy in the hybridization patterns of human (published) and rat PLOD2 (648) genes is explained by different sensitivities of different detection methods (Northern blot vs. in situ hybridization). The rat probe used in the present invention does not span an alternatively spliced region.

Example 6

24D4 (SEQ ID NO:14)

Northern Blot Analysis

Expression of gene 24D4 is down-regulated after 16 hours of hypoxia. On Northern blots, it appears as a single 1.5 Kb mRNA species.

Cloning

A partial 24D4 human cDNA clone was isolated from A172 cDNA library. The available sequence is 1486 bp long and contains an N-terminal truncated ORF (bp 1-396), encoding the peptide of SEQ ID NO:15.

Bioinformatic Analysis

The sequence has no analogs in public databases. The available protein sequence contains three consequent Zn-finger motifs, all of $C_2H_2$ type (aa 52-72, 80-100 and 108-128). Zinc finger domains of this type are usually found in nucleic acid-binding proteins.

Example 7

77H4 (SEQ ID NO:16)

Northern Blot Analysis

Expression of gene 77H4 is up-regulated after 16 hours of hypoxia. On Northern blots, it appears as a single mRNA species 0.6-0.7 Kb in size.

Cloning

Several EST cDNA clones from public databases, corresponding to clone 77H4, were sequenced. All clones possess a poly A tail and a polyadenylation signal at their 3' end.

Bioinformatic Analysis

Gene 77H4 (SEQ ID NO:16) encodes a 360 bp protein (SEQ ID NO:17). An exhaustive search was performed of public databases for all 77H4-related sequences. Several independent contigs were identified in TIGR THC database. All of them are not completely identical to one another and contain nucleotide deletions of various length. This shows a certain variability in 77H4 nucleotide sequence.

Recently, a novel steroid receptor transcriptional coactivator, SRA, was found to be present as an RNA molecule in the transcription activating complex SRC-1 (Lanz et al, 1999). Although no similarity was found between clone 77H4 and SRA RNA on the sequence level, several characteristic features seem to be shared by both sequences:

both mRNAs, 77H4 and SRA, are approximately of the same size—0.7 Kb;
sequencing multiple cDNA clones corresponding to either mRNA revealed extensive variability in certain regions;
hybridization signals of both mRNA, therefore, appear as fuzzy bands on Northern blots;
neither mRNA exhibit characteristics of protein.

Therefore, the 77H4 cDNA clone has similar to SRA function and can serve a coactivator in some transcriptional complexes.

Example 8

14G2 (SEQ ID NO:18)

Northern Blot Analysis

Expression of gene 14G2 is regulated within 16 hours of hypoxia. On Northern blots, it appears as a single mRNA species.

Cloning

A partial 14G2 human cDNA clone was isolated. The available sequence was then characterized and cloned as shown in SEQ ID NO:18.

Example 9

29F3 (SEQ ID NO:19)

Northern Blot Analysis

Expression of gene 29F3 is regulated within 16 hours of hypoxia. On Northern blots, it appears as a single mRNA species.

Cloning

A partial 29F3 human cDNA clone was isolated. The available sequence was then characterized and cloned as shown in SEQ ID NO:19.

Throughout this application, various publications, including United States patents, are referenced by author and year and patents by number. Full citations for the publications are listed below. The disclosures of these publications and patents in their entireties are hereby incorporated by reference into this application in order to more fully describe the state of the art to which this invention pertains.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the described invention, the invention can be practiced otherwise than as specifically described.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention. Thus the expressions "means to . . . " and "means for . . . ", or any method step language, as may be found in the specification above and/or in the claims below, followed by a functional statement, are intended to define and cover whatever structural, physical, chemical or electrical element or structure, or whatever method step, which may now or in the future exist which carries out the recited function, whether or not precisely equivalent to the embodiment or embodiments disclosed in the specification above, i.e., other means or steps for carrying out the same functions can be used; and it is intended that such expressions be given their broadest interpretation.

The sequence list attached hereto is hereby incorporated by reference.

REFERENCES

Abe et al, "Specific inhibition of influenza virus RNA polymerase and nucleoprotein gene expression by liposomally encapsulated antisense phosphorothioate oligonucleotides in MDCK cells", *Antivir Chem Chemother* 9:253-262 (1998)

Adams et al, "Complementary DNA sequencing: expressed sequence tags and human genome project", *Science* 252 (5013):1651-1656 (1991)

Agrawal S, "Antisense oligonucleotides: towards clinical trials", *Trends Biotechnol* 14(10):376-387 (1996)

An et al, "Stabillization of wild-type p53 by Hypoxia-Inducible Factor-1α", *Nature* 392:405-408 (1998)

Anazodo et al, "Relative levels of inhibition of p24 gene expression by different 20-mer antisense oligonucleotide sequences targeting nucleotides +1129 to +1268 of the HIV-1 gag genome: an analysis of mechanism", *Biochem Biophys Res Commun* 229(1):305-309 (1996)

Ausubel et al, *Current Protocols in Molecular Biology*, John Wiley and Sons, Baltimore, Md. (1989)

Ausubel et al (Eds), *Current Protocols in Molecular Biology*, John Wiley & Sons, Inc. (New York, 1994-2000)

Bai et al, "Gene transfer to vein graft wall by HVJ-liposome method: time course and localization of gene expression", *Ann Thorac Surg* 66:814-819 (1998)

Barone et al, "CHOP (GADD153) and its oncogenic variant, TLS-CHOP, have opposing effects on the induction of G1/S arrest", *Genes Dev* 8(4):453-464 (1994)

Batchvarova et al, "Inhibition of adipogenesis by the stress induced protein CHOP (gadd 153)", *EMBO J.* 14:4654-4661 (1995)

Baudet et al, "1,25-Dihydroxyvitamin D3 induces programmed cell death in a rat glioma cell line", *J Neurosci Res* 46(5):540-550 (1996)

Belecky-Adams et al, "Intragenic sequences are required for cell type-specific and injury-induced expression of the rat peripherin gene", *J Neurosicence* 13:5056-5065 (1993)

Blagosklonny et al, "p53 inhibits Hypoxia-Inducible Factor-stimulated transcription", *J Biol Chem* 273:11995-11998 (1998)

Bochot et al, "Liposomes dispersed within a thermosensitive gel: a new dosage form for ocular delivery of oligonucleotides", *Pharm Res* 15:1364-1369 (1998)

Borrebaeck, *Antibody Engineering—A Practical Guide*, W.H. Freeman and Co., 1992

Bouck et al, "How tumors become angiogenic", *Adv Cancer Res* 69:135-174 1(996).

Boutin et al, "Identification of a cDNA encoding a long form of prolactin receptor in human hepatoma and breast cancer cells," *Molec Endocrinol* 3(9):1455-1461 (1989)

Braren et al, "Use of the EST database resource to identify and clone novel mono(ADP-ribosyl)transferase gene family members", *Adv Exp Med Bio* 419:163-168 (1997).

Braun et al, "A novel human muscle factor related to but distinct from MyoD1 induces myogenic conversion in 10T1/2 fibroblasts", *EMBO J.* 8(3):701-709 (1989)

Bunn et al, "Oxygen sensing and molecular adaptation in hypoxia", *Physiol Rev* 76:839-885 (1996).

Burke et al, "Preparation of Clone Libraries in Yeast Artificial-Chromosome Vectors" in *Methods in Enzymology*, Vol. 194, *Guide to Yeast Genetics and Molecular Biology*, eds. Guthrie et al, Academic Press, Inc., Chap. 17, pp. 251-270 (1991).

Cao et al, "Lymphotactin gene-modified bone marrow dendritic cells act as more potent adjuvants for peptide delivery to induce specific antitumor immunity", *J Immunol* 161:6238-6244 (1998)

Calabretta et al, "Antisense strategies in the treatment of leukemias", *Semin Oncol* 23:78 (1996)

Cantor et al, "Ribozyme cleaves rex/tax mRNA and inhibits bovine leukemia virus expression", *Proc Natl Acad Sci*, 90(23):10932 (1993)

Capaccioli et al, "Cationic lipids improve antisense oligonucleotide uptake and prevent degradation in cultured cells and in human serum", *Biochem Biophys Res Comm* 197:818-825 (1993)

Capecchi M R, "Altering the genome by homologous recombination" *Science* 244:1288-1292 (1989).

Carmeliet et al, "Role of HIF-1alpha in hypoxia-mediated apoptosis, cell proliferation and tumor angiogenesis", *Nature* 394(6692):485-490 (1998)

Chan et al, "Molecular cloning and localization to chromosome 6 of mouse INT1L1 gene", *Somatic Cell Molec Genet* 15(6):555-562 (1989)

Chen et al, "Inhibition of HIV-1 replication by novel multi-target ribozymes", *Ann NY Acad Sci* 660:271-273 (1992)

Chen et al, "Down-regulation of gadd153 by c-myc in rat fibroblasts and its effect on cell growth and radiation-induced apoptosis", *Oncogene* 13(8):1659-1665 (1996)

Clark et al, "Apoptosis-suppressor gene bcl-2 expression after traumatic brain injury in rats", *J Neurosci* 17: 9172-9182 (1997)

Crooke S T, "Progress in antisense therapeutics", *Hematol Pathol* 2:59 (1995)

Croyle et al, "Development of a highly efficient purification process for recombinant adenoviral vectors for oral gene delivery", *Pharm Dev Technol* 3(3)365-372 (1998)

Daniel et al, "Retroviral transfer of antisense sequences results in reduction of C-Abl and induction of apoptosis in hemopoietic cells", *J Biomed Sci* 5:383-394 (1998)

Davies et al, "Targeted alterations in yeast artificial chromosomes for inter-species gene transfer", Nucleic Acids Research, Vol. 20, NO 11, pp. 2693-2698 (1992).

Davis et al (eds.), *Basic Methods in Molecular Biology*, Elsevier Press, NY (1986)

Dickinson et al, "High frequency gene targeting using insertional vectors", *Human Molecular Genetics*, 2(8)1299-1302 (1993)

Dor et al, "Ischemia-driven angiogenesis", *Trends Cardiovasc Med* 7:289-294 (1997)

Duff et al, "Insertion of a pathogenic mutation into a yeast artificial chromosome containing the human APP gene and expression in ES cells", *Research Advances in Alzheimer's Disease and Related Disorders*, 1995.

Duke et al, "Cell Suicide in Health and Disease", *Sci Am* 275(6):80-87 (1996)

Eckstein F, "Nucleoside Phosphorothioates", *Ann Rev Biochem* 54:367-402 (1985)

Edinger et al, "Use of GPR1, GPR15, and STRL33 as coreceptors by diverse human immunodeficiency virus type 1 and simian immunodeficiency virus envelope proteins", *Virology* 249:367-378 (1998)

Faerman et al, "Transgenic mice: production and analysis of expression", *Methods Cell Biol* 52:373-403 (1997)

Fang et al, "A packaging system for SV40 vectors without viral coding sequences", *Anal Biochem* 254:139-143 (1997)

Felgner P L, "Nonviral Strategeies for Gene Therapy", *Sci Am*, 276(6):102-106 (1997)

Flanagan W M, "Antisense comes of age", *Cancer Metastasis Rev*, 17(2):169-176 (1998)

Fleming et al, "The effects of nutrient deprivation and differentiation on the expression of growth arrest genes (gas and gadd) in F9 embryonal carcinoma cells", (1998) 330:573-579 (1998)

Forance et al, "Mammalian genes coordinately regulated by growth arrest signals and DNA-damaging agents", *Mol Cell Biol* 9:4196-4203 (1989)

Foster et al, "Identification of a novel human Rho protein with unusual properties: GTPase deficiency and in vivo farnesylation", *Mol Cell Biol* 16(6):2689-2699 (1996)

Galizzi et al, Molecular cloning of a cDNA encoding the human interleukin 4 receptor", *Int Immunol* 2(7):669-675 (1990)

Gennaro A R (ed.), *Remington's Pharmaceutical Sciences*, Mack Publishing Company, Easton, Pa., 1990, pp 1521-1712

Gerster et al, "Quantitative analysis of modified antisense oligonucleotides in biological fluids using cationic nanoparticles for solid-phase extraction", *Anal Biochem* 262: 177-184 (1998)

Gewirtz "Oligodeoxynucleotide-based therapeutics for human leukemias", *Stem Cells Dayt* 11:96 (1993)

Gordon et al, 1989

Gould et al, "Use of the DNA polymerase chain reaction for homology probing: isolation of partial cDNA or genomic clones encoding the iron-sulfur protein of succinate dehydrogenase from several species", *Proc Nat Acad Sci USA* 86(6):1934-1938 (1989)

Graeber et al, "Hypoxia-mediated selection of cells with diminished apoptotic potential in solid tumours", *Nature* 379(6560):88-91 (1996)

Griscelli et al, "Heart-specific targeting of beta-galactosidase by the ventricle-specific cardiac myosin light chain 2 promoter using adenovirus vectors", *Hum Gene Ther,* 9:1919-1928 (1998)

Guang-Lin et al, "Adenovirus-mediated gene transfer of CTLA41G gene results in prolonged survival of heart allograft", *Transplant Proc,* 30:2923-2924 (1998)

Guinot et al, "Antisense oligonucleotides: a new therapeutic approach", *Pathol Biol,* 46:347-354 (1998)

Gutkowska et al, "Circulating forms and radioimmunoassay of atrial natriuretic factor", *Endocrinol Metab Clin North Am* 16(1):183-198 (1987)

Hampel et al, "RNA catalytic properties of the minimum (−)sTRSV sequence", *Biochemistry* 28(12):4929-33 (1989)

Hampton et al, "Dual regulation of caspase activity by hydrogen peroxide: implications for apoptosis", *FEBS Lett* 14: 552-556 (1997)

Hanania et al, "Recent advances in the application of gene therapy to human disease", *Am J Med* 99:537 (1995)

Hanahan et al, "Patterns and Emerging Mechanisms of Angiogenic Switch During Tumorigenesis"; *Cell* 86:353-364 (1996)

Handa et al, "Minoxidil inhibits ocular cell proliferation and lysyl hydroxylase activity", *Invest Ophthalmol Vis Sci* 34(3)567-575 (1993)

Harlow et al, *Antibodies: A Laboratory Manual*, Cold Spring Harbor Laboratory, Cold Spring Harbor, N.Y., (1988)

He et al, "Molecular cloning of androgen receptors from divergent species with a polymerase chain reaction technique: complete cDNA sequence of the mouse androgen receptor and isolation of androgen receptor cDNA probes from dog, guinea pig and clawed frog", *Biochem Biophys Res Comm* 171(2):697-704 (1990)

Hemmi et al, "The presence of human coxsackievirus and adenovirus receptor is associated with efficient adenovirus-mediated transgene expression in human melanoma cell cultures", *Hum Gene Ther* 9:2363-2373 (1998)

Herskowitz I, "Functional inactivation of genes by dominant negative mutations", *Nature* 329(6136):219-222 (1987)

Higuti et al, "Molecular cloning of cDNA for the import precursor of human subunit B of H(+)-ATP synthase in mitochondria", *Biochem Biophys Res Comm* 178(3):1014-1020 (1991)

Hockenbery et al, "Bcl-2 functions in an antioxidant pathway to prevent apoptosis", *Cell* 75:241-251 (1993)

Hofmann et al, "Rapid retroviral delivery of tetracycline-inducible genes in a single autoregulatory cassette", *Proc Natl Acad Sci* 93(11):5185-5190 (1996)

Hollander et al, "Analysis of the mammalian gadd45 gene and its response to DNA damage", *J Biol Chem* 268:24385-24393 (1993)

Hsieh et al, "Chromosome localization and cDNA sequence of murine and human genes for ras p21 GTPase activating protein (GAP)," *Somat Cell Mol Genet* 15(6):579-590 (1989)

Huston et al, "Protein engineering of single-chain Fv analogs and fusion proteins" in Methods in Enzymology (J J Langone, ed.; Academic Press, New York, N.Y.) 203:46-88 (1991)

Huxley et al, "The human HPRT gene on a yeast artificial chromosome is functional when transferred to mouse cells by cell fusion", *Genomics* 9:742-750 (1991)

Imamura et al, "Molecular cloning and primary structure of rat thyroxine-binding globulin", *Biochemistry* 30(22): 5406-5411 (1991)

Itakura et al, "Both HPV and carcinogen contribute to the development of resistance to apoptosis during oral carcinogenesis", *Int J Oncol* 16(3):591-597 (2000)

Iwata et al, "Structure of the mouse tyrosine hydroxylase gene", *Biochem Biophys Res Comm* 182(1):348-354 (1992)

Iyer et al, *J Org Chem* 55:4693-4699 (1990) Jakobovits et al, "Germ-line transmission and expression of a human-derived yeast artificial chromosome", Nature, Vol. 362, pp. 255-261 (1993)

Jakubiczka et al, "A bovine homologue of the human TSPY gene", *Genomics* 17(3):732-735 (1993)

James-Pederson et al, "Flanking and intragenic sequences regulating the expression of the rabbit alpha-globin gene", *J. Bio. Chem* 270:3965-3973 (1995)

Jeung et al, "Molecular cloning of the full-length cDNA encoding the human calbindin-D9k", *FEBS Lett* 307(2): 224-228 (1992)

Johnson et al, "Construction of single-chain Fvb derivatives of monoclonal antibodies and their production in *Escherichia coli* in Methods in Enzymology (J J Langone, ed.; Academic Press, New York, N.Y.) 203:88-99 1991

Johnstone et al, *Immunochemistry in Practice*, Blackwell Scientific Publications, Oxford, 1982

Jogi et al, "Patched 2, located in 1p32-34, is not mutated in high stage neuroblastoma tumors", *Int J Oncol* 16:943-949 (2000)

Joseph et al, "Optimization of an anti-HIV hairpin ribozyme by in vitro selection", *J Biol Chem* 268:24515 (1993)

Kähäri et al, "Deletion analyses of 5'-flanking region of the human elastin gene. Delineation of functional promoter and regulatory cis-elements", *J Biol Chem* 265(16):9485-9490 (1990)

Kanamaru et al, "Biological effects and cellular uptake of c-myc antisense oligonucleotides and their cationic liposome complexes", *J Drug Target* 5:235-246 (1998)

Kim et al, "A new non-viral DNA delivery vector: the terplex system", *J Controlled Release* 53(1-3):175-82 (1998)

Kim et al, "Introduction of gadd53 gene into gastric cancer cells can modulate sensitivity to anticancer agents in association with apoptosis", *Anticancer Res* 19:1779-1783 (1999)

Kita et al, "Growth inhibition of human pancreatic cancer cell lines by anti-sense oligonucleotides specific to mutated K-ras genes", *Int J Cancer* 80:553-558 (1999)

Kondo et al, "Modulation of apoptosis by endogenous Bcl-xL expression in MKN-45 human gastric cancer cells", *Oncogene* 17:2585-2591 (1998)

Korabiowska et al, "Loss of growth arrest DNA damage genes expression in oral melanomas", *In Vivo* 13:483-485 (1999)

Kumar et al, "Antisense RNA: function and fate of duplex RNA in cells of higher eukaryotes", *Microbiol Mol Biol Rev,* 62:1415-1434 (1998)

Lamb et al, "Introduction and expression of the 400 kilobase precursor amyloid protein gene in transgenic mice", *Nature Genetics,* Vol. 5, pp. 22-29 (1993).

Lane D P, "Cancer. p53, guardian of the genome", *Nature* 358(6381):15-6 (1992)

Langner et al, "Viral particles with heterologous binding motifs. An approach to specifically alter the tropism of the B-lymphotropic papovavirus", *Adv Exp Med Biol* 451:415-422 (1998)

Lanz et al, "A steroid receptor coactivator, SRA, functions as an RNA and is present in an SRC-1 complex" *Cell* 97:117-27 (1999)

Lavitrano et al, "Sperm cells as vectors for introducing foreign DNA into eggs: genetic transformation of mice", *Cell* 57(5):717-723 (1989)

Lawrence et al, "Overexpression of Bcl-2 with herpes simplex virus vectors protects CNS neurons against neurological insults in vitro and in vivo", *J Neurosci* 16:486-496 (1996)

Lefebvre-d'Hellencourt et al, "Immunomodulation by cytokine antisense oligonucleotides", *Eur Cytokine Netw* 6:7 (1995)

Lev-Lehman et al, "Antisense Oligomers in vitro and in vivo" in *Antisense Therapeutics,* Cohen et al, eds (Plenum Press, New York) (1997)

Libert et al, "Cloning and functional characterization of a human A1 adenosine receptor", *Biochem Biophys Res Comm* 187(2):919-926 (1992) Lo, 1983

Mansour S L, "Gene targeting in murine embryonic stem cells: introduction of specific alterations into the mammalian genome", *Genet Anal Tech Appl* 7(8):219-227 (1990)

Martinou et al, "Overexpression of BCL-2 in transgenic mice protects neurons from naturally occurring cell death and experimental ischemia", *Neuron* 13:1017-1030 (1994)

Meinkoth et al, "Hybridization of nucleic acids immobilized on solid supports", *Anal Biochem* 138:267-284 (1984)

Meiri et al, "Memory and long-term potentiation (LTP) dissociated: normal spatial memory despite CA1 LTP elimination with Kv1.4 antisense", *Proc Natl Acad Sci,* 95:15037-15042 (1998)

Mernaugh et al, "An overview of phage-displayed recombinant antibodies" in *Molecular Methods In Plant Pathology* (Singh et al, eds.), CRC Press Inc., Boca Raton, Fla. (1995) pp. 359-365

Meyer et al, "Cationic liposomes coated with polyethylene glycol as carriers for oligonucleotides," *J Biol Chem* 273 (25):15621-15627 (1998)

Mishell et al (eds), *Selected Methods in Cellular Immunology,* W.H. Freeman and Co., New York (1980)

Mizuguchi et al, "Efficient gene transfer into mammalian cells using fusogenic liposome", *Biochem Biophys Res Commun* 218:402-407 (1996)

Murad et al, "Suppression of fibroblast proliferation and lysyl hydroxylase activity by minoxidil", *J Biol Chem* 262(25): 11973-11978 (1987)

Muranishi et al, "Lipophilic peptides: synthesis of lauroyl thyrotropin-releasing hormone and its biological activity", *Pharm Research* 8:649-652 (1991)

Nahmias et al, "Molecular characterization of the mouse beta 3-adrenergic receptor: relationship with the atypical receptor of adipocytes", *EMBO J.* 10(12):3721-3727 (1991)

Nakamura et al, "A comparison of in vivo gene delivery methods for antisense therapy in ligament healing", *Gene Ther* 5:1455-1461 (1998)

Narumi et al, "Adenovirus vector-mediated perforin expression driven by a glucocorticoid-inducible promoter inhibits tumor growth in vivo", *Am J Respir Cell Mol Biol* 19:936-941 (1998)

Nicholson et al, "Caspases: killer proteases", *Trends Biochem Sci* 22:299-306 (1997)

Nishida et al, "Adenovirus-mediated gene transfer to nucleus pulposus cells. Implications for the treatment of intervertebral disc degeneration", *Spine* 23:2437-2442, 1998

Noguchi et al, "Membrane fusion plays an important role in gene transfection mediated by cationic liposomes", *FEBS Lett* 433:169-173 (1998)

Obeso et al, "A Hemangioendothelioma-Derived Cell Line: Its Use as a Model for the Study of Endothelial Cell Biology", *Laboratory Investigation* 83:259-264 (1990)

Okubo et al, "Complementary DNA sequence (EST) collections and the expression information of the human genome", *FEBS Lett* 403:225-229 (1997)

Oro et al, "The *Drosophila* gene knirps-related is a member of the steroid-receptor gene superfamily", *Nature* 336(6198): 493-496 (1988)

Paglia et al, "Gene transfer in dendritic cells, induced by oral DNA vaccination with *Salmonella typhimurium,* results in protective immunity against a murine fibrosarcoma", *Blood* 92(9):3172-3176 (1998)

Pearson et al, "Expression of the human β-amyloid precursor protein gene from a heast artificial chromosome in transgenic mice", *Proc Natl Scad Sci USA* 90:10578-10582 (1993)

Pederson et al, "Combined cytosine deaminase expression, 5-fluorocytosine exposure, and radiotherapy increases cytotoxicity to cholangiocarcinoma cells", *J Gastrointest Surg* 2:283-291 (1998)

Peng Ho et al, "Modification of phosphorothioate oligonucleotides yields potent analogs with minimal toxicity for antisense experiments in the CNS", *Brain Res Mol Brain Res* 62(1):1-11 (1998)

Perbal, A Practical Guide to Molecular Cloning, John Wiley & Sons, New York (1988)

Phelan et al, "The human mammary-derived growth inhibitor (MDGI) gene: genomic structure and mutation analysis in human breast tumors", *Genomics* 34:63-68 (1996)

Potier et al, "The human glutamate receptor cDNA GluR1: cloning, sequencing, expression and localization to chromosome 5", *DNA Seq* 2(4):211-218 (1992)

Price et al, 1992

Quattrone et al, "Enhancing antisense oligonucleotide intracellular levels by means of cationic lipids as vectors", *Biochemica* 1:25-29 (1995)

Reaume et al, "Enhanced amyloidogenic processing of the beta-amyloid precursor protein in gene-targeted mice bearing the Swedish familial Alzheimer's disease mutations and a "humanized" Abeta sequence", *J Biol Chem* 271(38): 23380-8 (1996)

Reecy et al, "Multiple regions of the porcine alpha-skeletal actin gene modulate muscle-specific expression in cell culture and directly injected skeletal muscle", *Anim Biotechnol* 9:101-120 (1998)

Reed J C, "Bcl-2 and the regulation of programmed cell death", *J Cell Biol* 124:1-6 (1994)

Rothstein, "Targeting, disruption, replacement, and allele rescue: integrative DNA transformation in yeast" in Methods in Enzymology, Vol. 194, "Guide to Yeast Genetics and Molecular Biology", eds. C. Guthrie and G. Fink, Academic Press, Inc., Chap. 19, pp. 281-301 (1991).

Saika et al, "Effect of lysyl hydroxylase inhibitor, minoxidil, on ultrastructure and behavior of cultured rabbit subconjunctival fibroblasts", *Graefes Arch Clin Exp Ophthalmol* 233(6):347-353 (1995)

Sambrook et al (Eds), *Molecular Cloning: A Laboratory Manual*, second edition, Cold Spring Harbor Laboratory Press, Cold Spring Harbor, (NY, 1989, 1992)

Sarver et al, *Gene Regulation and Aids, pp.* 305-325 (1990)

Scanlon et al, "Oligonucleotides-mediated modulation of mammalian gene expression", *FASEB J* 9:1288 (1995)

Schedl et al, "A yeast artificial chromosome covering the tyrosinase gene confers copy number-dependent expression in transgenic mice", Nature, Vol. 362, pp. 258-261 (1993).

Schena et al, "Parallel Human Genome Analysis: Microarray-based Expression Monitoring of 1000 genes", *Proc Natl Acad Sci USA* 93(20):10614-10619 (1996)

Schmidt-Kastner et al "Pixel-based image analysis of HSP70, GADD45 and MAP2 mRNA expression after focal cerebral ischemia: hemodynamic and histological correlates" *Brain Res Mol Brain Res* 63:79-97 (1998)

Schwarzenberger et al, "IL-17 stimulates granulopoiesis in mice: use of an alternate, novel gene therapy-derived method for in vivo evaluation of cytokines", *J Immunol* 161:6383-6389 (1998)

Shaw et al, "Modified deoxyoligonucleotides stable to exonuclease degradation in serum", *Nucleic Acids Res* 19:747-750 (1991)

Shibata et al, "Caspases determine the vulnerability of oligodendroctes in the ischemic brain", *J. Clin. Invest* 106:643-653 (2000)

Shimayama et al, "Cleavage of the highly conserved hairpin-loop region of HIV-1 by synthetic ribozymes", *Nucleic Acids Symp Ser* 29:177-178 (1993)

Shoji et al, "Enhancement of anti-herpetic activity of antisense phosphorothioate oligonucleotides 5' end modified with geraniol", *J Drug Target* 5:261-273 (1998)

Shore et al, "Ribozyme-mediated cleavage of the BCRABL oncogene transcript: in vitro cleavage of RNA and in vivo loss of P210 protein-kinase activity", *Oncogene* 8:3183-3188 (1993)

Smith et al, "Induction of the p53 regulated protein gadd45 with proliferating cell nuclear antigen", *Science* 266:1376-1380 (1994)

Soni et al, "Biodistribution, stability, and antiviral efficacy of liposome-entrapped phosphorothioate antisense oligodeoxynucleotides in ducks for the treatment of chronic duck hepatitis B virus infection", *Hepatology* 28:1402-1410 (1998)

Soukchareun et al, "Use of Nalpha-Fmoc-cysteine(S-thiobutyl) derivatized oligodeoxynucleotides for the preparation of oligodeoxynucleotide-peptide hybrid molecules", *Bioconjug. Chem* 9(4):466-475 (1998)

Spitzer et al, "Inhibition of deoxynucleases by phosphorothioate groups in oligodeoxyribonucleotides", *Nucleic Acids Res* 18:11691-11704 (1988)

Stites et al (eds), *Basic and Clinical Immunology* (8th Edition), Appleton & Lange, Norwalk, Conn. (1994)

Stix, G, "Shutting down a gene. Antisense drug wins approval", *Sci Am* 279(5):46, 50 (1998)

Strauss et al, "Germ line transmission of a yeast artificial chromosome spanning the murine $\alpha_1$ (I) collagen locus", *Science* 259:1904-1907 (1993)

Stridh et al, "Cytochrome c release and caspase activation in hydrogen peroxide- and tributyltin-induced apoptosis", *FEBS Lett* 429:351-355 (1998)

Sugano et al, "Cyclosporin A inhibits $H_2O_2$-induced apoptosis of human fibroblasts", *FEBS Lett* 447:274-276 (1999)

Sugawa et al, "An antisense EGFR oligodeoxynucleotide enveloped in Lipofectin induces growth inhibition in human malignant gliomas in vitro", *J Neurooncol* 39:237-244 (1998)

Sullivan, 1994

Sumimoto et al, "Complementary DNA for the mouse homolog of the small subunit of human cytochrome b558 ", *Biochem Biophys Res Comm* 165(2):902-906 (1989)

Symons R H, "Self-cleavage of RNA in the replication of small pathogens of plants and animals", *Trends Biochem Sci* 14(11):445-450 (1989)

Symons R H, "Small catalytic RNAS", *Annu Rev Biochem* 61:641-671 (1992)

Takekawa et al, "A family of stress-inducible GADD45-like proteins mediate activation of the stress-responsive MTK1/MEKK4 MAPKKK", *Cell* 95:521-530 (1998)

Teoh et al, "Adenovirus vector-based purging of multiple myeloma cells", *Blood*, 92:4591-4601 (1998)

Testoni et al, "A new method of "in-cell reverse transcriptase-polymerase chain reaction" for the detection of BCR/ABL transcript in chronic myeloid leukemia patients", *Blood* 87(9):3822-3827 (1996)

Thompson et al, 1989

Uhlenbeck O C, "A small catalytic oligoribonucleotide", *Nature* 328(6131):596-600 (1987)

Uhlmann et al, "Antisense Oligonucleotides: A New Therapeutic Principle", *Chem Rev* 90(4):543-584, (1990)

van der Putten et al, "Efficient insertion of genes into the mouse germ line via retroviral vectors", *Proc Natl Acad Sci USA* 82(18):6148-6152 (1985)

Velasco-Miguel et al, "PA26, a novel target of p53 tumor suppressor and member of the GADD family of DNA damage and growth arrest inducible genes", *Oncogene* 18(1):127-137 (1999)

Waelti et al., "Delivery to cancer cells of antisense L-myc oligonucleotides incorporated in fusogenic, cationic-lipid-reconstituted influenza-virus envelopes (cationic virosomes)", *Int J Cancer* 77:728-733 (1998)

Wagner, R W "Gene inhibition using antisense oligodeoxynucleotides", *Nature* 372(6504):333-335 (1994)

Wang et al, "3-Hydroxy-3-methylglutaryl coenzyme A lyase (HL): cloning and characterization of a mouse liver HL cDNA and subchromosomal mapping of the human and mouse HL gene", *Mamm Genome* 4(7):382-387 (1993)

Wang, "Cyclic peptides incorporating 4-carboxyphenylalanine and phosphotyrosine are potent inhibitors of pp6O (c-) (src)", *J Controlled Release* 53:39-48 (1998)

Wang et al, "Monitoring gene expression profile changes in ovarian carcinomas using cDNA microarray", *Gene* 229 (1-2):101-108 (1999)

Watson et al, *Recombinant DNA*, Scientific American Books, New York

Weissig et al, "DQAsomes: a novel potential drug and gene delivery system made from Dequalinium", *Pharm Res* 15:334-337 (1998)

Wenger et al, "Oxygen(es) and the hypoxia-inducible factor-1", *Biol Chem* 378(7):609-616 (1997)

Woolf et al, "The stability, toxicity and effectiveness of unmodified and phosphorothioate antisense oligodeoxynucleotides in *Xenopus* oocytes and embryos", *Nucleic Acids Res* 18:1763-1769 (1990)

Yakubov et al, "Mechanism of oligonucleotide uptake by cells: involvement of specific receptors?", *Proc Natl Acad Sci USA* 86(17):6454-6458 (1989)

Yang et al, 1998

Yeh et al, "Inhibition of BMP receptor synthesis by antisense oligonucleotides attenuates OP-1 action in primary cultures of fetal rat calvaria cells", *J Bone Miner Res* 13:1870-1879 (1998)

Yotsuyanagi et al, "Cationic liposomes in gene delivery", *Nippon Rinsho* 56:705-712 (1998)

Zacharia et al, "New reduced peptide bond substance P agonists and antagonists: effects on smooth muscle contraction", *Eur J Pharmacol* 203:353-357 (1991)

Zhan et al, "Abrogation of p53 function affects gadd gene response to DNA base-damaging agents and starvation" *DNA Cell Biol* 15:805-815 (1996)

Zhao et al, "Generating loss-of-function phenotypes of the fushi tarazu gene with a targeted ribozyme in *Drosophila*", *Nature* 365:448-451 (1993)

Zweiger et al, "From Expressed Sequence Tags to "epigenomics": An Understanding of Disease Processes", *Curr Opin Biotechnol* 8(6):684-687 (1997)

AC004283: *Drosophila melanogaster*; DNA sequence (P1 DS05557 (D152)), complete sequence; LOCUS: AC004283; submitted 29 Aug. 1998

AF131826: *Homo sapiens* clone 24945; mRNA sequence, partial cds; LOCUS: AF131826; submitted 12 Mar. 1999

AAB37671 (1703624): LOCUS: AAB37671; submitted 04 Dec. 1996

P52199: Rho-Related GTP-Binding Protein RHOE (RHO8); LOCUS RHOE-HUMAN; submitted 15 Dec. 1998

S73591: MG068 homolog D02_orf346-*Mycoplasma* pneumonia (strain ATCC 29342); LOCUS: S73591; originally submitted 27 Feb. 1997; last revision 7 Dec. 1998

---

What is claimed is:

1. An isolated molecule which comprises the antigen-binding portion of an antibody specific for a polypeptide consisting of SEQ ID NO:4.

2. An isolated molecule in accordance with claim 1, wherein said antibody is a monoclonal antibody.

3. An isolated molecule in accordance with claim 1, comprising a recombinant antibody.

4. An isolated molecule in accordance with claim 1, consisting of an antibody fragment specific for a polypeptide consisting of SEQ ID NO:4.

5. An isolated molecule comprising an antibody specific for a polypeptide consisting of SEQ ID NO:4, or an antibody binding fragment of an antibody specific for a polypeptide consisting of SEQ ID NO:4.

6. An isolated molecule in accordance with claim 5, comprising a monoclonal antibody.

7. An isolated molecule in accordance with claim 5, comprising a recombinant antibody.

8. A molecule comprising an antibody capable of binding to a polypeptide consisting of SEQ ID NO:4, wherein said antibody is a monoclonal antibody or a recombinant antibody.

9. A molecule in accordance with claim 8, comprising a monoclonal antibody.

10. A molecule in accordance with claim 8, comprising a recombinant antibody.

* * * * *

SEQUENCE LISTING

```
<160> NUMBER OF SEQ ID NOS: 21

<210> SEQ ID NO 1
<211> LENGTH: 1655
<212> TYPE: DNA
<213> ORGANISM: Homo sapiens
<220> FEATURE:
<221> NAME/KEY: CDS
<222> LOCATION: (265)..(1575)
<220> FEATURE:
<221> NAME/KEY: misc_feature
<222> LOCATION: (5)..(5)
<223> OTHER INFORMATION: "n" is unknown
<220> FEATURE:
<221> NAME/KEY: misc_feature
<222> LOCATION: (22)..(22)
<223> OTHER INFORMATION: "n" is unknown
<220> FEATURE:
<221> NAME/KEY: misc_feature
<222> LOCATION: (41)..(41)
<223> OTHER INFORMATION: "n" is unknown
<220> FEATURE:
<221> NAME/KEY: misc_feature
<222> LOCATION: (47)..(47)
<223> OTHER INFORMATION: "n" is unknown

<400> SEQUENCE: 1
gcacnaggtg tgtggcagca anagccgcca gttcgggacc nccgcanctg gggtggcaac      60
ggcgcaggag gggtcgcggg gagggagtgg tgagcgcagg cggcaggggt ctgggaaaga     120
cgaagtcgct atttgctgtc tgagcgcgct cgcagctcct ggaagtgttg ccgcctctcg     180
gtttcgctct cgctcgctgc gctcctagaa ggggcggccg cctccaggac tgaccagggc     240
caagtggcgc tcggcgggca ctac atg gcg gag ggt gaa ggg tac ttc gcc        291
                           Met Ala Glu Gly Glu Gly Tyr Phe Ala
                             1               5 atg tct gag gac gag ctg gcc tgc agc ccc tac atc ccc cta ggc ggc       339
Met Ser Glu Asp Glu Leu Ala Cys Ser Pro Tyr Ile Pro Leu Gly Gly
 10              15                  20                  25 gac ttc ggc ggc ggc gac ttc ggc ggc ggc gac ttc ggc ggt ggc ggc       387
Asp Phe Gly Gly Gly Asp Phe Gly Gly Gly Asp Phe Gly Gly Gly Gly
                 30                  35                  40 agc ttc ggt ggg cat tgc ttg gac tat tgc gaa agc cct acg gcg cac       435
Ser Phe Gly Gly His Cys Leu Asp Tyr Cys Glu Ser Pro Thr Ala His
             45                  50                  55
```

```
tgc aat gtg ctg aac tgg gag caa gtg cag cgg ctg gac ggc atc ctg     483
Cys Asn Val Leu Asn Trp Glu Gln Val Gln Arg Leu Asp Gly Ile Leu
        60              65                  70 agc gag acc att ccg att cac ggg cgc ggc aac ttc ccc acg ctc gag     531
Ser Glu Thr Ile Pro Ile His Gly Arg Gly Asn Phe Pro Thr Leu Glu
    75              80                  85 ctg cag ccg agc ctg atc gtg aag gtg gtg cgg cgc gcc gcc gag         579
Leu Gln Pro Ser Leu Ile Val Lys Val Val Arg Arg Arg Leu Ala Glu
90              95                  100                 105 aag cgc att ggc gtc cgc gac gtg cgc ctc aac ggc tcg gca gcc agc     627
Lys Arg Ile Gly Val Arg Asp Val Arg Leu Asn Gly Ser Ala Ala Ser
                110                 115                 120 cat gtc ctg cac cag gac agc ggc ctg ggc tac aag gac ctg gac ctc     675
His Val Leu His Gln Asp Ser Gly Leu Gly Tyr Lys Asp Leu Asp Leu
            125                 130                 135 atc ttc tgc gcc gac ctg cgc ggg gaa ggg gag ttt cag act gtg aag     723
Ile Phe Cys Ala Asp Leu Arg Gly Glu Gly Glu Phe Gln Thr Val Lys
        140                 145                 150 gac gtc gtg ctg gac tgc ctg ttg gac ttc tta ccc gag ggg gtg aac     771
Asp Val Val Leu Asp Cys Leu Leu Asp Phe Leu Pro Glu Gly Val Asn
    155                 160                 165 aaa gag aag atc aca cca ctc acg ctc aag gaa gct tat gtg cag aaa     819
Lys Glu Lys Ile Thr Pro Leu Thr Leu Lys Glu Ala Tyr Val Gln Lys
170                 175                 180                 185 atg gtt aaa gtg tgc aat gac tct gac cga tgg agt ctt ata tcc ctg     867
Met Val Lys Val Cys Asn Asp Ser Asp Arg Trp Ser Leu Ile Ser Leu
                190                 195                 200 tca aac aac agt ggc aaa aat gtg gaa ctg aaa ttt gtg gat tcc ctc     915
Ser Asn Asn Ser Gly Lys Asn Val Glu Leu Lys Phe Val Asp Ser Leu
            205                 210                 215 cgg agg cag ttt gaa ttc agt gta gat tct ttt caa atc aaa tta gac     963
Arg Arg Gln Phe Glu Phe Ser Val Asp Ser Phe Gln Ile Lys Leu Asp
        220                 225                 230 tct ctt ctg ctc ttt tat gaa tgt tca gag aac cca atg act gag aca    1011
Ser Leu Leu Leu Phe Tyr Glu Cys Ser Glu Asn Pro Met Thr Glu Thr
    235                 240                 245 ttt cac ccc aca ata atc ggg gag agc gtc tat ggc gat ttc cag gaa    1059
Phe His Pro Thr Ile Ile Gly Glu Ser Val Tyr Gly Asp Phe Gln Glu
250                 255                 260                 265 gcc ttt gat cac ctt tgt aac aag atc att gcc acc agg aac cca gag    1107
Ala Phe Asp His Leu Cys Asn Lys Ile Ile Ala Thr Arg Asn Pro Glu
                270                 275                 280 gaa atc cga ggg gga ggc ctg ctt aag tac tgc aac ctc ttg gtg agg    1155
Glu Ile Arg Gly Gly Gly Leu Leu Lys Tyr Cys Asn Leu Leu Val Arg
            285                 290                 295 ggc ttt agg ccc gcc tct gat gaa atc aag acc ctt caa agg tat atg    1203
Gly Phe Arg Pro Ala Ser Asp Glu Ile Lys Thr Leu Gln Arg Tyr Met
        300                 305                 310 tgt tcc agg ttt ttc atc gac ttc tca gac att gga gag cag cag aga    1251
Cys Ser Arg Phe Phe Ile Asp Phe Ser Asp Ile Gly Glu Gln Gln Arg
    315                 320                 325 aaa ctg gag tcc tat ttg cag aac ctc ttt gtg gga ttg gaa gcc cgc    1299
Lys Leu Glu Ser Tyr Leu Gln Asn Leu Phe Val Gly Leu Glu Ala Arg
330                 335                 340                 345 aag tat gag tat ctc atg acc ctt cat gga gtg gta aat gag agc tca    1347
Lys Tyr Glu Tyr Leu Met Thr Leu His Gly Val Val Asn Glu Ser Ser
                350                 355                 360 gtg tgc ctg atg gga cat gaa aga aga cag act tta aac ctt atc acc    1395
Val Cys Leu Met Gly His Glu Arg Arg Gln Thr Leu Asn Leu Ile Thr
            365                 370                 375
```

```
atg ctg gct atc cgg gtg tta gct gac caa aat gtc att cct aat gtg    1443
Met Leu Ala Ile Arg Val Leu Ala Asp Gln Asn Val Ile Pro Asn Val
    380                 385                 390 gct aat gtc act tgc tat tac cag cca gcc ccc tat gta gca gat gcc    1491
Ala Asn Val Thr Cys Tyr Tyr Gln Pro Ala Pro Tyr Val Ala Asp Ala
395                 400                 405 aac ttt agc aat tac tac att gca cag gtt cag cca gta ttc acg tgc    1539
Asn Phe Ser Asn Tyr Tyr Ile Ala Gln Val Gln Pro Val Phe Thr Cys
410                 415                 420                 425 cag caa cag acc tac tcc act tgg cta ccc tgc aat taagaatcat         1585
Gln Gln Gln Thr Tyr Ser Thr Trp Leu Pro Cys Asn
                430                 435 ttaaaaatgt cctgtgggga agccatttca gacaagacag gagagaaaaa aaaaaaaaaa   1645
aaaaaaaaaa                                                         1655

<210> SEQ ID NO 2
<211> LENGTH: 437
<212> TYPE: PRT
<213> ORGANISM: Homo sapiens

<400> SEQUENCE: 2
```

Met Ala Glu Gly Glu Gly Tyr Phe Ala Met Ser Glu Asp Glu Leu Ala
1               5                   10                  15

Cys Ser Pro Tyr Ile Pro Leu Gly Gly Asp Phe Gly Gly Gly Asp Phe
                20                  25                  30

Gly Gly Gly Asp Phe Gly Gly Gly Ser Phe Gly Gly His Cys Leu
            35                  40                  45

Asp Tyr Cys Glu Ser Pro Thr Ala His Cys Asn Val Leu Asn Trp Glu
        50                  55                  60

Gln Val Gln Arg Leu Asp Gly Ile Leu Ser Glu Thr Ile Pro Ile His
65                  70                  75                  80

Gly Arg Gly Asn Phe Pro Thr Leu Glu Leu Gln Pro Ser Leu Ile Val
                85                  90                  95

Lys Val Val Arg Arg Leu Ala Glu Lys Arg Ile Gly Val Arg Asp
                100                 105                 110

Val Arg Leu Asn Gly Ser Ala Ala Ser His Val Leu His Gln Asp Ser
        115                 120                 125

Gly Leu Gly Tyr Lys Asp Leu Asp Leu Ile Phe Cys Ala Asp Leu Arg
    130                 135                 140

Gly Glu Gly Glu Phe Gln Thr Val Lys Asp Val Val Leu Asp Cys Leu
145                 150                 155                 160

Leu Asp Phe Leu Pro Glu Gly Val Asn Lys Glu Lys Ile Thr Pro Leu
                165                 170                 175

Thr Leu Lys Glu Ala Tyr Val Gln Lys Met Val Lys Val Cys Asn Asp
            180                 185                 190

Ser Asp Arg Trp Ser Leu Ile Ser Leu Ser Asn Asn Ser Gly Lys Asn
        195                 200                 205

Val Glu Leu Lys Phe Val Asp Ser Leu Arg Arg Gln Phe Glu Phe Ser
    210                 215                 220

Val Asp Ser Phe Gln Ile Lys Leu Asp Ser Leu Leu Leu Phe Tyr Glu
225                 230                 235                 240

Cys Ser Glu Asn Pro Met Thr Glu Thr Phe His Pro Thr Ile Ile Gly
                245                 250                 255

Glu Ser Val Tyr Gly Asp Phe Gln Glu Ala Phe Asp His Leu Cys Asn
            260                 265                 270

-continued

```
Lys Ile Ile Ala Thr Arg Asn Pro Glu Glu Ile Arg Gly Gly Leu
        275                 280                 285

Leu Lys Tyr Cys Asn Leu Leu Val Arg Gly Phe Arg Pro Ala Ser Asp
        290                 295                 300

Glu Ile Lys Thr Leu Gln Arg Tyr Met Cys Ser Arg Phe Phe Ile Asp
305                 310                 315                 320

Phe Ser Asp Ile Gly Glu Gln Gln Arg Lys Leu Glu Ser Tyr Leu Gln
                325                 330                 335

Asn Leu Phe Val Gly Leu Glu Ala Arg Lys Tyr Glu Tyr Leu Met Thr
            340                 345                 350

Leu His Gly Val Val Asn Glu Ser Ser Val Cys Leu Met Gly His Glu
        355                 360                 365

Arg Arg Gln Thr Leu Asn Leu Ile Thr Met Leu Ala Ile Arg Val Leu
    370                 375                 380

Ala Asp Gln Asn Val Ile Pro Asn Val Ala Asn Val Thr Cys Tyr Tyr
385                 390                 395                 400

Gln Pro Ala Pro Tyr Val Ala Asp Ala Asn Phe Ser Asn Tyr Tyr Ile
                405                 410                 415

Ala Gln Val Gln Pro Val Phe Thr Cys Gln Gln Gln Thr Tyr Ser Thr
            420                 425                 430

Trp Leu Pro Cys Asn
        435

<210> SEQ ID NO 3
<211> LENGTH: 3454
<212> TYPE: DNA
<213> ORGANISM: Homo sapiens
<220> FEATURE:
<221> NAME/KEY: CDS
<222> LOCATION: (323)..(1762)
<220> FEATURE:
<221> NAME/KEY: misc_feature
<222> LOCATION: (606)..(606)
<223> OTHER INFORMATION: "n" is unknown
<220> FEATURE:
<221> NAME/KEY: misc_feature
<222> LOCATION: (2561)..(2561)
<223> OTHER INFORMATION: "n" is unknown
<220> FEATURE:
<221> NAME/KEY: misc_feature
<222> LOCATION: (2594)..(2504)
<223> OTHER INFORMATION: "n" is unknown
<220> FEATURE:
<221> NAME/KEY: misc_feature
<222> LOCATION: (2613)..(2613)
<223> OTHER INFORMATION: "n" is unknown

<400> SEQUENCE: 3
ctccgcggcg gggatgctga ggagcgctgg gtccgggagc agccctggcc cctgcggact      60
tccgaggccg tgaaaacccc tgcgctgcgg cccttcccag gccccgagg ccgttcgccg     120 ttcccgaagc ccgactgggg gaagagtcca gcaccaaagc ggccgttctc ggattccgga     180
gcgttctgga gccccgagag acgccccggg gttctagaag ctcccggcg gcgcccagtc     240 ccggcttcat tcgggcgtcc ctccgaaacc cactcgggtg cacgggtcgt cggcgagccg     300
cgaccgggtc ctggcgcgca cc atg atc gtg gcg gac tcc gag tgc cgc gca     352
                         Met Ile Val Ala Asp Ser Glu Cys Arg Ala
                          1               5                  10 gag ctc aag gac tac ctg cgg ttc gcc ccg ggc ggc gtc ggc gac tcg     400
Glu Leu Lys Asp Tyr Leu Arg Phe Ala Pro Gly Gly Val Gly Asp Ser
            15                  20                  25
```

-continued

| | | |
|---|---|---|
| ggc ccc gga gag gag cag agg gag agc cgg gct cgg cga ggc cct cga<br>Gly Pro Gly Glu Glu Gln Arg Glu Ser Arg Ala Arg Arg Gly Pro Arg<br>30              35              40 | | 448 |
| ggg ccc agc gcc ttc atc ccc gtg gag gag gtc ctt cgg gag ggg gct<br>Gly Pro Ser Ala Phe Ile Pro Val Glu Glu Val Leu Arg Glu Gly Ala<br>45              50              55 | | 496 |
| gag agc ctc gag cag cac ctg ggg ctg gag gca ctg atg tcc tct ggg<br>Glu Ser Leu Glu Gln His Leu Gly Leu Glu Ala Leu Met Ser Ser Gly<br>60              65              70 | | 544 |
| cga gta gac aac ctg gca gtg gtg atg ggc ctg cac cct gac tac ttt<br>Arg Val Asp Asn Leu Ala Val Val Met Gly Leu His Pro Asp Tyr Phe<br>75              80              85              90 | | 592 |
| acc agc ttc tgg cnc ctg cac tac ctg ctg ctg cac acg gat ggt ccc<br>Thr Ser Phe Trp Xaa Leu His Tyr Leu Leu Leu His Thr Asp Gly Pro<br>95              100              105 | | 640 |
| ttg gcc agc tcc tgg cgc cac tac att gcc atc atg gct gcc gcc cgc<br>Leu Ala Ser Ser Trp Arg His Tyr Ile Ala Ile Met Ala Ala Ala Arg<br>110              115              120 | | 688 |
| cat cag tgt tct tac ctg gta ggc tcc cac atg gcc gag ttt ctg cag<br>His Gln Cys Ser Tyr Leu Val Gly Ser His Met Ala Glu Phe Leu Gln<br>125              130              135 | | 736 |
| act ggt ggt gac cct gag tgg ctg ctg ggc ctc cac cgg gcc ccc gag<br>Thr Gly Gly Asp Pro Glu Trp Leu Leu Gly Leu His Arg Ala Pro Glu<br>140              145              150 | | 784 |
| aag ctg cgc aaa ctc agc gag atc aac aag ttg ctg gcg cat cgg cca<br>Lys Leu Arg Lys Leu Ser Glu Ile Asn Lys Leu Leu Ala His Arg Pro<br>155              160              165              170 | | 832 |
| tgg ctc atc acc aag gaa cac atc cag gcc ttg ctg aag acc ggc gag<br>Trp Leu Ile Thr Lys Glu His Ile Gln Ala Leu Leu Lys Thr Gly Glu<br>175              180              185 | | 880 |
| cac act tgg tcc ctg gcc gag ctc att cag gct ctg gtc ctg ctc acc<br>His Thr Trp Ser Leu Ala Glu Leu Ile Gln Ala Leu Val Leu Leu Thr<br>190              195              200 | | 928 |
| cac tgc cac tcg ctc tcc tcc ttc gtg ttt ggc tgt ggc atc ctc cct<br>His Cys His Ser Leu Ser Ser Phe Val Phe Gly Cys Gly Ile Leu Pro<br>205              210              215 | | 976 |
| gag ggg gat gca gat ggc agc cct gcc ccc cag gca cct aca ccc cct<br>Glu Gly Asp Ala Asp Gly Ser Pro Ala Pro Gln Ala Pro Thr Pro Pro<br>220              225              230 | | 1024 |
| agt gaa cag agc agc ccc cca agc agg gac ccg ttg aac aac tct ggg<br>Ser Glu Gln Ser Ser Pro Pro Ser Arg Asp Pro Leu Asn Asn Ser Gly<br>235              240              245              250 | | 1072 |
| ggc ttt gag tct gcc cgc gac gtg gag gcg ctg atg gag cgc atg cag<br>Gly Phe Glu Ser Ala Arg Asp Val Glu Ala Leu Met Glu Arg Met Gln<br>255              260              265 | | 1120 |
| cag ctg cag gag agc ctg ctg cgg gat gag ggg acg tcc cag gag gag<br>Gln Leu Gln Glu Ser Leu Leu Arg Asp Glu Gly Thr Ser Gln Glu Glu<br>270              275              280 | | 1168 |
| atg gag agc cgc ttt gag ctg gag aag tca gag agc ctg ctg gtg acc<br>Met Glu Ser Arg Phe Glu Leu Glu Lys Ser Glu Ser Leu Leu Val Thr<br>285              290              295 | | 1216 |
| ccc tca gct gac atc ctg gag ccc tct cca cac cca gac atg ctg tgc<br>Pro Ser Ala Asp Ile Leu Glu Pro Ser Pro His Pro Asp Met Leu Cys<br>300              305              310 | | 1264 |
| ttt gtg gaa gac cct act ttc gga tat gag gac ttc act cgg aga ggg<br>Phe Val Glu Asp Pro Thr Phe Gly Tyr Glu Asp Phe Thr Arg Arg Gly<br>315              320              325              330 | | 1312 |
| gct cag gca ccc cct acc ttc cgg gcc cag gat tat acc tgg gaa gac<br>Ala Gln Ala Pro Pro Thr Phe Arg Ala Gln Asp Tyr Thr Trp Glu Asp<br>335              340              345 | | 1360 |

```
cat ggc tac tcg ctg atc cag cgg ctt tac cct gag ggt ggg cag ctg      1408
His Gly Tyr Ser Leu Ile Gln Arg Leu Tyr Pro Glu Gly Gly Gln Leu
            350                 355                 360 ctg gat gag aag ttc cag gca gcc tat agc ctc acc tac aat acc atc      1456
Leu Asp Glu Lys Phe Gln Ala Ala Tyr Ser Leu Thr Tyr Asn Thr Ile
        365                 370                 375 gcc atg cac agt ggt gtg gac acc tcc gtg ctc cgc agg gcc atc tgg      1504
Ala Met His Ser Gly Val Asp Thr Ser Val Leu Arg Arg Ala Ile Trp
    380                 385                 390 aac tat atc cac tgc gtc ttt ggc atc aga tat gat gac tat gat tat      1552
Asn Tyr Ile His Cys Val Phe Gly Ile Arg Tyr Asp Asp Tyr Asp Tyr
395                 400                 405                 410 ggg gag gtg aac cag ctc ctg gag cgg aac ctc aag gtc tat atc aag      1600
Gly Glu Val Asn Gln Leu Leu Glu Arg Asn Leu Lys Val Tyr Ile Lys
                415                 420                 425 aca gtg gcc tgc tac cca gag aag acc acc cga aga atg tac aac ctc      1648
Thr Val Ala Cys Tyr Pro Glu Lys Thr Thr Arg Arg Met Tyr Asn Leu
            430                 435                 440 ttc tgg agg cac ttc cgc cac tca gag aag gtc cac gtg aac ttg ctg      1696
Phe Trp Arg His Phe Arg His Ser Glu Lys Val His Val Asn Leu Leu
        445                 450                 455 ctc ctg gag gcg cgc atg caa gcc gct ctg ctg tac gcc ctc cgt gcc      1744
Leu Leu Glu Ala Arg Met Gln Ala Ala Leu Leu Tyr Ala Leu Arg Ala
    460                 465                 470 atc acc cgc tac atg acc tgactcctga gcaggacctg ggcccggttc             1792
Ile Thr Arg Tyr Met Thr
475                 480 agctccccac aaggacttct ctgtctggag acagccccag acccttttgt gtcccatgcc    1852
cacccctccc acgctgcagt gggcttgtgt gtgatgtgca gtcccgaagc cacaccctcc    1912
cttttcctca ctggaatgga cagttcattg cactgactct gggatctcag ccctgctcct    1972
gggagctgga gagcacttg gagatcctaa gggaccacac ccttcctcct tcccctgccc     2032
acagaggcag agggcacagg aaagaagccg ggccaagctc ggaattaatg tgccacaagt    2092
gttgtggcct tcctgaactg ggaagtccct ggctggcccc cggggagag gggcaaatgc     2152 ctccgggact gacactccag gcagctttgc cttctctccc ctgtcatttc cagatttcat    2212
tacctcctac ttgccattca cccatcaatg tgaaagtcag ggtcacagct ggtcgtgtg     2272 tccagttccc taaaagcctg ttctgttggg cagcctgagg ctgttgcccg aatcctagtt    2332
cagttttttg acttcctttg ccctttttcc cttttctcca tgcttaatgg tgtgaggcgt    2392
caggagagag gccaagtaca taaaaaaaaa aaaaagcaga ttatctctag agagtttgag    2452
cctttgctgg tcacattgcc ttctgaagag gagggagtat tagattataa atcctcttta    2512
ttttggtcct ttatgcttga ggttccaacc tggagccaca gtgtgtgana ggaggaggag    2572
agggagaatt ctgttctccc anagctgcac ctgcctcgca naggccagca ccccactctc    2632
ctgcctccag tggccctgcc gcagatgtct cccaaaaagt tgagcctttc tagatggctt    2692
aggtggcacc atggctcagc aggaggggcg ggaggcacca gggttcttgt ttggaccctg    2752
cccctgggcc atggccaggt gaccatggct acattgccaa acctctgact gccacagctg    2812
cagactgaga gggtggggtct gagtcccac aatgtctgaa gctgcccctg ggattctcag    2872
gccaacctgc caacagcaag cggatttttct tgcaagatca gggaccccat ttctgcagcc   2932
agtgtctcct gggtgccttc tgaggactcc caccccatc ccagtatctc atctgtcccc    2992
tctcctgggg cttaagtggg ttgcttccag gcagaagcag ccaaggaccg attccaggca    3052
```

-continued

```
ctttctgtag caaatgactg tgaattacga cttctcttgc ccttcttcta gcagtctgtg    3112
cctcctctct gaccagtttg gagggcactg aagaaaggca agggccgtgc tgctgctggg    3172
cggggcagga gaggagcctg gccagtgtgc cacattaaat acccgtgcag gcgcggagaa    3232
gcaaccggca ccccttccg gcctgaaagc cctccctgca agaaggtgtg caggagagaa      3292
gaggccccgg catggggatc tgggttctag agggcatgtg atgactgtaa atgttcactg    3352
ggtgggtagg gagtggtatc cagtgttcaa gtgcagaaat ctttggcttt gctaccagtt    3412
ccatatgatg agaaataaac gttcgctgag gttttgtttc at                        3454
```

<210> SEQ ID NO 4
<211> LENGTH: 480
<212> TYPE: PRT
<213> ORGANISM: Homo sapiens
<220> FEATURE:
<221> NAME/KEY: misc_feature
<222> LOCATION: (118)..(118)
<223> OTHER INFORMATION: "Xaa" is unknown

<400> SEQUENCE: 4

```
Met Ile Val Ala Asp Ser Glu Cys Arg Ala Glu Leu Lys Asp Tyr Leu
1               5                   10                  15

Arg Phe Ala Pro Gly Gly Val Gly Asp Ser Gly Pro Gly Glu Glu Gln
            20                  25                  30

Arg Glu Ser Arg Ala Arg Arg Gly Pro Arg Gly Pro Ser Ala Phe Ile
        35                  40                  45

Pro Val Glu Glu Val Leu Arg Glu Gly Ala Glu Ser Leu Glu Gln His
    50                  55                  60

Leu Gly Leu Glu Ala Leu Met Ser Ser Gly Arg Val Asp Asn Leu Ala
65                  70                  75                  80

Val Val Met Gly Leu His Pro Asp Tyr Phe Thr Ser Phe Trp Xaa Leu
                85                  90                  95

His Tyr Leu Leu Leu His Thr Asp Gly Pro Leu Ala Ser Ser Trp Arg
            100                 105                 110

His Tyr Ile Ala Ile Met Ala Ala Ala Arg His Gln Cys Ser Tyr Leu
        115                 120                 125

Val Gly Ser His Met Ala Glu Phe Leu Gln Thr Gly Gly Asp Pro Glu
    130                 135                 140

Trp Leu Leu Gly Leu His Arg Ala Pro Glu Lys Leu Arg Lys Leu Ser
145                 150                 155                 160

Glu Ile Asn Lys Leu Leu Ala His Arg Pro Trp Leu Ile Thr Lys Glu
                165                 170                 175

His Ile Gln Ala Leu Leu Lys Thr Gly Glu His Thr Trp Ser Leu Ala
            180                 185                 190

Glu Leu Ile Gln Ala Leu Val Leu Leu Thr His Cys His Ser Leu Ser
        195                 200                 205

Ser Phe Val Phe Gly Cys Gly Ile Leu Pro Glu Gly Asp Ala Asp Gly
    210                 215                 220

Ser Pro Ala Pro Gln Ala Pro Thr Pro Pro Ser Glu Gln Ser Ser Pro
225                 230                 235                 240

Pro Ser Arg Asp Pro Leu Asn Asn Ser Gly Gly Phe Glu Ser Ala Arg
                245                 250                 255

Asp Val Glu Ala Leu Met Glu Arg Met Gln Gln Leu Gln Glu Ser Leu
            260                 265                 270

Leu Arg Asp Glu Gly Thr Ser Gln Glu Glu Met Glu Ser Arg Phe Glu
        275                 280                 285
```

Leu Glu Lys Ser Glu Ser Leu Leu Val Thr Pro Ser Ala Asp Ile Leu
290                 295                 300

Glu Pro Ser Pro His Pro Asp Met Leu Cys Phe Val Glu Asp Pro Thr
305                 310                 315                 320

Phe Gly Tyr Glu Asp Phe Thr Arg Arg Gly Ala Gln Ala Pro Pro Thr
                325                 330                 335

Phe Arg Ala Gln Asp Tyr Thr Trp Glu Asp His Gly Tyr Ser Leu Ile
            340                 345                 350

Gln Arg Leu Tyr Pro Glu Gly Gly Gln Leu Leu Asp Glu Lys Phe Gln
        355                 360                 365

Ala Ala Tyr Ser Leu Thr Tyr Asn Thr Ile Ala Met His Ser Gly Val
370                 375                 380

Asp Thr Ser Val Leu Arg Arg Ala Ile Trp Asn Tyr Ile His Cys Val
385                 390                 395                 400

Phe Gly Ile Arg Tyr Asp Asp Tyr Asp Tyr Gly Glu Val Asn Gln Leu
                405                 410                 415

Leu Glu Arg Asn Leu Lys Val Tyr Ile Lys Thr Val Ala Cys Tyr Pro
            420                 425                 430

Glu Lys Thr Thr Arg Arg Met Tyr Asn Leu Phe Trp Arg His Phe Arg
        435                 440                 445

His Ser Glu Lys Val His Val Asn Leu Leu Leu Glu Ala Arg Met
450                 455                 460

Gln Ala Ala Leu Leu Tyr Ala Leu Arg Ala Ile Thr Arg Tyr Met Thr
465                 470                 475                 480

<210> SEQ ID NO 5
<211> LENGTH: 4138
<212> TYPE: DNA
<213> ORGANISM: Homo sapiens

<400> SEQUENCE: 5
gacgagcggg agcgcggagc agcagcctct gctgccctga cttttaaga aatctcaatg      60
aactatttgt agagaatcac tgatccggcc tgcaagcatt tgcacggca aaatatcga     120
tcagtgttaa gtgaagatca cattttatat gcgatcttga cttttttgtc ttacattata    180
ttttataga ttttgttata aacatggtgc tgggaaggt gaagagtttg acaataagct      240
ttgactgtct taatgacagc aatgtccctg tgtattctag tggggatacc gtctcaggaa    300
gggtaaattt agaagttact ggggaaatca gagtaaaatc tcttaaaatt catgcaagag    360
gacatgcgaa agtacgctgg actgaatcta gaaacgccgg ctccaatact gcctatacac    420
agaattacac tgaagaagta gagtatttca accataaaga catcttaatt gggcacgaaa    480
gagatgatga taattccgaa gaaggcttcc acactattca ttcaggaagg catgaatatg    540
cattcagctt cgagcttcca cagacaccac tcgctacctc attcgaaggc cgacatggca    600
gtgtgcgcta ttgggtgaaa gccgaattgc acaggccttg gctactacca gtaaaattaa    660
agaaggaatt tacagtcttt gagcatatag atatcaacac tccttcatta ctgtcacccc    720
aagcaggcac aaaagaaaag acactctgtt gctggttctg tacctcaggc ccaatatcct    780
taagtgccaa aattgaaagg aagggctata ccccaggtga atcaattcag atatttgctg    840
agattgagaa ctgctcttcc cgaatggtgg tgccaaaggc agccatttac caaacacagg    900
ccttctatgc caagggaaa atgaaggaag taaacagct tgtggctaac ttgcgtgggg      960
aatccttatc atctggaaag acagagacgt ggaatggcaa gttgctgaaa attccaccag   1020

```
tttctccctc tatcctcgac tgtagtataa tccgcgtgga atattcacta atggtatatg    1080
tggatattcc tggagctatg gatttatttc ttaatttgcc acttgtcatc ggtaccattc    1140
ctctacatcc atttggtagc agaacctcaa gtgtaagcag tcagtgtagc atgaatatga    1200
actggctcag tttatcactt cctgaaagac ctgaagcacc acccagctat gcagaagtgg    1260
taacagagga acaaaggcgg aacaatcttg caccagtgag tgcttgtgat gactttgaga    1320
gagcccttca aggaccactg tttgcatata tccaggagtt tcgattcttg cctccacctc    1380
tttattcaga gattgatcca aatcctgatc agtcagcaga tgatagacca tcctgcccct    1440
ctcgttgaag aacacttgg ttgaatcaag ttgatgtggg ttccgaactg tatctcttcc     1500
ggctgaggac agagaagtat cttggagaca cgtttcagag gaagtggaat tacttttgcc    1560
cagaaaaatg gcgaatacat gaaacaacca gtgatcatgc tttagaagcc tacagcaaca    1620
ttctgagact gctccaacat gcttgaagat ctaagctttt ctcttttaaa actggcacat    1680
actcagagca gtcttcttag cctatggtcg tacgtgtcaa gacatcacgt tgtaaagagg    1740
gatgatttcc ttctttttgat ttgaaaattt gcacatgctc aatgcttaca ttgtgcggtt   1800
cgacgtcact acagcttctt ttttttttt ttttttcta tttttgccag actcttgata      1860
ctcttaaaac ttgtttgtgg tcagcacaac aaggaacaaa acaaagcttt gaaaaaactt    1920
taacatgaaa aaacgcactg acattttttt ttatttaata tagcctggac tttacctgcg    1980
tatgcacatg ctcagaattg tctactaggc tgactatgta tcacctcttc agcttggatc    2040
caattgtgga tttatttaca aacatcaaat gccttcaagc caatcctttt tgctgtatgt    2100
tttgcagcct actgtagtag atacgcaaca gataatgtgg gaaaaaaga gataagagga     2160 ggaagctaat aagagactgt caagattgta taccttcttg gtttcttta agaatttgtt     2220 gcctttctac tattacagca aagcagcatt ttgttactga ctgcctaaaa tcacttaatc    2280
tcaggtgaac gcatcacttg ccaaactgtt ggaatgctat ttgtgttttg ttgcactgtt    2340
tttttcgttt gtttgtttgt ttatttggtt ggcttttttgg agagggaaat ttggaaacgg   2400
gacatacaca aaagttacac acccacattc ccttttttatc atgacataca agaagaaact   2460
agcagagcta agaatggagt gaagaaaggc agtatggcag gcaccagcaa agagttgagg    2520
gctgttgctc ttaaaaatta tttttttttat tattattttg aaagtatgga agttttccat   2580
tcactgggga aaggagggaa aagtgcattt atttttatac agagttactt aattacctcc    2640
aaaacacata tgttggaaat cgcttttgct ggtgcaaagt atattaatga gcaggaatac    2700
atacattgag gttatgaata gagagctcaa tttgtacctt tgctgtcttg ctcaagcttg    2760
gtatggcatg aaaactcgac tttattccaa aagtaacttc aaaatttaaa atactagaac    2820
gtttgctgcg ataaatcttt tggattttttg tgttttctta atgagaatac tgttttcat    2880 tacctaaaga acaatttgct aaacatgaga atcactcac tttgattatg tatagattac     2940
ataggaagaa caatcacatc agtaagttat agtttatatt aaaggtaatt ttctgttggc    3000
tcataacaaa tataccagca ttcatgatag catttcagca ttttccaagg taccaagtgt    3060
acttattttg ttgttgttgt tgttgttgta ttttagaagg aattcagctc tgatgttttt    3120
aaagaaaacc agcatctctg atgttgcaac atacgtgtaa aatgggtgtt acatctatcc    3180
tgccatttaa ccccacagtt aataaagtgg ctgaaaataa tagtagctct ggcttggtgc    3240
ttgacctggt taaatactgt cttaaagctc atacaaaaca aataggcttt tccataagtg    3300
gcctttaaga aaacatggaa gacaattcat gtttgacaaa tgctgacagg gtgaagaaag    3360
cccagtgtaa aaatgaatcg cgttttaagt gattcggkta aagagtttgg gctcccgtag    3420
```

| | |
|---|---|
| caaactaata ctagataata aggaaatggg ggtgaaatat ttttttattg ttgaatcatt | 3480 |
| ttgtgaatgt ccccctcaaa aaaagctaat ggaatatttg gcataaaggg catttggtgg | 3540 |
| ttttattttt gtttgagggg gattgtcaga aaatcccttt tctctcttac gtctaactga | 3600 |
| ctagggaaca attgttgata tgcatagcat tggaatactt gtcattatat actcttacaa | 3660 |
| ataacacatg aagcaagaat gaccaatatt ctgataattg cactggatc acaaaatgtg | 3720 |
| ataaaacttt aaatgtataa aactttatca aataaagttt tattttcccc tttaaaatgt | 3780 |
| atttctttag aggcattact ttttaaaaa tattggtcaa ttcctgacat aagatgtgag | 3840 |
| gttcacagtt gtattccagt attcaagata gattcctgat ttttcaatta ggaaaagtaa | 3900 |
| aatccaaaat gttagcaaaa caaagtgcaa tattaaatgt ttgctttata gattatattc | 3960 |
| tatggctgtt tgtaatttct cttttttcc tttttattt ggtgctgaat atgtccttgt | 4020 |
| aggctctgtt ttaagaaaac aatatgtggg aaatgattta atttttccta ttgctcttcc | 4080 |
| ttgtggaaaa taaagtgttt tgttttttc tgtttgtaa aaaaaaaaa aaaaaaaa | 4138 |

<210> SEQ ID NO 6
<211> LENGTH: 1303
<212> TYPE: DNA
<213> ORGANISM: Homo sapiens
<220> FEATURE:
<221> NAME/KEY: misc_feature
<222> LOCATION: (52)..(52)
<223> OTHER INFORMATION: "n" is unknown
<220> FEATURE:
<221> NAME/KEY: misc_feature
<222> LOCATION: (92)..(92)
<223> OTHER INFORMATION: "n" is unknown
<220> FEATURE:
<221> NAME/KEY: misc_feature
<222> LOCATION: (1212)..(1212)
<223> OTHER INFORMATION: "n" is unknown
<220> FEATURE:
<221> NAME/KEY: misc_feature
<222> LOCATION: (1288)..(1288)
<223> OTHER INFORMATION: "n" is unknown
<220> FEATURE:
<221> NAME/KEY: misc_feature
<222> LOCATION: (1290)..(1290)
<223> OTHER INFORMATION: "n" is unknown
<220> FEATURE:
<221> NAME/KEY: misc_feature
<222> LOCATION: (1291)..(1291)
<223> OTHER INFORMATION: "n" is unknown
<220> FEATURE:
<221> NAME/KEY: misc_feature
<222> LOCATION: (1293)..(1293)
<223> OTHER INFORMATION: "n" is unknown
<220> FEATURE:
<221> NAME/KEY: misc_feature
<222> LOCATION: (1294)..(1294)
<223> OTHER INFORMATION: "n" is unknown
<220> FEATURE:
<221> NAME/KEY: misc_feature
<222> LOCATION: (1295)..(1295)
<223> OTHER INFORMATION: "n" is unknown
<220> FEATURE:
<221> NAME/KEY: misc_feature
<222> LOCATION: (1296)..(1296)
<223> OTHER INFORMATION: "n" is unknown

<400> SEQUENCE: 6

| | |
|---|---|
| cctcctcccc tcctcccgcc cacgcccctg ctccccgccc ccggaagccc cngcggaacg | 60 |
| gttacgccgc gacgaagtaa gggtgggttc tnaaggaaag cccttttgcca atcttgcaag | 120 |
| atttgtagac cagcactaca aagatcgcat agatcaaata ggaaaaaaaa tgtcgatttt | 180 |

```
tattcagtct gatggttctg ttcttcattg tgattgtcat taaaaagtgg taaattgctc    240
aatgtaatat ttttgtgcgc tgtttagaag ttgtgtgatt ttttgccatc gttgataaaa    300
atgcaaagtc aaataaaagg tgtcttggtt tgatgtcata gaatgatcca aggagagaaa    360
aaaggtagtt actgttttca ccagaaaagg taatgagtga aggaaagaat agtagcagaa    420
agcacagttt gtgagtaaag ctgtctggaa ttaagttacc aaaaatacaa agcaaaagga    480
ctattatttt gggttgaagc tccaaaactg acagcatctg ataatctgtt ggtttatttc    540 actttttcatt aaatgaacat tgatgagaga agatgccact tacccaagct ttagagaatc    600
cctagtggaa gattatatga taaactttca gtcctgacat aacactaggg catttctaga    660
gtgtcattgc taaaacctca ctgaacagac gcagccaagg tctgtgttca gcacttggtc    720
tctgttgtta cgtaaaataa taagcattta aaatagttta cagatatttt tgaccagttc    780
cttttagaga ttctttcaga gaagaaacca gatctgacct gtttattgtt ggcgcttgtt    840
gaaaacgagc tttctttccc atgatagtgc ttcgttttg aagtgttgaa gctgtgctcc    900
ccttaaatcg tggcaggaga gattaaggta attacaacac tcagttctat gtcttacaag    960
cactttgtct tgtctctgca agaaaattcg attccagtca tttcccataa aatacagaca   1020
ttttaccaac ataatatgct tgattgatg cagcattatg ctttgggcag tattacaaaa   1080
tagctggcga gtgctttctg tatttaaata ttgtaaaaag aaaataagtt ataactgtta   1140
taaagcagaa cttttgttgc attttttaaa ctgttgaagt cnctgtgtat gtttgtttgg   1200
tcaatgtttc cncagtattt attaaaacat actttttttt ttcttcaaat aaaaaagtaa   1260
ccatgtcttt gtctaaaaaa aaaaaaaanan nannnnaaaa aaa                    1303
```

<210> SEQ ID NO 7
<211> LENGTH: 244
<212> TYPE: PRT
<213> ORGANISM: Homo sapiens
<220> FEATURE:
<221> NAME/KEY: misc_feature
<222> LOCATION: (118)..(118)
<223> OTHER INFORMATION: "Xaa" is unknown

<400> SEQUENCE: 7

```
Met Lys Glu Arg Arg Ala Ser Gln Lys Leu Ser Ser Lys Ser Ile Met
1               5                   10                  15

Asp Pro Asn Gln Asn Val Lys Cys Lys Ile Val Val Gly Asp Ser
            20                  25                  30

Gln Cys Gly Lys Thr Ala Leu Leu His Val Phe Ala Lys Asp Cys Phe
        35                  40                  45

Pro Glu Asn Tyr Val Pro Thr Val Phe Glu Asn Tyr Thr Ala Ser Phe
    50                  55                  60

Glu Ile Asp Thr Gln Arg Ile Glu Leu Ser Leu Trp Asp Thr Ser Gly
65                  70                  75                  80

Ser Pro Tyr Tyr Asp Asn Val Arg Pro Leu Ser Tyr Pro Asp Ser Asp
                85                  90                  95

Ala Val Leu Ile Cys Phe Asp Ile Ser Arg Pro Glu Thr Leu Asp Ser
            100                 105                 110

Val Leu Lys Lys Trp Xaa Gly Glu Ile Gln Glu Phe Cys Pro Asn Thr
        115                 120                 125

Lys Met Leu Leu Val Gly Cys Lys Ser Asp Leu Arg Thr Asp Val Ser
    130                 135                 140

Thr Leu Val Glu Leu Ser Asn His Arg Gln Thr Pro Val Ser Tyr Asp
145                 150                 155                 160
```

```
Gln Gly Ala Asn Met Ala Lys Gln Ile Gly Ala Ala Thr Tyr Ile Glu
                165                 170                 175
Cys Ser Ala Leu Gln Ser Glu Asn Ser Val Arg Asp Ile Phe His Val
            180                 185                 190
Ala Thr Leu Ala Cys Val Asn Lys Thr Asn Lys Asn Val Lys Arg Asn
        195                 200                 205
Lys Ser Gln Arg Ala Thr Lys Arg Ile Ser His Met Pro Ser Arg Pro
    210                 215                 220
Glu Leu Ser Ala Val Ala Thr Asp Leu Arg Lys Asp Lys Ala Lys Ser
225                 230                 235                 240
Cys Thr Val Met

<210> SEQ ID NO 8
<211> LENGTH: 2479
<212> TYPE: DNA
<213> ORGANISM: Rattus rattus
<220> FEATURE:
<221> NAME/KEY: CDS
<222> LOCATION: (1)..(2274)

<400> SEQUENCE: 8
```

| | | | | | | | | | | | | | | | | |
|---|---|---|---|---|---|---|---|---|---|---|---|---|---|---|---|---|
| atg | ggg | gga | tgc | acg | gtg | aag | cct | cag | ctg | ctg | ctc | ctg | gcg | ctc | gtc | 48 |
| Met | Gly | Gly | Cys | Thr | Val | Lys | Pro | Gln | Leu | Leu | Leu | Leu | Ala | Leu | Val | |
| 1 | | | | 5 | | | | | 10 | | | | | 15 | | |
| ctc | cac | ccc | tgg | aat | ccc | tgt | ctg | ggt | gcg | gac | tcg | gag | aag | ccc | tcg | 96 |
| Leu | His | Pro | Trp | Asn | Pro | Cys | Leu | Gly | Ala | Asp | Ser | Glu | Lys | Pro | Ser | |
| | | | | 20 | | | | | 25 | | | | | 30 | | |
| agc | atc | ccc | aca | gat | aaa | tta | tta | gtc | ata | act | gta | gca | aca | aaa | gaa | 144 |
| Ser | Ile | Pro | Thr | Asp | Lys | Leu | Leu | Val | Ile | Thr | Val | Ala | Thr | Lys | Glu | |
| | | | 35 | | | | | 40 | | | | | 45 | | | |
| agt | gat | gga | ttc | cat | cga | ttt | atg | cag | tca | gcc | aaa | tat | ttc | aat | tat | 192 |
| Ser | Asp | Gly | Phe | His | Arg | Phe | Met | Gln | Ser | Ala | Lys | Tyr | Phe | Asn | Tyr | |
| | | 50 | | | | | 55 | | | | | 60 | | | | |
| act | gtg | aag | gtc | ctt | ggt | caa | gga | gaa | gaa | tgg | aga | ggt | ggt | gat | gga | 240 |
| Thr | Val | Lys | Val | Leu | Gly | Gln | Gly | Glu | Glu | Trp | Arg | Gly | Gly | Asp | Gly | |
| 65 | | | | | 70 | | | | | 75 | | | | | 80 | |
| att | aat | agt | att | gga | ggg | ggc | cag | aaa | gtg | aga | tta | atg | aaa | gaa | gtc | 288 |
| Ile | Asn | Ser | Ile | Gly | Gly | Gly | Gln | Lys | Val | Arg | Leu | Met | Lys | Glu | Val | |
| | | | | 85 | | | | | 90 | | | | | 95 | | |
| atg | gaa | cac | tat | gct | gat | caa | gat | gat | ctg | gtt | gtc | atg | ttt | act | gaa | 336 |
| Met | Glu | His | Tyr | Ala | Asp | Gln | Asp | Asp | Leu | Val | Val | Met | Phe | Thr | Glu | |
| | | | 100 | | | | | 105 | | | | | 110 | | | |
| tgc | ttt | gat | gtc | ata | ttt | gct | ggt | ggt | cca | gaa | gaa | gtt | cta | aaa | aaa | 384 |
| Cys | Phe | Asp | Val | Ile | Phe | Ala | Gly | Gly | Pro | Glu | Glu | Val | Leu | Lys | Lys | |
| | | 115 | | | | | 120 | | | | | 125 | | | | |
| ttc | caa | aag | gca | aac | cac | aaa | gtg | gtc | ttt | gca | gca | gat | gga | att | ttg | 432 |
| Phe | Gln | Lys | Ala | Asn | His | Lys | Val | Val | Phe | Ala | Ala | Asp | Gly | Ile | Leu | |
| | | 130 | | | | | 135 | | | | | 140 | | | | |
| tgg | cca | gat | aaa | aga | cta | gca | gac | aag | tat | cct | gtt | gtg | cac | att | ggg | 480 |
| Trp | Pro | Asp | Lys | Arg | Leu | Ala | Asp | Lys | Tyr | Pro | Val | Val | His | Ile | Gly | |
| 145 | | | | | 150 | | | | | 155 | | | | | 160 | |
| aaa | cgc | tat | ctg | aat | tca | gga | gga | ttt | att | ggc | tat | gct | cca | tat | gtc | 528 |
| Lys | Arg | Tyr | Leu | Asn | Ser | Gly | Gly | Phe | Ile | Gly | Tyr | Ala | Pro | Tyr | Val | |
| | | | | 165 | | | | | 170 | | | | | 175 | | |
| aac | cgt | ata | gtt | caa | caa | tgg | aat | ctc | cag | gat | aat | gat | gat | gat | cag | 576 |
| Asn | Arg | Ile | Val | Gln | Gln | Trp | Asn | Leu | Gln | Asp | Asn | Asp | Asp | Asp | Gln | |
| | | | | 180 | | | | | 185 | | | | | 190 | | |
| ctc | ttt | tac | act | aaa | gtt | tac | att | gat | cca | ctg | aaa | agg | gaa | gct | att | 624 |
| Leu | Phe | Tyr | Thr | Lys | Val | Tyr | Ile | Asp | Pro | Leu | Lys | Arg | Glu | Ala | Ile | |

```
                195                 200                 205
aac atc aca ttg gat cac aaa tgc aaa att ttc cag acc tta aat gga      672
Asn Ile Thr Leu Asp His Lys Cys Lys Ile Phe Gln Thr Leu Asn Gly
210                 215                 220 gct gta gat gaa gtt gtt tta aaa ttt gaa aat ggc aaa gcc aga gct      720
Ala Val Asp Glu Val Val Leu Lys Phe Glu Asn Gly Lys Ala Arg Ala
225                 230                 235                 240 aag aat aca ttt tat gaa aca tta cca gtg gca att aat gga aat gga      768
Lys Asn Thr Phe Tyr Glu Thr Leu Pro Val Ala Ile Asn Gly Asn Gly
                245                 250                 255 ccc acc aag att ctc ctg aat tat ttt gga aac tat gta ccc aat tca      816
Pro Thr Lys Ile Leu Leu Asn Tyr Phe Gly Asn Tyr Val Pro Asn Ser
            260                 265                 270 tgg aca cag gat aat ggc tgc act ctt tgt gaa ttc gat aca gtc gac      864
Trp Thr Gln Asp Asn Gly Cys Thr Leu Cys Glu Phe Asp Thr Val Asp
        275                 280                 285 ttg tct gca gta gat gtc cat cca aac gta tca ata ggt gtt ttt att      912
Leu Ser Ala Val Asp Val His Pro Asn Val Ser Ile Gly Val Phe Ile
    290                 295                 300 gag caa cca acc cct ttt cta cct cgg ttt ctg gac ata ttg ttg aca      960
Glu Gln Pro Thr Pro Phe Leu Pro Arg Phe Leu Asp Ile Leu Leu Thr
305                 310                 315                 320 ctg gat tac cca aaa gaa gca ctt aaa ctt ttt att cat aac aaa gaa     1008
Leu Asp Tyr Pro Lys Glu Ala Leu Lys Leu Phe Ile His Asn Lys Glu
                325                 330                 335 gtt tat cat gaa aag gac atc aag gta ttt ttt gat aaa gct aag cat     1056
Val Tyr His Glu Lys Asp Ile Lys Val Phe Phe Asp Lys Ala Lys His
            340                 345                 350 gaa atc aaa act ata aaa ata gta gga cca gaa gaa aat cta agt caa     1104
Glu Ile Lys Thr Ile Lys Ile Val Gly Pro Glu Glu Asn Leu Ser Gln
        355                 360                 365 gcg gaa gcc aga aac atg gga atg gac ttt tgc cgt cag gat gaa aag     1152
Ala Glu Ala Arg Asn Met Gly Met Asp Phe Cys Arg Gln Asp Glu Lys
    370                 375                 380 tgt gat tat tac ttt agt gtg gat gca gat gtt gtt ttg aca aat cca     1200
Cys Asp Tyr Tyr Phe Ser Val Asp Ala Asp Val Val Leu Thr Asn Pro
385                 390                 395                 400 agg act tta aaa att ttg att gaa caa aac aga aag atc att gct cct     1248
Arg Thr Leu Lys Ile Leu Ile Glu Gln Asn Arg Lys Ile Ile Ala Pro
                405                 410                 415 ctt gta act cgt cat gga aag ctg tgg tcc aat ttc tgg gga gca ttg     1296
Leu Val Thr Arg His Gly Lys Leu Trp Ser Asn Phe Trp Gly Ala Leu
            420                 425                 430 agt cct gat gga tac tat gca cga tct gaa gat tat gtg gat att gtt     1344
Ser Pro Asp Gly Tyr Tyr Ala Arg Ser Glu Asp Tyr Val Asp Ile Val
        435                 440                 445 caa ggg aat aga gta gga gta tgg aat gtc cca tat atg gct aat gtg     1392
Gln Gly Asn Arg Val Gly Val Trp Asn Val Pro Tyr Met Ala Asn Val
    450                 455                 460 tac tta att aaa gga aag aca ctc cga tca gag atg aat gaa agg aac     1440
Tyr Leu Ile Lys Gly Lys Thr Leu Arg Ser Glu Met Asn Glu Arg Asn
465                 470                 475                 480 tat ttt gtt cgt gat aaa ctg gat cct gat atg gct ctt tgc cga aat     1488
Tyr Phe Val Arg Asp Lys Leu Asp Pro Asp Met Ala Leu Cys Arg Asn
                485                 490                 495 gct aga gaa atg act tta caa agg gaa aaa gac tcc cct act ccg gaa     1536
Ala Arg Glu Met Thr Leu Gln Arg Glu Lys Asp Ser Pro Thr Pro Glu
            500                 505                 510 aca ttc caa atg ctc agc ccc cca aag ggt gta ttt atg tac att tct     1584
```

|  |  |  |  |  |  |  |  |  |  |  |  |  |  |  |  |
|---|---|---|---|---|---|---|---|---|---|---|---|---|---|---|---|
| Thr | Phe | Gln | Met | Leu | Ser | Pro | Pro | Lys | Gly | Val | Phe | Met | Tyr | Ile | Ser |
|  |  | 515 |  |  |  | 520 |  |  |  | 525 |  |  |  |  |  |

```
aat aga cat gaa ttt gga agg cta tta tcc act gct aat tac aat act    1632
Asn Arg His Glu Phe Gly Arg Leu Leu Ser Thr Ala Asn Tyr Asn Thr
    530             535             540 tcc cat tat aac aat gac ctc tgg cag att ttt gaa aat cct gtg gac    1680
Ser His Tyr Asn Asn Asp Leu Trp Gln Ile Phe Glu Asn Pro Val Asp
545             550             555             560 tgg aag gaa aag tat ata aac cgt gat tat tca aag att ttc act gaa    1728
Trp Lys Glu Lys Tyr Ile Asn Arg Asp Tyr Ser Lys Ile Phe Thr Glu
            565             570             575 aat ata gtt gaa cag ccc tgt cca gat gtc ttt tgg ttc ccc ata ttt    1776
Asn Ile Val Glu Gln Pro Cys Pro Asp Val Phe Trp Phe Pro Ile Phe
        580             585             590 tct gaa aaa gcc tgt gat gaa ttg gta gaa gaa atg gaa cat tac ggc    1824
Ser Glu Lys Ala Cys Asp Glu Leu Val Glu Glu Met Glu His Tyr Gly
    595             600             605 aaa tgg tct ggg gga aaa cat cat gat agc cgt ata tct ggt ggt tat    1872
Lys Trp Ser Gly Gly Lys His His Asp Ser Arg Ile Ser Gly Gly Tyr
        610             615             620 gaa aat gtc cca act gat gat atc cac atg aag caa gtt gat ctg gag    1920
Glu Asn Val Pro Thr Asp Asp Ile His Met Lys Gln Val Asp Leu Glu
625             630             635             640 aat gta tgg ctt cat ttt atc cgg gag ttc att gca cca gtt aca ctg    1968
Asn Val Trp Leu His Phe Ile Arg Glu Phe Ile Ala Pro Val Thr Leu
            645             650             655 aag gtc ttt gca ggc tat tat acg aag gga ttt gca cta ctg aat ttt    2016
Lys Val Phe Ala Gly Tyr Tyr Thr Lys Gly Phe Ala Leu Leu Asn Phe
        660             665             670 gta gta aaa tac tcc cct gaa cga cag cgt tct ctt cgt cct cat cat    2064
Val Val Lys Tyr Ser Pro Glu Arg Gln Arg Ser Leu Arg Pro His His
    675             680             685 gat gct tct aca ttt acc ata aac att gca ctt aat aac gtg gga gaa    2112
Asp Ala Ser Thr Phe Thr Ile Asn Ile Ala Leu Asn Asn Val Gly Glu
        690             695             700 gac ttt cag gga ggt ggt tgc aaa ttt cta agg tac aat tgc tct att    2160
Asp Phe Gln Gly Gly Gly Cys Lys Phe Leu Arg Tyr Asn Cys Ser Ile
705             710             715             720 gag tca cca cga aaa ggc tgg agc ttc atg cat cct ggg aga ctc aca    2208
Glu Ser Pro Arg Lys Gly Trp Ser Phe Met His Pro Gly Arg Leu Thr
            725             730             735 cat ttg cat gaa gga ctt cct gtt aaa aat gga aca aga tac att gca    2256
His Leu His Glu Gly Leu Pro Val Lys Asn Gly Thr Arg Tyr Ile Ala
        740             745             750 gtg tca ttt ata gat ccc taagttattt acttttcatt gaattgaaat           2304
Val Ser Phe Ile Asp Pro
            755 ttatttgga tgaatgactg gcatgaacac gtctttgaag ttgtggctga aagatgaga    2364 ggaatattta aataacatca acagaacaac ttcactttgg gccaaacatt tgaaaaactt  2424
tttataaaaa attgtttgat atttcttaat gtctgctctg agccttaaaa cacag       2479

<210> SEQ ID NO 9
<211> LENGTH: 758
<212> TYPE: PRT
<213> ORGANISM: Rattus rattus

<400> SEQUENCE: 9

Met Gly Gly Cys Thr Val Lys Pro Gln Leu Leu Leu Leu Ala Leu Val
1               5                   10                  15
```

-continued

Leu His Pro Trp Asn Pro Cys Leu Gly Ala Asp Ser Glu Lys Pro Ser
            20                  25                  30

Ser Ile Pro Thr Asp Lys Leu Leu Val Ile Thr Val Ala Thr Lys Glu
        35                  40                  45

Ser Asp Gly Phe His Arg Phe Met Gln Ser Ala Lys Tyr Phe Asn Tyr
    50                  55                  60

Thr Val Lys Val Leu Gly Gln Gly Glu Trp Arg Gly Gly Asp Gly
65                  70                  75                  80

Ile Asn Ser Ile Gly Gly Gly Gln Lys Val Arg Leu Met Lys Glu Val
                85                  90                  95

Met Glu His Tyr Ala Asp Gln Asp Leu Val Val Met Phe Thr Glu
            100                 105                 110

Cys Phe Asp Val Ile Phe Ala Gly Gly Pro Glu Glu Val Leu Lys Lys
        115                 120                 125

Phe Gln Lys Ala Asn His Lys Val Val Phe Ala Ala Asp Gly Ile Leu
    130                 135                 140

Trp Pro Asp Lys Arg Leu Ala Asp Lys Tyr Pro Val Val His Ile Gly
145                 150                 155                 160

Lys Arg Tyr Leu Asn Ser Gly Gly Phe Ile Gly Tyr Ala Pro Tyr Val
                165                 170                 175

Asn Arg Ile Val Gln Gln Trp Asn Leu Gln Asp Asn Asp Asp Gln
            180                 185                 190

Leu Phe Tyr Thr Lys Val Tyr Ile Asp Pro Leu Lys Arg Glu Ala Ile
    195                 200                 205

Asn Ile Thr Leu Asp His Lys Cys Lys Ile Phe Gln Thr Leu Asn Gly
210                 215                 220

Ala Val Asp Glu Val Val Leu Lys Phe Glu Asn Gly Lys Ala Arg Ala
225                 230                 235                 240

Lys Asn Thr Phe Tyr Glu Thr Leu Pro Val Ala Ile Asn Gly Asn Gly
                245                 250                 255

Pro Thr Lys Ile Leu Leu Asn Tyr Phe Gly Asn Tyr Val Pro Asn Ser
            260                 265                 270

Trp Thr Gln Asp Asn Gly Cys Thr Leu Cys Glu Phe Asp Thr Val Asp
    275                 280                 285

Leu Ser Ala Val Asp Val His Pro Asn Val Ser Ile Gly Val Phe Ile
290                 295                 300

Glu Gln Pro Thr Pro Phe Leu Pro Arg Phe Leu Asp Ile Leu Leu Thr
305                 310                 315                 320

Leu Asp Tyr Pro Lys Glu Ala Leu Lys Leu Phe Ile His Asn Lys Glu
                325                 330                 335

Val Tyr His Glu Lys Asp Ile Lys Val Phe Phe Asp Lys Ala Lys His
            340                 345                 350

Glu Ile Lys Thr Ile Lys Ile Val Gly Pro Glu Glu Asn Leu Ser Gln
        355                 360                 365

Ala Glu Ala Arg Asn Met Gly Met Asp Phe Cys Arg Gln Asp Glu Lys
    370                 375                 380

Cys Asp Tyr Tyr Phe Ser Val Asp Ala Asp Val Val Leu Thr Asn Pro
385                 390                 395                 400

Arg Thr Leu Lys Ile Leu Ile Glu Gln Asn Arg Lys Ile Ile Ala Pro
                405                 410                 415

Leu Val Thr Arg His Gly Lys Leu Trp Ser Asn Phe Trp Gly Ala Leu
            420                 425                 430

```
Ser Pro Asp Gly Tyr Tyr Ala Arg Ser Glu Asp Tyr Val Asp Ile Val
        435                 440                 445
Gln Gly Asn Arg Val Gly Val Trp Asn Val Pro Tyr Met Ala Asn Val
    450                 455                 460
Tyr Leu Ile Lys Gly Lys Thr Leu Arg Ser Glu Met Asn Glu Arg Asn
465                 470                 475                 480
Tyr Phe Val Arg Asp Lys Leu Asp Pro Asp Met Ala Leu Cys Arg Asn
                485                 490                 495
Ala Arg Glu Met Thr Leu Gln Arg Glu Lys Asp Ser Pro Thr Pro Glu
            500                 505                 510
Thr Phe Gln Met Leu Ser Pro Pro Lys Gly Val Phe Met Tyr Ile Ser
        515                 520                 525
Asn Arg His Glu Phe Gly Arg Leu Leu Ser Thr Ala Asn Tyr Asn Thr
    530                 535                 540
Ser His Tyr Asn Asn Asp Leu Trp Gln Ile Phe Glu Asn Pro Val Asp
545                 550                 555                 560
Trp Lys Glu Lys Tyr Ile Asn Arg Asp Tyr Ser Lys Ile Phe Thr Glu
                565                 570                 575
Asn Ile Val Glu Gln Pro Cys Pro Asp Val Phe Trp Phe Pro Ile Phe
            580                 585                 590
Ser Glu Lys Ala Cys Asp Glu Leu Val Glu Met Glu His Tyr Gly
        595                 600                 605
Lys Trp Ser Gly Gly Lys His His Asp Ser Arg Ile Ser Gly Gly Tyr
    610                 615                 620
Glu Asn Val Pro Thr Asp Asp Ile His Met Lys Gln Val Asp Leu Glu
625                 630                 635                 640
Asn Val Trp Leu His Phe Ile Arg Glu Phe Ile Ala Pro Val Thr Leu
                645                 650                 655
Lys Val Phe Ala Gly Tyr Tyr Thr Lys Gly Phe Ala Leu Leu Asn Phe
            660                 665                 670
Val Val Lys Tyr Ser Pro Glu Arg Gln Arg Ser Leu Arg Pro His His
        675                 680                 685
Asp Ala Ser Thr Phe Thr Ile Asn Ile Ala Leu Asn Asn Val Gly Glu
    690                 695                 700
Asp Phe Gln Gly Gly Gly Cys Lys Phe Leu Arg Tyr Asn Cys Ser Ile
705                 710                 715                 720
Glu Ser Pro Arg Lys Gly Trp Ser Phe Met His Pro Gly Arg Leu Thr
                725                 730                 735
His Leu His Glu Gly Leu Pro Val Lys Asn Gly Thr Arg Tyr Ile Ala
            740                 745                 750
Val Ser Phe Ile Asp Pro
        755

<210> SEQ ID NO 10
<211> LENGTH: 2479
<212> TYPE: DNA
<213> ORGANISM: Homo sapiens
<220> FEATURE:
<221> NAME/KEY: CDS
<222> LOCATION: (1)..(2211)

<400> SEQUENCE: 10 atg ggg gga tgc acg gtg aag cct cag ctg ctg ctc ctg gcg ctc gtc        48
Met Gly Gly Cys Thr Val Lys Pro Gln Leu Leu Leu Leu Ala Leu Val
1               5                   10                  15 ctc cac ccc tgg aat ccc tgt ctg ggt gcg gac tcg gag aag ccc tcg        96
```

```
              Leu His Pro Trp Asn Pro Cys Leu Gly Ala Asp Ser Glu Lys Pro Ser
                           20                  25                  30 agc atc ccc aca gat aaa tta tta gtc ata act gta gca aca aaa gaa            144
Ser Ile Pro Thr Asp Lys Leu Leu Val Ile Thr Val Ala Thr Lys Glu
         35                  40                  45 agt gat gga ttc cat cga ttt atg cag tca gcc aaa tat ttc aat tat            192
Ser Asp Gly Phe His Arg Phe Met Gln Ser Ala Lys Tyr Phe Asn Tyr
 50                  55                  60 act gtg aag gtc ctt ggt caa gga gaa gaa tgg aga ggt ggt gat gga            240
Thr Val Lys Val Leu Gly Gln Gly Glu Glu Trp Arg Gly Gly Asp Gly
 65                  70                  75                  80 att aat agt att gga ggg ggc cag aaa gtg aga tta atg aaa gaa gtc            288
Ile Asn Ser Ile Gly Gly Gly Gln Lys Val Arg Leu Met Lys Glu Val
             85                  90                  95 atg gaa cac tat gct gat caa gat gat ctg gtt gtc atg ttt act gaa            336
Met Glu His Tyr Ala Asp Gln Asp Asp Leu Val Val Met Phe Thr Glu
            100                 105                 110 tgc ttt gat gtc ata ttt gct ggt ggt cca gaa gaa gtt cta aaa aaa            384
Cys Phe Asp Val Ile Phe Ala Gly Gly Pro Glu Glu Val Leu Lys Lys
            115                 120                 125 ttc caa aag gca aac cac aaa gtg gtc ttt gca gca gat gga att ttg            432
Phe Gln Lys Ala Asn His Lys Val Val Phe Ala Ala Asp Gly Ile Leu
130                 135                 140 tgg cca gat aaa aga cta gca gac aag tat cct gtt gtg cac att ggg            480
Trp Pro Asp Lys Arg Leu Ala Asp Lys Tyr Pro Val Val His Ile Gly
145                 150                 155                 160 aaa cgc tat ctg aat tca gga gga ttt att ggc tat gct cca tat gtc            528
Lys Arg Tyr Leu Asn Ser Gly Gly Phe Ile Gly Tyr Ala Pro Tyr Val
                165                 170                 175 aac cgt ata gtt caa caa tgg aat ctc cag gat aat gat gat gat cag            576
Asn Arg Ile Val Gln Gln Trp Asn Leu Gln Asp Asn Asp Asp Asp Gln
            180                 185                 190 ctc ttt tac act aaa gtt tac att gat cca ctg aaa agg gaa gct att            624
Leu Phe Tyr Thr Lys Val Tyr Ile Asp Pro Leu Lys Arg Glu Ala Ile
        195                 200                 205 aac atc aca ttg gat cac aaa tgc aaa att ttc cag acc tta aat gga            672
Asn Ile Thr Leu Asp His Lys Cys Lys Ile Phe Gln Thr Leu Asn Gly
    210                 215                 220 gct gta gat gaa gtt gtt tta aaa ttt gaa aat ggc aaa gcc aga gct            720
Ala Val Asp Glu Val Val Leu Lys Phe Glu Asn Gly Lys Ala Arg Ala
225                 230                 235                 240 aag aat aca ttt tat gaa aca tta cca gtg gca att aat gga aat gga            768
Lys Asn Thr Phe Tyr Glu Thr Leu Pro Val Ala Ile Asn Gly Asn Gly
                245                 250                 255 ccc acc aag att ctc ctg aat tat ttt gga aac tat gta ccc aat tca            816
Pro Thr Lys Ile Leu Leu Asn Tyr Phe Gly Asn Tyr Val Pro Asn Ser
            260                 265                 270 tgg aca cag gat aat ggc tgc act ctt tgt gaa ttc gat aca gtc gac            864
Trp Thr Gln Asp Asn Gly Cys Thr Leu Cys Glu Phe Asp Thr Val Asp
        275                 280                 285 ttg tct gca gta gat gtc cat cca aac gta tca ata ggt gtt ttt att            912
Leu Ser Ala Val Asp Val His Pro Asn Val Ser Ile Gly Val Phe Ile
    290                 295                 300 gag caa cca acc cct ttt cta cct cgg ttt ctg gac ata ttg ttg aca            960
Glu Gln Pro Thr Pro Phe Leu Pro Arg Phe Leu Asp Ile Leu Leu Thr
305                 310                 315                 320 ctg gat tac cca aaa gaa gca ctt aaa ctt ttt att cat aac aaa gaa           1008
Leu Asp Tyr Pro Lys Glu Ala Leu Lys Leu Phe Ile His Asn Lys Glu
                325                 330                 335
```

```
                                           -continued
gtt tat cat gaa aag gac atc aag gta ttt ttt gat aaa gct aag cat       1056
Val Tyr His Glu Lys Asp Ile Lys Val Phe Phe Asp Lys Ala Lys His
            340                 345                 350 gaa atc aaa act ata aaa ata gta gga cca gaa gaa aat cta agt caa       1104
Glu Ile Lys Thr Ile Lys Ile Val Gly Pro Glu Glu Asn Leu Ser Gln
355                 360                 365 gcg gaa gcc aga aac atg gga atg gac ttt tgc cgt cag gat gaa aag       1152
Ala Glu Ala Arg Asn Met Gly Met Asp Phe Cys Arg Gln Asp Glu Lys
        370                 375                 380 tgt gat tat tac ttt agt gtg gat gca gat gtt gtt ttg aca aat cca       1200
Cys Asp Tyr Tyr Phe Ser Val Asp Ala Asp Val Val Leu Thr Asn Pro
385                 390                 395                 400 agg act tta aaa att ttg att gaa caa aac aga aag atc att gct cct       1248
Arg Thr Leu Lys Ile Leu Ile Glu Gln Asn Arg Lys Ile Ile Ala Pro
                405                 410                 415 ctt gta act cgt cat gga aag ctg tgg tcc aat ttc tgg gga gca ttg       1296
Leu Val Thr Arg His Gly Lys Leu Trp Ser Asn Phe Trp Gly Ala Leu
            420                 425                 430 agt cct gat gga tac tat gca cga tct gaa gat tat gtg gat att gtt       1344
Ser Pro Asp Gly Tyr Tyr Ala Arg Ser Glu Asp Tyr Val Asp Ile Val
        435                 440                 445 caa ggg aat aga gta gga gta tgg aat gtc cca tat atg gct aat gtg       1392
Gln Gly Asn Arg Val Gly Val Trp Asn Val Pro Tyr Met Ala Asn Val
450                 455                 460 tac tta att aaa gga aag aca ctc cga tca gag atg aat gaa agg aac       1440
Tyr Leu Ile Lys Gly Lys Thr Leu Arg Ser Glu Met Asn Glu Arg Asn
465                 470                 475                 480 tat ttt gtt cgt gat aaa ctg gat cct gat atg gct ctt tgc cga aat       1488
Tyr Phe Val Arg Asp Lys Leu Asp Pro Asp Met Ala Leu Cys Arg Asn
                485                 490                 495 gct aga gaa atg act tta caa agg gaa aaa gac tcc cct act ccg gaa       1536
Ala Arg Glu Met Thr Leu Gln Arg Glu Lys Asp Ser Pro Thr Pro Glu
            500                 505                 510 aca ttc caa atg ctc agc ccc cca aag ggt gta ttt atg tac att tct       1584
Thr Phe Gln Met Leu Ser Pro Pro Lys Gly Val Phe Met Tyr Ile Ser
        515                 520                 525 aat aga cat gaa ttt gga agg cta tta tcc act gct aat tac aat act       1632
Asn Arg His Glu Phe Gly Arg Leu Leu Ser Thr Ala Asn Tyr Asn Thr
530                 535                 540 tcc cat tat aac aat gac ctc tgg cag att ttt gaa aat cct gtg gac       1680
Ser His Tyr Asn Asn Asp Leu Trp Gln Ile Phe Glu Asn Pro Val Asp
545                 550                 555                 560 tgg aag gaa aag tat ata aac cgt gat tat tca aag att ttc act gaa       1728
Trp Lys Glu Lys Tyr Ile Asn Arg Asp Tyr Ser Lys Ile Phe Thr Glu
                565                 570                 575 aat ata gtt gaa cag ccc tgt cca gat gtc ttt tgg ttc ccc ata ttt       1776
Asn Ile Val Glu Gln Pro Cys Pro Asp Val Phe Trp Phe Pro Ile Phe
            580                 585                 590 tct gaa aaa gcc tgt gat gaa ttg gta gaa gaa atg gaa cat tac ggc       1824
Ser Glu Lys Ala Cys Asp Glu Leu Val Glu Glu Met Glu His Tyr Gly
        595                 600                 605 aaa tgg tct ggg gga aaa cat cat gat agc cgt ata tct ggt ggt tat       1872
Lys Trp Ser Gly Gly Lys His His Asp Ser Arg Ile Ser Gly Gly Tyr
610                 615                 620 gaa aat gtc cca act gat gat atc cac atg aag caa gtt gat ctg gag       1920
Glu Asn Val Pro Thr Asp Asp Ile His Met Lys Gln Val Asp Leu Glu
625                 630                 635                 640 aat gta tgg ctt cat ttt atc cgg gag ttc att gca cca gtt aca ctg       1968
Asn Val Trp Leu His Phe Ile Arg Glu Phe Ile Ala Pro Val Thr Leu
                645                 650                 655
```

-continued

```
aag gtc ttt gca ggc tat tat acg aag gga ttt gca cta ctg aat ttt    2016
Lys Val Phe Ala Gly Tyr Tyr Thr Lys Gly Phe Ala Leu Leu Asn Phe
        660                 665                 670 gta gta aaa tac tcc cct gaa cga cag cgt tct ctt cgt cct cat cat    2064
Val Val Lys Tyr Ser Pro Glu Arg Gln Arg Ser Leu Arg Pro His His
            675                 680                 685 gat gct tct aca ttt acc ata aac att gca ctt aat aac gtg gga gaa    2112
Asp Ala Ser Thr Phe Thr Ile Asn Ile Ala Leu Asn Asn Val Gly Glu
        690                 695                 700 gac ttt cag gga ggt ggt tgc aaa ttt cta agg tac aat tgc tct att    2160
Asp Phe Gln Gly Gly Gly Cys Lys Phe Leu Arg Tyr Asn Cys Ser Ile
705                 710                 715                 720 gag tca cca cga aaa ggc tgg agc ttc atg cat cct ggg aga ctc aca    2208
Glu Ser Pro Arg Lys Gly Trp Ser Phe Met His Pro Gly Arg Leu Thr
                725                 730                 735 cat ttgcatgaag gacttcctgt taaaaatgga acaagataca ttgcagtgtc         2261
His atttatagat ccctaagtta tttactttc attgaattga aatttatttt ggatgaatga   2321
ctggcatgaa cacgtctttg aagttgtggc tgagaagatg agaggaatat ttaaataaca  2381
tcaacagaac aacttcactt tgggccaaac atttgaaaaa ctttttataa aaaattgttt  2441
gatatttctt aatgtctgct ctgagcctta aaacacag                          2479

<210> SEQ ID NO 11
<211> LENGTH: 737
<212> TYPE: PRT
<213> ORGANISM: Homo sapiens

<400> SEQUENCE: 11

Met Gly Gly Cys Thr Val Lys Pro Gln Leu Leu Leu Ala Leu Val
1               5                   10                  15

Leu His Pro Trp Asn Pro Cys Leu Gly Ala Asp Ser Glu Lys Pro Ser
                20                  25                  30

Ser Ile Pro Thr Asp Lys Leu Leu Val Ile Thr Val Ala Thr Lys Glu
            35                  40                  45

Ser Asp Gly Phe His Arg Phe Met Gln Ser Ala Lys Tyr Phe Asn Tyr
        50                  55                  60

Thr Val Lys Val Leu Gly Gln Gly Glu Glu Trp Arg Gly Gly Asp Gly
65                  70                  75                  80

Ile Asn Ser Ile Gly Gly Gln Lys Val Arg Leu Met Lys Glu Val
                85                  90                  95

Met Glu His Tyr Ala Asp Gln Asp Asp Leu Val Val Met Phe Thr Glu
                100                 105                 110

Cys Phe Asp Val Ile Phe Ala Gly Gly Pro Glu Glu Val Leu Lys Lys
            115                 120                 125

Phe Gln Lys Ala Asn His Lys Val Val Phe Ala Ala Asp Gly Ile Leu
        130                 135                 140

Trp Pro Asp Lys Arg Leu Ala Asp Lys Tyr Pro Val Val His Ile Gly
145                 150                 155                 160

Lys Arg Tyr Leu Asn Ser Gly Gly Phe Ile Gly Tyr Ala Pro Tyr Val
                165                 170                 175

Asn Arg Ile Val Gln Gln Trp Asn Leu Gln Asn Asp Asp Asp Gln
                180                 185                 190

Leu Phe Tyr Thr Lys Val Tyr Ile Asp Pro Leu Lys Arg Glu Ala Ile
        195                 200                 205
```

-continued

```
Asn Ile Thr Leu Asp His Lys Cys Lys Ile Phe Gln Thr Leu Asn Gly
    210                 215                 220
Ala Val Asp Glu Val Val Leu Lys Phe Glu Asn Gly Lys Ala Arg Ala
225                 230                 235                 240
Lys Asn Thr Phe Tyr Glu Thr Leu Pro Val Ala Ile Asn Gly Asn Gly
                245                 250                 255
Pro Thr Lys Ile Leu Leu Asn Tyr Phe Gly Asn Tyr Val Pro Asn Ser
                260                 265                 270
Trp Thr Gln Asp Asn Gly Cys Thr Leu Cys Glu Phe Asp Thr Val Asp
                275                 280                 285
Leu Ser Ala Val Asp Val His Pro Asn Val Ser Ile Gly Val Phe Ile
    290                 295                 300
Glu Gln Pro Thr Pro Phe Leu Pro Arg Phe Leu Asp Ile Leu Leu Thr
305                 310                 315                 320
Leu Asp Tyr Pro Lys Glu Ala Leu Lys Leu Phe Ile His Asn Lys Glu
                325                 330                 335
Val Tyr His Glu Lys Asp Ile Lys Val Phe Phe Asp Lys Ala Lys His
                340                 345                 350
Glu Ile Lys Thr Ile Lys Ile Val Gly Pro Glu Glu Asn Leu Ser Gln
                355                 360                 365
Ala Glu Ala Arg Asn Met Gly Met Asp Phe Cys Arg Gln Asp Glu Lys
    370                 375                 380
Cys Asp Tyr Tyr Phe Ser Val Asp Ala Asp Val Val Leu Thr Asn Pro
385                 390                 395                 400
Arg Thr Leu Lys Ile Leu Ile Glu Gln Asn Arg Lys Ile Ile Ala Pro
                405                 410                 415
Leu Val Thr Arg His Gly Lys Leu Trp Ser Asn Phe Trp Gly Ala Leu
                420                 425                 430
Ser Pro Asp Gly Tyr Tyr Ala Arg Ser Glu Asp Tyr Val Asp Ile Val
    435                 440                 445
Gln Gly Asn Arg Val Gly Val Trp Asn Val Pro Tyr Met Ala Asn Val
    450                 455                 460
Tyr Leu Ile Lys Gly Lys Thr Leu Arg Ser Glu Met Asn Glu Arg Asn
465                 470                 475                 480
Tyr Phe Val Arg Asp Lys Leu Asp Pro Asp Met Ala Leu Cys Arg Asn
                485                 490                 495
Ala Arg Glu Met Thr Leu Gln Arg Glu Lys Asp Ser Pro Thr Pro Glu
                500                 505                 510
Thr Phe Gln Met Leu Ser Pro Pro Lys Gly Val Phe Met Tyr Ile Ser
    515                 520                 525
Asn Arg His Glu Phe Gly Arg Leu Leu Ser Thr Ala Asn Tyr Asn Thr
    530                 535                 540
Ser His Tyr Asn Asn Asp Leu Trp Gln Ile Phe Glu Asn Pro Val Asp
545                 550                 555                 560
Trp Lys Glu Lys Tyr Ile Asn Arg Asp Tyr Ser Lys Ile Phe Thr Glu
                565                 570                 575
Asn Ile Val Glu Gln Pro Cys Pro Asp Val Phe Trp Phe Pro Ile Phe
                580                 585                 590
Ser Glu Lys Ala Cys Asp Glu Leu Val Glu Met Glu His Tyr Gly
                595                 600                 605
Lys Trp Ser Gly Gly Lys His His Asp Ser Arg Ile Ser Gly Gly Tyr
    610                 615                 620
Glu Asn Val Pro Thr Asp Asp Ile His Met Lys Gln Val Asp Leu Glu
```

```
                625                 630                 635                 640
Asn Val Trp Leu His Phe Ile Arg Glu Phe Ile Ala Pro Val Thr Leu
                        645                 650                 655
Lys Val Phe Ala Gly Tyr Tyr Thr Lys Gly Phe Ala Leu Leu Asn Phe
                660                 665                 670
Val Val Lys Tyr Ser Pro Glu Arg Gln Arg Ser Leu Arg Pro His His
            675                 680                 685
Asp Ala Ser Thr Phe Thr Ile Asn Ile Ala Leu Asn Asn Val Gly Glu
        690                 695                 700
Asp Phe Gln Gly Gly Gly Cys Lys Phe Leu Arg Tyr Asn Cys Ser Ile
705                 710                 715                 720
Glu Ser Pro Arg Lys Gly Trp Ser Phe Met His Pro Gly Arg Leu Thr
                725                 730                 735
His

<210> SEQ ID NO 12
<211> LENGTH: 3718
<212> TYPE: DNA
<213> ORGANISM: Rattus rattus
<220> FEATURE:
<221> NAME/KEY: CDS
<222> LOCATION: (222)..(2486)

<400> SEQUENCE: 12
ggctgcgaga agacgacaga aggggtccgt cgtctgctcg gtgcgctcgg gctccgcgct      60
agtccgctca gtgttctcca atcgctttgg tacccacgca gtcctctcat ccgtcctccg     120
ctgccgtccc gggccccacg tctaacccgg tgctcttcgg ggtctccgcg tctcgcgaga     180
agtcctcgcc gcaggcctcg ggctttcggg cttaggggcg g atg ggg gac cgc gga    236
                                              Met Gly Asp Arg Gly
                                                1               5 gtg agg ctg ggg ctg ctg atg ccc atg ctc gcc ctg ctc tcc tgg gcg      284
Val Arg Leu Gly Leu Leu Met Pro Met Leu Ala Leu Leu Ser Trp Ala
                 10                  15                  20 gct agc ctg ggc gta gcg gag gag act ccc tcg cgc atc cca gca gat      332
Ala Ser Leu Gly Val Ala Glu Glu Thr Pro Ser Arg Ile Pro Ala Asp
             25                  30                  35 aag tta tta gtc ata act gta gca acc aaa gaa aac gat gga ttc cac      380
Lys Leu Leu Val Ile Thr Val Ala Thr Lys Glu Asn Asp Gly Phe His
         40                  45                  50 aga ttt atg aat tca gcc aag tat ttc aat tat act gtg aag gtt ctt      428
Arg Phe Met Asn Ser Ala Lys Tyr Phe Asn Tyr Thr Val Lys Val Leu
     55                  60                  65 ggt caa ggg caa gag tgg aga ggt ggt gat ggg atg aac agt att gga      476
Gly Gln Gly Gln Glu Trp Arg Gly Gly Asp Gly Met Asn Ser Ile Gly
 70                  75                  80                  85 ggg ggc cag aag gtg aga tta atg aaa gaa gcc atg gag cac tac gcc      524
Gly Gly Gln Lys Val Arg Leu Met Lys Glu Ala Met Glu His Tyr Ala
                 90                  95                 100 ggt cag gac gat ctg gtc atc ttg ttt act gaa tgt ttt gat gtt ata      572
Gly Gln Asp Asp Leu Val Ile Leu Phe Thr Glu Cys Phe Asp Val Ile
            105                 110                 115 ttt gct ggt ggg cct gaa gaa ctt ctt aaa aag ttc caa aag aca aat      620
Phe Ala Gly Gly Pro Glu Glu Leu Leu Lys Lys Phe Gln Lys Thr Asn
        120                 125                 130 cat aaa atc gtc ttt gca gcg gat gcg ctg ttg tgg cca gat aag cgg      668
His Lys Ile Val Phe Ala Ala Asp Ala Leu Leu Trp Pro Asp Lys Arg
    135                 140                 145
```

```
                                            -continued ctg gca gac aag tat cct ggt gtg cac att ggg aaa cgc tac ctg aat      716
Leu Ala Asp Lys Tyr Pro Gly Val His Ile Gly Lys Arg Tyr Leu Asn
150             155                 160                 165 tct gga ggc ttt att ggc tat gct ccc tac atc agc cgt ctg gtc cag      764
Ser Gly Gly Phe Ile Gly Tyr Ala Pro Tyr Ile Ser Arg Leu Val Gln
            170                 175                 180 cag tgg gat ctg cag gat aat gat gac gac cag ctc ttt tac act aaa      812
Gln Trp Asp Leu Gln Asp Asn Asp Asp Asp Gln Leu Phe Tyr Thr Lys
                185                 190                 195 gtt tac atc gac ccg ctg aaa agg gaa gct ctt aac atc aca ttg gat      860
Val Tyr Ile Asp Pro Leu Lys Arg Glu Ala Leu Asn Ile Thr Leu Asp
                    200                 205                 210 cac aga tgc aaa att ttc cag gcc ttg aat gga gct aca gac gaa gtt      908
His Arg Cys Lys Ile Phe Gln Ala Leu Asn Gly Ala Thr Asp Glu Val
        215                 220                 225 gtt tta aag ttt gaa aat ggt aaa agc aga gtg aag aat aca ttt tat      956
Val Leu Lys Phe Glu Asn Gly Lys Ser Arg Val Lys Asn Thr Phe Tyr
230             235                 240                 245 gaa aca ctg cca gtg gcc atc aat ggg aat ggg ccc acc aaa att ctc     1004
Glu Thr Leu Pro Val Ala Ile Asn Gly Asn Gly Pro Thr Lys Ile Leu
            250                 255                 260 ttg aat tac ttt gga aac tat gtt cca aat tca tgg aca cag gaa aat     1052
Leu Asn Tyr Phe Gly Asn Tyr Val Pro Asn Ser Trp Thr Gln Glu Asn
                265                 270                 275 ggc tgt gct ctt tgt gac ttt gac aca att gac ctg tct aca gta gat     1100
Gly Cys Ala Leu Cys Asp Phe Asp Thr Ile Asp Leu Ser Thr Val Asp
                    280                 285                 290 gtc tat ccg aag gta aca cta ggt gtt ttt att gaa caa cca acc ccc     1148
Val Tyr Pro Lys Val Thr Leu Gly Val Phe Ile Glu Gln Pro Thr Pro
        295                 300                 305 ttt cta cct cgg ttc ctg gac tta ctg tta aca ctg gat tac cct aaa     1196
Phe Leu Pro Arg Phe Leu Asp Leu Leu Leu Thr Leu Asp Tyr Pro Lys
310             315                 320                 325 gaa gca ctt cga ctc ttt gtc cat aat aaa gaa gtt tat cat gaa aag     1244
Glu Ala Leu Arg Leu Phe Val His Asn Lys Glu Val Tyr His Glu Lys
            330                 335                 340 gac atc aaa gcg ttt gtt gat aaa gct aaa cac gac atc agc tct ata     1292
Asp Ile Lys Ala Phe Val Asp Lys Ala Lys His Asp Ile Ser Ser Ile
                345                 350                 355 aaa ata gta gga cca gag gaa aat cta agt caa gcg gaa gcc aga aac     1340
Lys Ile Val Gly Pro Glu Glu Asn Leu Ser Gln Ala Glu Ala Arg Asn
                    360                 365                 370 atg gga atg gat ttc tgc cgt cag gat gaa aag tgt gat tac tac ttt     1388
Met Gly Met Asp Phe Cys Arg Gln Asp Glu Lys Cys Asp Tyr Tyr Phe
        375                 380                 385 agt gtg gat gca gat gtt gtt ttg aca aac cca aga act tta aaa att     1436
Ser Val Asp Ala Asp Val Val Leu Thr Asn Pro Arg Thr Leu Lys Ile
390             395                 400                 405 ttg att gaa caa aac agg aag atc att gcc cct ctt gtg aca cgt cat     1484
Leu Ile Glu Gln Asn Arg Lys Ile Ile Ala Pro Leu Val Thr Arg His
            410                 415                 420 gga aag ttg tgg tcc aac ttc tgg gga gcc ctg agt cct gat gga tac     1532
Gly Lys Leu Trp Ser Asn Phe Trp Gly Ala Leu Ser Pro Asp Gly Tyr
                425                 430                 435 tat gct cgt tct gaa gat tac gta gat atc gtt cag gga aac aga gta     1580
Tyr Ala Arg Ser Glu Asp Tyr Val Asp Ile Val Gln Gly Asn Arg Val
                    440                 445                 450 gga ata tgg aat gtc cca tac atg gct aat gtg tac tta att caa ggg     1628
Gly Ile Trp Asn Val Pro Tyr Met Ala Asn Val Tyr Leu Ile Gln Gly
        455                 460                 465
```

```
aag acg ctg cga tca gag atg agt gaa agg aac tat ttt gtg cgt gat      1676
Lys Thr Leu Arg Ser Glu Met Ser Glu Arg Asn Tyr Phe Val Arg Asp
470                 475                 480                 485 aag ttg gat ccc gac atg tct ctc tgc cgc aat gct cga gac atg acc      1724
Lys Leu Asp Pro Asp Met Ser Leu Cys Arg Asn Ala Arg Asp Met Thr
                490                 495                 500 tta caa agg gaa aaa gac tcc ccc act ccg gaa aca ttc caa atg ctc      1772
Leu Gln Arg Glu Lys Asp Ser Pro Thr Pro Glu Thr Phe Gln Met Leu
505                 510                 515 agc ccc cca aag ggt gtg ttt atg tac att tct aac aga cat gaa ttt      1820
Ser Pro Pro Lys Gly Val Phe Met Tyr Ile Ser Asn Arg His Glu Phe
        520                 525                 530 gga cgg ctg ata tca act gct aat tac aac act tcc cat ctc aac aat      1868
Gly Arg Leu Ile Ser Thr Ala Asn Tyr Asn Thr Ser His Leu Asn Asn
535                 540                 545 gac ctc tgg cag atc ttt gaa aat ccc gtg gat tgg aag gaa aaa tat      1916
Asp Leu Trp Gln Ile Phe Glu Asn Pro Val Asp Trp Lys Glu Lys Tyr
550                 555                 560                 565 ata aac cgt gac tat tca aag att ttc act gaa aat ata gtc gag cag      1964
Ile Asn Arg Asp Tyr Ser Lys Ile Phe Thr Glu Asn Ile Val Glu Gln
                570                 575                 580 ccc tgt cca gat gtc ttc tgg ttt ccc ata ttt tct gaa cga gcc tgt      2012
Pro Cys Pro Asp Val Phe Trp Phe Pro Ile Phe Ser Glu Arg Ala Cys
            585                 590                 595 gac gag ttg gta gaa gaa atg gaa cat tac ggc aag tgg tcc ggg gga      2060
Asp Glu Leu Val Glu Glu Met Glu His Tyr Gly Lys Trp Ser Gly Gly
            600                 605                 610 aag cat cat gac agc cgt ata tct ggt ggc tat gaa aat gtc cca acg      2108
Lys His His Asp Ser Arg Ile Ser Gly Gly Tyr Glu Asn Val Pro Thr
615                 620                 625 gat gac att cat atg aag cag att gac ctg gag aac gtc tgg ctt cac      2156
Asp Asp Ile His Met Lys Gln Ile Asp Leu Glu Asn Val Trp Leu His
630                 635                 640                 645 ttt atc cga gag ttt atc gct cca gtt acc ctg aag gtc ttc gcg gga      2204
Phe Ile Arg Glu Phe Ile Ala Pro Val Thr Leu Lys Val Phe Ala Gly
                650                 655                 660 tat tac acc aag gga ttt gcc ctg ctg aac ttc gta gtg aag tac tcg      2252
Tyr Tyr Thr Lys Gly Phe Ala Leu Leu Asn Phe Val Val Lys Tyr Ser
            665                 670                 675 ccc gaa aga cag cgc tcg ctc cgg cct cac cac gat gcg tca acc ttc      2300
Pro Glu Arg Gln Arg Ser Leu Arg Pro His His Asp Ala Ser Thr Phe
            680                 685                 690 acc atc aac att gct cta aat aat gta gga gag gat ttt cag gga ggt      2348
Thr Ile Asn Ile Ala Leu Asn Asn Val Gly Glu Asp Phe Gln Gly Gly
695                 700                 705 gga tgc aaa ttc cta agg tat aat tgc tcc atc gaa tcc ccc cga aaa      2396
Gly Cys Lys Phe Leu Arg Tyr Asn Cys Ser Ile Glu Ser Pro Arg Lys
710                 715                 720                 725 ggc tgg agc ttc atg cat cct ggg agg ctt act cat cta cac gaa ggg      2444
Gly Trp Ser Phe Met His Pro Gly Arg Leu Thr His Leu His Glu Gly
                730                 735                 740 ctt cct gtc aaa aat gga aca aga tac att gca gtc tca ttt                2486
Leu Pro Val Lys Asn Gly Thr Arg Tyr Ile Ala Val Ser Phe
            745                 750                 755 atcgatccct aagttattga ctgaacttaa actgagtggc tctttgagat ggatgactgg      2546
cgggaacatg tctctgaagt tgtacttgag aagacgagag gaatatttaa ataatgtcac      2606
cagaacaacg tcactttggg ccaagcattt gaaaactttt tatataaatt tgttttatgt      2666
```

```
ttcttaacgt ctgctctgag ccttaaaaca caggttgaag aagaagagag aggaaaaaag    2726
tgaaagttgg tatttatttc tgtgctttaa ttgtctatga aaatgatgac attttataaa    2786
atgtttaggt acaaaggcat gaatgataat cagtaagcct aataatattt tcttatttaa    2846
ggagaacctg agaagatttt attttcagt gggagaaata tggaaatgg ttctaaatga     2906 gggtcggcac gtctggaagc ccgggattct gacgcgtact gaatttatgt gtaacttta     2966 agccatgctg acctccgggt agattcgctt ttcagtgata aggaagaaaa cccaaagaaa    3026
atattgcaca gaggctttcc tcaagcagcc tgggcagatg ccagtggaa gcccatccac    3086 tggagatcct cagcttgtga ggcaggtgct cctgtccgtt ggaaactggg ccctgtgtg    3146 tctccagggc aagctctcag gggaagctca catctgcctg ctttacagag tgcttcaggc    3206
gtcagctcca agtcaaacag gatgtgtttc cttctgtttt tccctctaa ttatagaaaa     3266 tagtaaggaa aaatatcagt ttcattgaga ttagtagtac attttactat cttcttttt     3326 aacgattaag tacttgaatt ttatatcagg aaaatagttt ttgagcctgt tcttaccttt    3386
ggccgtagtt ggtagttggt ctctttgttt ttcctggagg aggggcattt ctttttcctca   3446 tcataaacta ctttctcatt cttagtcttg ttattactt tcctctaccc cactttttaa     3506
aaattcccac agcaaaattt ttattttgaat ttttaatatt tctctgaatg aggtttaaat   3566
atctttatta gagctactgt ttttaatttta aaggttaaac ttgaagaaag tctttattca   3626
tggtgccaaa atgcattttt ctaactctgt gtgttagaaa ataatgaaaa ataaaataac    3686
ttacaataaa aaaaaaaaaa aaaaaaaaa aa                                   3718
```

<210> SEQ ID NO 13
<211> LENGTH: 755
<212> TYPE: PRT
<213> ORGANISM: Rattus rattus

<400> SEQUENCE: 13

```
Met Gly Asp Arg Gly Val Arg Leu Gly Leu Leu Met Pro Met Leu Ala
1               5                   10                  15

Leu Leu Ser Trp Ala Ala Ser Leu Gly Val Ala Glu Glu Thr Pro Ser
            20                  25                  30

Arg Ile Pro Ala Asp Lys Leu Leu Val Ile Thr Val Ala Thr Lys Glu
        35                  40                  45

Asn Asp Gly Phe His Arg Phe Met Asn Ser Ala Lys Tyr Phe Asn Tyr
    50                  55                  60

Thr Val Lys Val Leu Gly Gln Gly Gln Glu Trp Arg Gly Gly Asp Gly
65                  70                  75                  80

Met Asn Ser Ile Gly Gly Gly Gln Lys Val Arg Leu Met Lys Glu Ala
                85                  90                  95

Met Glu His Tyr Ala Gly Gln Asp Asp Leu Val Ile Leu Phe Thr Glu
            100                 105                 110

Cys Phe Asp Val Ile Phe Ala Gly Gly Pro Glu Glu Leu Leu Lys Lys
        115                 120                 125

Phe Gln Lys Thr Asn His Lys Ile Val Phe Ala Ala Asp Ala Leu Leu
    130                 135                 140

Trp Pro Asp Lys Arg Leu Ala Asp Lys Tyr Pro Gly Val His Ile Gly
145                 150                 155                 160

Lys Arg Tyr Leu Asn Ser Gly Gly Phe Ile Gly Tyr Ala Pro Tyr Ile
                165                 170                 175

Ser Arg Leu Val Gln Gln Trp Asp Leu Gln Asp Asn Asp Asp Asp Gln
            180                 185                 190
```

```
Leu Phe Tyr Thr Lys Val Tyr Ile Asp Pro Leu Lys Arg Glu Ala Leu
            195                 200                 205

Asn Ile Thr Leu Asp His Arg Cys Lys Ile Phe Gln Ala Leu Asn Gly
        210                 215                 220

Ala Thr Asp Glu Val Val Leu Lys Phe Glu Asn Gly Lys Ser Arg Val
225                 230                 235                 240

Lys Asn Thr Phe Tyr Glu Thr Leu Pro Val Ala Ile Asn Gly Asn Gly
                245                 250                 255

Pro Thr Lys Ile Leu Leu Asn Tyr Phe Gly Asn Tyr Val Pro Asn Ser
            260                 265                 270

Trp Thr Gln Glu Asn Gly Cys Ala Leu Cys Asp Phe Asp Thr Ile Asp
        275                 280                 285

Leu Ser Thr Val Asp Val Tyr Pro Lys Val Thr Leu Gly Val Phe Ile
            290                 295                 300

Glu Gln Pro Thr Pro Phe Leu Pro Arg Phe Leu Asp Leu Leu Leu Thr
305                 310                 315                 320

Leu Asp Tyr Pro Lys Glu Ala Leu Arg Leu Phe Val His Asn Lys Glu
                325                 330                 335

Val Tyr His Glu Lys Asp Ile Lys Ala Phe Val Asp Lys Ala Lys His
            340                 345                 350

Asp Ile Ser Ser Ile Lys Ile Val Gly Pro Glu Glu Asn Leu Ser Gln
            355                 360                 365

Ala Glu Ala Arg Asn Met Gly Met Asp Phe Cys Arg Gln Asp Glu Lys
        370                 375                 380

Cys Asp Tyr Tyr Phe Ser Val Asp Ala Asp Val Val Leu Thr Asn Pro
385                 390                 395                 400

Arg Thr Leu Lys Ile Leu Ile Glu Gln Asn Arg Lys Ile Ile Ala Pro
                405                 410                 415

Leu Val Thr Arg His Gly Lys Leu Trp Ser Asn Phe Trp Gly Ala Leu
            420                 425                 430

Ser Pro Asp Gly Tyr Tyr Ala Arg Ser Glu Asp Tyr Val Asp Ile Val
        435                 440                 445

Gln Gly Asn Arg Val Gly Ile Trp Asn Val Pro Tyr Met Ala Asn Val
        450                 455                 460

Tyr Leu Ile Gln Gly Lys Thr Leu Arg Ser Glu Met Ser Glu Arg Asn
465                 470                 475                 480

Tyr Phe Val Arg Asp Lys Leu Asp Pro Asp Met Ser Leu Cys Arg Asn
                485                 490                 495

Ala Arg Asp Met Thr Leu Gln Arg Glu Lys Asp Ser Pro Thr Pro Glu
            500                 505                 510

Thr Phe Gln Met Leu Ser Pro Pro Lys Gly Val Phe Met Tyr Ile Ser
        515                 520                 525

Asn Arg His Glu Phe Gly Arg Leu Ile Ser Thr Ala Asn Tyr Asn Thr
        530                 535                 540

Ser His Leu Asn Asn Asp Leu Trp Gln Ile Phe Glu Asn Pro Val Asp
545                 550                 555                 560

Trp Lys Glu Lys Tyr Ile Asn Arg Asp Tyr Ser Lys Ile Phe Thr Glu
                565                 570                 575

Asn Ile Val Glu Gln Pro Cys Pro Asp Val Phe Trp Phe Pro Ile Phe
            580                 585                 590

Ser Glu Arg Ala Cys Asp Glu Leu Val Glu Glu Met Glu His Tyr Gly
        595                 600                 605
```

```
Lys Trp Ser Gly Gly Lys His His Asp Ser Arg Ile Ser Gly Gly Tyr
        610                 615                 620

Glu Asn Val Pro Thr Asp Asp Ile His Met Lys Gln Ile Asp Leu Glu
625                 630                 635                 640

Asn Val Trp Leu His Phe Ile Arg Glu Phe Ile Ala Pro Val Thr Leu
                645                 650                 655

Lys Val Phe Ala Gly Tyr Tyr Thr Lys Gly Phe Ala Leu Leu Asn Phe
            660                 665                 670

Val Val Lys Tyr Ser Pro Glu Arg Gln Arg Ser Leu Arg Pro His His
        675                 680                 685

Asp Ala Ser Thr Phe Thr Ile Asn Ile Ala Leu Asn Asn Val Gly Glu
690                 695                 700

Asp Phe Gln Gly Gly Gly Cys Lys Phe Leu Arg Tyr Asn Cys Ser Ile
705                 710                 715                 720

Glu Ser Pro Arg Lys Gly Trp Ser Phe Met His Pro Gly Arg Leu Thr
                725                 730                 735

His Leu His Glu Gly Leu Pro Val Lys Asn Gly Thr Arg Tyr Ile Ala
            740                 745                 750

Val Ser Phe
        755

<210> SEQ ID NO 14
<211> LENGTH: 1486
<212> TYPE: DNA
<213> ORGANISM: Homo sapiens
<220> FEATURE:
<221> NAME/KEY: CDS
<222> LOCATION: (1)..(396)

<400> SEQUENCE: 14 gct ctg tac gcg gcg ctg gcc gcc ttg gag gag cac cgg cgg gtc agc      48
Ala Leu Tyr Ala Ala Leu Ala Ala Leu Glu Glu His Arg Arg Val Ser
1               5                   10                  15 cac ggt gag ggc ggc ggg gag gag gcg gcg gcc gcc gcc cgg gaa agg      96
His Gly Glu Gly Gly Gly Glu Glu Ala Ala Ala Ala Ala Arg Glu Arg
            20                  25                  30 gga tcg gcg tcc ggg gaa ccc ccg tct ggc tcc ggc cgc ggc aag aag     144
Gly Ser Ala Ser Gly Glu Pro Pro Ser Gly Ser Gly Arg Gly Lys Lys
        35                  40                  45 atc ttc ggc tgc tcc gag tgc gag aag ctg ttc cgc tca ccg cga gac     192
Ile Phe Gly Cys Ser Glu Cys Glu Lys Leu Phe Arg Ser Pro Arg Asp
50                  55                  60 ctg gag cgg cac gtg ctg gtg cac act ggc gag aag ccg ttc ccg tgc     240
Leu Glu Arg His Val Leu Val His Thr Gly Glu Lys Pro Phe Pro Cys
65                  70                  75                  80 ctg gag tgc ggc aag ttc ttc cgc cac gag tgc tac ctc aag cgc cac     288
Leu Glu Cys Gly Lys Phe Phe Arg His Glu Cys Tyr Leu Lys Arg His
                85                  90                  95 cga ctg ctg cac ggc acc gag cgg ccc ttc cct tgc cac atc tgc ggc     336
Arg Leu Leu His Gly Thr Glu Arg Pro Phe Pro Cys His Ile Cys Gly
            100                 105                 110 aag ggc ttc atc acg ctc agc aac ctc tcc agg cac ctg aag ctg cac     384
Lys Gly Phe Ile Thr Leu Ser Asn Leu Ser Arg His Leu Lys Leu His
        115                 120                 125 cgg ggc atg gac tgactgccag gctgcgtgcg ccctgccctc acccagcct          436
Arg Gly Met Asp
130 cctggactcg gcctggacca ggggaccctcg ggactgcgcg tgaggccccg gccctccaaa   496
```

```
tccaaatcca gacgcaggcc ctgaaatgag gggaccctga ctggagaggt ggggggccacc        556 aaaaacccac aaaggccccg gagctggggg accacaaaca aacagggtcc ttagctgggg        616
caggggagcc caaatctagg gagagactcc tgagcctgag gtccctggaa tgagtgtggg        676
tagccgtaag tccccaagac atggggactt tgcagtgagc aatgggtctc cacaagtacc        736
tctcatcttg agagccctaa tactaaaaga tgggcaccca ccccaccaa gggaagactg         796 ccccattccc tgagagccat cattcctaac gaccttgatc tggagaatgt ggagggagca        856
tgtccctgaa ttttcctaga tccctccaaa tgccacccac cagagtcact ggtgaccca         916 gaaaatggat atagccgaaa tctgcctttc ccctttttca ttccctgtgc tgaaagaggg        976
accagggtag atgccccctg ccctcgaatc cccctcccc gactgtggaa tggatcgacc        1036
ctaacgatct tccccgcccc aaacactaga atagactggc ctgaaatccc cttgcccagt       1096
agaatggact gatctatgtg cacacacccc catcacatgg aatgggctgg tctaggctgt       1156
ggcctgccac cttccttaga gtaataggg ggacactcc ttttttttc ctgtagggtg         1216 tgggccggtc cacgcaattt tttatcctgt gaactcattt gagtgggagg tggtggacac       1276
ctggggtttc cttccctctc tccgtagcat ccgttggtct ttctctccat ctctgttggt       1336
ttgtctgtct ctgtcttcct cccaatccct aggggaaggg ggcatttggc tagggggtgc       1396
ccctgtgagc ctcgaccttg cccctcgtc cctctcccca gtgtttccag gacccccaat        1456
aaaccttgtc ctgtcaaaaa aaaaaaaaaa                                        1486

<210> SEQ ID NO 15
<211> LENGTH: 132
<212> TYPE: PRT
<213> ORGANISM: Homo sapiens

<400> SEQUENCE: 15

Ala Leu Tyr Ala Ala Leu Ala Ala Leu Glu Glu His Arg Arg Val Ser
1               5                   10                  15

His Gly Glu Gly Gly Gly Glu Ala Ala Ala Ala Arg Glu Arg
            20                  25                  30

Gly Ser Ala Ser Gly Glu Pro Pro Ser Gly Ser Gly Arg Gly Lys Lys
        35                  40                  45

Ile Phe Gly Cys Ser Glu Cys Glu Lys Leu Phe Arg Ser Pro Arg Asp
    50                  55                  60

Leu Glu Arg His Val Leu Val His Thr Gly Glu Lys Pro Phe Pro Cys
65                  70                  75                  80

Leu Glu Cys Gly Lys Phe Phe Arg His Glu Cys Tyr Leu Lys Arg His
                85                  90                  95

Arg Leu Leu His Gly Thr Glu Arg Pro Phe Pro Cys His Ile Cys Gly
            100                 105                 110

Lys Gly Phe Ile Thr Leu Ser Asn Leu Ser Arg His Leu Lys Leu His
        115                 120                 125

Arg Gly Met Asp
    130

<210> SEQ ID NO 16
<211> LENGTH: 580
<212> TYPE: DNA
<213> ORGANISM: Homo sapiens

<400> SEQUENCE: 16 tttcttttt tctttcggcg tctgcggtgc tcggaagtgt ggtacttctc ctagttgcag          60
```

-continued

| | |
|---|---|
| tcaggcttca tacgctattg tcctgcccgt tagagcagcc agcgggtaca gaatggattt | 120 |
| tggaagaggg agtcaccact ggacctccaa ggaagccacg tgcagacatc tacaaccttc | 180 |
| gatctcctga cgagtttatt gttggccaaa accaggcttt gattgaacca ggatgaatgc | 240 |
| gggtgttgga agtagaatat atatatacat ataaaattgg ttgggagcca cgtgtaccag | 300 |
| tgtgtgttga tcttggcttg attcagtctg ccttgtaaca gaaactggcg atggaatatg | 360 |
| agaggagccc tctggaaaga aaaggacaga ccctgtgctt tcatgaaagt gaagatctgg | 420 |
| ctgaaccagt tccacaaggt tactgtatac atagcctgag tttaaaaggc tgtgcccact | 480 |
| tcaagaatgt cattgttaga ctttgaaatt tctaactgcc tacctgcata agaaaataa | 540 |
| aatcttttaa atcaaaaaaa aaaaaaaaaa aaaaaaaaa | 580 |

<210> SEQ ID NO 17
<211> LENGTH: 120
<212> TYPE: PRT
<213> ORGANISM: Homo sapiens

<400> SEQUENCE: 17

```
Met Tyr Thr Val Thr Leu Trp Asn Trp Phe Ser Gln Ile Phe Thr Phe
1               5                   10                  15

Met Lys Ala Gln Gly Leu Ser Phe Ser Phe Gln Arg Ala Pro Leu Ile
            20                  25                  30

Phe His Arg Gln Phe Leu Leu Gln Gly Arg Leu Asn Gln Ala Lys Ile
        35                  40                  45

Asn Thr His Trp Tyr Thr Trp Leu Pro Thr Asn Phe Ile Cys Ile Tyr
    50                  55                  60

Ile Phe Tyr Phe Gln His Pro His Ser Ser Trp Phe Asn Gln Ser Leu
65                  70                  75                  80

Val Leu Ala Asn Asn Lys Leu Val Arg Arg Ser Lys Val Val Asp Val
                85                  90                  95

Cys Thr Trp Leu Pro Trp Arg Ser Ser Gly Asp Ser Leu Phe Gln Asn
            100                 105                 110

Pro Phe Cys Thr Arg Trp Leu Leu
        115                 120
```

<210> SEQ ID NO 18
<211> LENGTH: 4342
<212> TYPE: DNA
<213> ORGANISM: Homo sapiens

<400> SEQUENCE: 18

| | |
|---|---|
| ggcacgagag gcacagcacg acctctatgc agacaagtga actgtagaaa ctgattactg | 60 |
| ctccaccaag aagcccccat aagagtggtt atcctggaca cagaagtgtt gaattgaaat | 120 |
| ccacagagca ttttacaaga gttctgacct ggatggggta aacctcagtg cacttctttt | 180 |
| ctgttggcct cagtattact ggattgaaga attgctgctt cttgttagga ggttcatttc | 240 |
| acttatcatt acttacaact tcatactcaa agcactgaga atttcaagtg gagtatattg | 300 |
| aagtagactt cagtttcttt gcatcatttc tgtattcaat ttttttaatt atttcataac | 360 |
| cctattgagt gttttttaac taaattaaca tggctcgaat gaaccgccca gctcctgtgg | 420 |
| aagtcacata caagaacatg agatttctta ttacacacaa tccaaccaat gcgaccttaa | 480 |
| acaaatttat agaggaactt aagaagtatg agttaccac aatagtaaga gtatgtgaag | 540 |
| caacttatga cactactctt gtggagaaag aaggtatcca tgttcttgat tggccttttg | 600 |
| atgatggtgc accaccatcc aaccagattg ttgatgactg ggtaagtctt gtgaaaatta | 660 |

```
agtttcgtga agaacctggt tgttgtattg ctgttcattg cgttgcaggc cttgggagag    720
ctccagtact tgttgcccta gcattaattg aaggtggaat gaaatacgaa gatgcagtac    780
aattcataag acaaaagcgg cgtggagctt ttaacagcaa gcaacttctg tatttggaga    840
agtatcgtcc taaaatgcgg ctgcgtttca agattccaa cggtcataga aacaactgtt     900
gcattcaata aaattggggt gcctaatgct actggaagtg gaacttgaga tagggcctaa    960
tttgttatac atattagcca acatgttggc ttagtaagtc taatgaagct tccataggag   1020
tattgaaagg cagttttacc aggcctcaag ctagacagat ttggcaacct ctgtatttgg   1080
gttacagtca acctatttgg atacttggca aaagattctt gctgtcagca tataaaatgt   1140
gcttgtcatt tgtatcaatt gacctttccc caaatcatgc agtattgagt tatgacttgt   1200
taaatctatt cccatgccag aatcttatca atacataaga aatttaggaa gattaggtgc   1260
caaaataccc agcacaatac ttgtatattt ttagtaccat acagaagtaa atcccagga    1320 actatgaaca ctagacctta tgtggtttat tccttcaatc atttcaaaca ttgaaagtag   1380
ggcctacatg gttatttgcc tgctcacttt atgtttacat ctcccacatt cataccaata   1440
tacgtcaggt ttgcttaacc attgattttt tttttttta ccaagtctta cagtgattat    1500
tttacgtgtt tccatgtatc tcactttgtg ctgtattaaa aaaacctcca tttgaaaat    1560 ctacgttgta cagaagcaca tgtctttaat gtcttcagac aaaaaagcct tacattaatt   1620
taatgtttgc actctgaggt gcaacttaac agggagggcc tgagaaaaga atgggagggg   1680
gctattaatt attttttagca aaatgttgcc tttgtcttgt gcaaacatgt agaatatgct   1740
ctttaattta gtaaaatatt ttttttaaaag gtagagatgc tttggtattg gtatcataaa   1800
cttcctgaaa ttcttgaatt tttttcccat actatcaaga agtgtgttta ccacttattt   1860
ttgtttgaaa gtgtgatttt tttttttcctt cccaacctct ccttgcaaaa aaagaaatgg   1920
gtttctgcta atgaattgag cagacatcta atattttata tgccttttga gctgtgtaac   1980
ttaatatttg gatacttgac aatttgtttt attatgtaat tgataaaatg gtgatgtgta   2040
ttaatgttag ttcaaccata tatttatact gtctggggat gtgtggttat agttctgtgg   2100
gagaaataat tttgtcagtg ttcaccagct tgtaaaaact tagtgcgaga gctgaaacat   2160
ctaaataaat aatgacatgc atttatcatc attgagattg gtttgcttaa aattaactta   2220
ttttgtagaa gacaaaatga attgcacttc acttaatgtg tgtcctcatc tttttacaaa   2280
taaatgaagg attataaatg atgtcagcat tttagtaaac ttttagacaa aatttgttag   2340
ggtcattcat gaaaacttta atactaaaag cactttccat tatatacttt ttaaaggtct   2400
agataatttt gaaccaattt attattgtgt actgaggaga ataatgtat agtagaggac    2460 agccttggtt tgtaaagctc agttccacta gttcatggtt ttgtgcaact tttgagcctc   2520
agttttctcc tttgcaaatt aataattaca tacctttata gatttgaaa ttaatttaaa    2580 tattagtatt tggacatgaa ggcttaatgt taagtttcct ttaatgatcc acaataatcc   2640
ctttgatcac gttaatctaa atctagatgt cttttgtctaa tttttttttga atagcagtta   2700 taaatgtaaa ggactcaaag tttaagtaaa aagtgatact ccaccttgtg tttcaaagaa   2760
tttagttcca cctcttcata ccagtttaac acttaatata tttcattgga ttttagacag   2820
ggcaaaagga agaacagggg cctctggagg cccttggtta tttaaatctt ggattatttg   2880
tgatagtaat cacaaatttt tggctaattt ttaacctgag gttttgtttt ttttttttaaa   2940 ggaaatgcag cctagtcttg agaacataat tttatataat caattactaa atgttaaact   3000
```

```
attaccacac agcccataaa acagcatttg cgtttattga gagagaggat gtgccatcat   3060
gattaatgaa aactatcttt tgagtttgaa aagaaattaa tttgcagtgt ttggattgta   3120
tatatggtgc taaaaataaa ttaatttact ttataaacct tatctgtaca ttatacgatg   3180
tgatgaaatt tgcttttttat ccaaatattt tgtatcttgt aaatatggct aattatagga   3240
atgcctataa tacatcttag attccttata tctaataaga gttcaaagag ttatgagttg   3300
aagtcttgaa tgcaggaaac tatctgatag tgttctaaaa tttggttact tgggtttgga   3360
taccctttagt gggatgatgt aaatagaggc tagctaccta ggcttgtcta tagcaaccat   3420
aatgttgatg taagtaatgc ggttactgaa tcataagaaa atgccatctc tttttagttg   3480
aaggaaaact ctggaagtag gtgccattgg tcattctgca gtgcactgca accattgttt   3540
cccctagtgc cctcttttcc ctagggcatt gctctcctat tcccacgcct aacacagct   3600
ctatacctag aagcagccag cccaggcatg cagtcacatt taatcacatc cccttctag   3660
agtgcttcaa aatgatgtag tccctcaact tggctaaaga atctcaatct cttgaaattt   3720
atttttttaa tgtcatattc atctggtaaa tatctactgt ttgccaggca tttaagaata   3780
tggcaaagaa cataaaagat ggtgtcacca gattttggtc accatgagt acccgacccg   3840
ttgccatgat taagagagaa tgctttctat tggagtttca ggaaatataa tttgagaata   3900
ctttaaaggg aagtggaagt ataagtgaat gatattttttc ttttacatgt aaacaatgaa   3960
gttatttcaa agttaagttt taaacaaaat ccatgaagta gtgtctgcca tacatgttaa   4020
tattctacat tcttgcttcc cttaaattaa tatgtttgtg tgtatatatg tgcctcacac   4080
ctgaattgaa aattaaagac tggttttaaaa gtggtttaaaa agtgacattt aatgtttctc   4140
cattacgttt gggggtaacca gcctaagtgg aatcttggaa ggaaagtaag ggaaaaactt   4200
gtatttgcct tcaatgaatt aaaccagtga tatgtttaac gtatgaatga aaggattgat   4260
ggtgattttta taattatata tattgccgca gtaaccagtt aataaattga tagctaccat   4320
ttaaaaaaaa aaaaaaaaaa aa                                          4342
```

<210> SEQ ID NO 19
<211> LENGTH: 985
<212> TYPE: DNA
<213> ORGANISM: Homo sapiens

<400> SEQUENCE: 19

```
gccaagaatt cggcacgagg agtgggtatc tgagttagtc agtttttacca tttataaaat    60
gtttggtgga ggaaattgaa actaattgct aaattgttag taaccagtgc attaactagg   120
accctactga gtggactgaa agaatcgaaa atgtttaact ggttgagagg caatgatgtt   180
gcaaatgggg tattcttcaa agctccttct ttttttaaat cttcaaaggc aattattctg   240
aatgtaaact acagaccaaa ttgcagtctt ctgtaagcat ttcagagatt acctcaaata   300
ttttttgatt aaaaaactct tccgtggtct tttgtgcttc agaactaccc agtacaacag   360
ggtcttcagc ctgctcagga tctctaaaga gagctagcac acagtcagcc aactttggct   420
gcttcaactc ctaggaacaa gaaatgatgc tgagataatt tgtctggcag gtattatcag   480
cccacaatga ctgctgtcat ttagcctcaa aatgtttatt ttttttttta caatgctgta   540
tttcttttaga accttcctat tccgagtgtg acccctaggc cagccccata gacttcccct   600
ggggacttgt cagaaatgca taatttttagg ccccaccca gacctgttgg accagaatct   660
tcatttaaca agatgcccag gtgattcatt catgtttgag aagctctgct ttaaatcact   720
aaagcagtta ctgagtaatt actaccatca tgactctgaa gagctcctat agccttcaaa   780
```

```
tgcacctaac tctactctaa aggcaaatgt cctcactggg aaatctgatc tgctgtttca    840
gagaagtgca gggctacaca gtgtcttaca ctcctatcta ttgatgtttc ttggttttgc    900
ctggtaatct gctgcttaaa tggattattt gatgacatat tgatattaaa acagtcctat    960
ttttagaaaa aaaaaaaaaa aaaaa                                         985
```

<210> SEQ ID NO 20
<211> LENGTH: 6
<212> TYPE: PRT
<213> ORGANISM: Artificial Sequence
<220> FEATURE:
<223> OTHER INFORMATION: Repeated unit in SEQ ID NO:1
<220> FEATURE:
<221> NAME/KEY: misc_feature
<222> LOCATION: (3)..(3)
<223> OTHER INFORMATION: Xaa is Asp or Ser

<400> SEQUENCE: 20

Gly Gly Xaa Phe Gly Gly
1               5

<210> SEQ ID NO 21
<211> LENGTH: 551
<212> TYPE: PRT
<213> ORGANISM: Homo sapiens

<400> SEQUENCE: 21

Met Ala Glu Gly Glu Asn Glu Val Arg Trp Asp Gly Leu Cys Ser Arg
1               5                   10                  15

Asp Ser Thr Thr Arg Glu Thr Ala Leu Glu Asn Ile Arg Gln Thr Ile
            20                  25                  30

Leu Arg Lys Thr Glu Tyr Leu Arg Ser Val Lys Glu Thr Pro His Arg
        35                  40                  45

Pro Ser Asp Gly Leu Ser Asn Thr Glu Ser Ser Asp Gly Leu Asn Lys
    50                  55                  60

Leu Leu Ala His Leu Leu Met Leu Ser Lys Arg Cys Pro Phe Lys Asp
65                  70                  75                  80

Val Arg Glu Lys Ser Glu Phe Ile Leu Lys Ser Ile Gln Glu Leu Gly
                85                  90                  95

Ile Arg Ile Pro Arg Pro Leu Gly Gln Gly Pro Ser Arg Phe Ile Pro
            100                 105                 110

Glu Lys Glu Ile Leu Gln Val Gly Ser Glu Asp Ala Gln Met His Ala
        115                 120                 125

Leu Phe Ala Asp Ser Phe Ala Ala Leu Gly Arg Leu Asp Asn Ile Thr
    130                 135                 140

Leu Val Met Val Phe His Pro Gln Tyr Leu Glu Ser Phe Leu Lys Thr
145                 150                 155                 160

Gln His Tyr Leu Leu Gln Met Asp Gly Pro Leu Pro Leu His Tyr Arg
                165                 170                 175

His Tyr Ile Gly Ile Met Ala Ala Ala Arg His Gln Cys Ser Tyr Leu
            180                 185                 190

Val Asn Leu His Val Asn Asp Phe Leu His Val Gly Gly Asp Pro Lys
        195                 200                 205

```
Trp Leu Asn Gly Leu Glu Asn Ala Pro Gln Lys Leu Gln Asn Leu Gly
    210                 215                 220

Glu Leu Asn Lys Val Leu Ala His Arg Pro Trp Leu Ile Thr Lys Glu
225                 230                 235                 240

His Ile Glu Gly Leu Leu Lys Ala Glu Glu His Ser Trp Ser Leu Ala
                245                 250                 255

Glu Leu Val His Ala Val Val Leu Leu Thr His Tyr His Ser Leu Ala
                260                 265                 270

Ser Phe Thr Phe Gly Cys Gly Ile Ser Pro Glu Ile His Cys Asp Gly
                275                 280                 285

Gly His Thr Phe Arg Pro Pro Ser Val Ser Asn Tyr Cys Ile Cys Asp
            290                 295                 300

Ile Thr Asn Gly Asn His Ser Val Asp Glu Met Pro Val Asn Ser Ala
305                 310                 315                 320

Glu Asn Val Ser Val Ser Asp Ser Phe Phe Glu Val Glu Ala Leu Met
                325                 330                 335

Glu Lys Met Arg Gln Leu Gln Glu Cys Arg Asp Glu Glu Glu Ala Ser
                340                 345                 350

Gln Glu Glu Met Ala Ser Arg Phe Glu Ile Glu Lys Arg Glu Ser Met
            355                 360                 365

Phe Val Phe Ser Ser Asp Asp Glu Glu Val Thr Pro Ala Arg Ala Val
    370                 375                 380

Ser Arg His Phe Glu Asp Thr Ser Tyr Gly Tyr Lys Asp Phe Ser Arg
385                 390                 395                 400

His Gly Met His Val Pro Thr Phe Arg Val Gln Asp Tyr Gln Trp Glu
                405                 410                 415

Asp His Gly Tyr Ser Leu Val Asn Arg Leu Tyr Pro Asp Val Gly Gln
            420                 425                 430

Leu Ile Asp Glu Lys Phe His Ile Ala Tyr Asn Leu Tyr Asn Thr
    435                 440                 445

Met Ala Met His Lys Asp Val Asp Thr Ser Met Leu Arg Arg Ala Ile
    450                 455                 460

Trp Asn Tyr Ile His Cys Met Phe Gly Ile Arg Tyr Asp Asp Tyr Asp
465                 470                 475                 480

Tyr Gly Glu Ile Asn Gln Leu Leu Asp Arg Ser Phe Lys Val Tyr Ile
                485                 490                 495

Lys Thr Val Val Cys Thr Pro Glu Lys Val Thr Lys Arg Met Tyr Asp
                500                 505                 510

Ser Phe Trp Arg Gln Phe Lys His Ser Glu Lys Val His Val Asn Leu
    515                 520                 525

Leu Leu Ile Glu Ala Arg Met Gln Ala Glu Leu Leu Tyr Ala Leu Arg
    530                 535                 540

Ala Ile Thr Arg Tyr Met Thr
545                 550
```